(12) United States Patent
Kellogg et al.

(10) Patent No.: US 10,815,309 B2
(45) Date of Patent: *Oct. 27, 2020

(54) METHODS FOR PREPARING ANTIBODY-DRUG CONJUGATES

(71) Applicant: ImmunoGen Inc., Waltham, MA (US)

(72) Inventors: Brenda A. Kellogg, Medford, MA (US); Rajeeva Singh, Framingham, MA (US); Ravi V. Chari, Newton, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,249

(22) Filed: Feb. 1, 2019

(65) Prior Publication Data

US 2019/0263935 A1    Aug. 29, 2019

Related U.S. Application Data

(63) Continuation of application No. 15/694,164, filed on Sep. 1, 2017, now Pat. No. 10,233,257, which is a
(Continued)

(51) Int. Cl.
*C07K 16/46* (2006.01)
*C07D 213/71* (2006.01)
(Continued)

(52) U.S. Cl.
CPC ............ *C07K 16/46* (2013.01); *A61K 47/60* (2017.08); *A61K 47/6803* (2017.08);
(Continued)

(58) Field of Classification Search
CPC ............... A61K 47/60; A61K 47/6803; A61K 47/6849; A61K 47/6851; A61K 47/6855;
(Continued)

(56) References Cited

U.S. PATENT DOCUMENTS

| | | | |
|---|---|---|---|
| 4,137,230 A | 1/1979 | Hashimoto et al. | |
| 4,149,003 A | 4/1979 | Carlsson et al. | |

(Continued)

FOREIGN PATENT DOCUMENTS

| | | |
|---|---|---|
| CM | 2006408 A1 | 6/1990 |
| CN | 101267841 A | 9/2008 |

(Continued)

OTHER PUBLICATIONS

Poison et al. (Blood, Jul. 15, 2007, vol. 110 (2), p. 616-623).*
(Continued)

*Primary Examiner* — Valerie Rodriguez-Garcia
(74) *Attorney, Agent, or Firm* — Nixon & Vanderhye, PC

(57) ABSTRACT

This invention describes a method of conjugating a cell binding agent such as an antibody with an effector group (e.g., a cytotoxic agent) or a reporter group (e.g., a radionuclide), whereby the reporter or effector group is first reacted with a bifunctional linker and the mixture is then used without purification for the conjugation reaction with the cell binding agent. The method described in this invention is advantageous for preparation of stably-linked conjugates of cell binding agents, such as antibodies with effector or reporter groups. This conjugation method provides in high yields conjugates of high purity and homogeneity that are without inter-chain cross-linking and inactivated linker residues.

19 Claims, 25 Drawing Sheets

Related U.S. Application Data continuation of application No. 15/167,476, filed on May 27, 2016, now Pat. No. 9,771,432, which is a continuation of application No. 14/095,579, filed on Dec. 3, 2013, now Pat. No. 9,376,500, which is a continuation of application No. 12/793,175, filed on Jun. 3, 2010, now Pat. No. 8,624,003.

(60) Provisional application No. 61/183,774, filed on Jun. 3, 2009.

(51) Int. Cl.
    *A61K 47/68* (2017.01)
    *A61K 47/60* (2017.01)
    *C07D 498/14* (2006.01)

(52) U.S. Cl.
    CPC ...... *A61K 47/6849* (2017.08); *A61K 47/6851* (2017.08); *A61K 47/6855* (2017.08); *A61K 47/6863* (2017.08); *A61K 47/6891* (2017.08); *C07D 213/71* (2013.01); *C07D 498/14* (2013.01); *C07K 2317/21* (2013.01); *C07K 2317/24* (2013.01)

(58) Field of Classification Search
    CPC . A61K 47/6863; A61K 47/6891; A61P 35/00; C07D 213/71; C07D 498/14; C07K 16/46; C07K 2317/21; C07K 2317/24
    See application file for complete search history.

(56) References Cited

U.S. PATENT DOCUMENTS

| | | |
|---|---|---|
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,563,304 A | 1/1986 | Carlsson et al. |
| 4,664,911 A | 5/1987 | Uhr et al. |
| 4,780,210 A | 10/1988 | Hsia |
| 4,859,449 A | 8/1989 | Mattes |
| 4,859,499 A | 8/1989 | Sauvinet et al. |
| 5,024,834 A | 6/1991 | Houston et al. |
| 5,208,020 A | 5/1993 | Chari et al. |
| 5,225,539 A | 7/1993 | Winter |
| 5,241,078 A | 8/1993 | Moreland et al. |
| 5,252,714 A | 10/1993 | Harris et al. |
| 5,416,064 A | 5/1995 | Chari et al. |
| 5,475,092 A | 12/1995 | Chari et al. |
| 5,529,986 A | 6/1996 | Larsson et al. |
| 5,545,806 A | 8/1996 | Lonberg et al. |
| 5,552,293 A | 9/1996 | Lindholm et al. |
| 5,556,623 A | 9/1996 | Barton et al. |
| 5,569,825 A | 10/1996 | Lonberg et al. |
| 5,580,853 A | 12/1996 | Sytkowski |
| 5,585,089 A | 12/1996 | Queen et al. |
| 5,585,499 A | 12/1996 | Chari et al. |
| 5,612,474 A | 3/1997 | Patel |
| 5,639,641 A | 6/1997 | Pedersen et al. |
| 5,665,357 A | 9/1997 | Rose et al. |
| 5,693,761 A | 12/1997 | Queen et al. |
| 5,693,762 A | 12/1997 | Queen et al. |
| 5,714,149 A | 2/1998 | Rhind et al. |
| 5,714,352 A | 2/1998 | Jakobovits |
| 5,747,446 A | 5/1998 | Sytkowski |
| 5,846,545 A | 12/1998 | Chari et al. |
| 5,885,793 A | 3/1999 | Griffiths et al. |
| 5,919,758 A | 7/1999 | Sytkowski |
| 5,965,714 A | 10/1999 | Ryall |
| 5,969,108 A | 10/1999 | McCafferty et al. |
| 6,171,586 B1 | 1/2001 | Lam et al. |
| 6,235,716 B1 | 5/2001 | Ben-Sasson |
| 6,265,150 B1 | 7/2001 | Terstappen et al. |
| 6,316,003 B1 | 11/2001 | Frankel et al. |
| 6,333,410 B1 | 12/2001 | Chari et al. |
| 6,340,461 B1 | 1/2002 | Terman |
| 6,340,701 B1 | 1/2002 | Chari et al. |
| 6,371,975 B2 | 4/2002 | Cruise et al. |
| 6,372,738 B2 | 4/2002 | Chari et al. |
| 6,391,913 B1 | 5/2002 | Page et al. |
| 6,436,931 B1 | 8/2002 | Chari et al. |
| 6,441,163 B1* | 8/2002 | Chari ............ C07D 498/18 540/458 |
| 6,462,070 B1 | 10/2002 | Hasan et al. |
| 6,534,660 B1 | 3/2003 | Yongxin et al. |
| 6,573,245 B1 | 6/2003 | Marciani |
| 6,586,618 B1 | 7/2003 | Zhao et al. |
| 6,596,757 B1 | 7/2003 | Chari et al. |
| 6,630,579 B2 | 10/2003 | Chari et al. |
| 6,632,979 B2 | 10/2003 | Erickson et al. |
| 6,706,708 B2 | 3/2004 | Chari et al. |
| 6,716,821 B2 | 4/2004 | Zhao et al. |
| 6,756,397 B2 | 6/2004 | Zhao et al. |
| 6,875,886 B2 | 4/2005 | Frangioni |
| 6,913,748 B2 | 7/2005 | Widdison |
| 7,045,605 B2 | 5/2006 | Bander et al. |
| 7,097,840 B2 | 8/2006 | Erickson et al. |
| 7,196,073 B2 | 3/2007 | Marciani |
| 7,368,565 B2 | 5/2008 | Chari et al. |
| 7,575,748 B1 | 8/2009 | Erickson et al. |
| 7,642,044 B2 | 1/2010 | Thogersen et al. |
| 7,811,572 B2 | 10/2010 | Dai et al. |
| 7,964,415 B2 | 6/2011 | Zhelev et al. |
| 8,088,387 B2 | 1/2012 | Steeves et al. |
| 8,206,901 B2 | 6/2012 | Freskgard et al. |
| 8,383,122 B2 | 2/2013 | Dai et al. |
| 8,557,966 B2 | 10/2013 | Ab et al. |
| 8,624,003 B2* | 1/2014 | Kellogg ............ A61K 47/6855 530/391.9 |
| 8,795,673 B2 | 8/2014 | Li et al. |
| 8,840,877 B2 | 9/2014 | Adamson et al. |
| 8,933,205 B2 | 1/2015 | Dai et al. |
| 9,376,500 B2* | 6/2016 | Kellogg ............ A61K 47/60 |
| 9,428,543 B2 | 8/2016 | Li et al. |
| 9,771,432 B2* | 9/2017 | Kellogg ............ A61K 47/6849 |
| 9,789,204 B2 | 10/2017 | Dai et al. |
| 9,914,748 B2 | 3/2018 | Li et al. |
| 10,035,817 B2 | 7/2018 | Chen et al. |
| 10,233,257 B2* | 3/2019 | Kellogg ............ A61K 47/6851 |
| 10,435,432 B2 | 10/2019 | Li et al. |
| 2002/0001587 A1 | 1/2002 | Erickson et al. |
| 2002/0150585 A1 | 10/2002 | Marciani |
| 2002/0197266 A1 | 12/2002 | Debinski |
| 2003/0004210 A1 | 1/2003 | Chari et al. |
| 2003/0055226 A1 | 3/2003 | Chari et al. |
| 2003/0195365 A1 | 10/2003 | Zhao et al. |
| 2004/0024049 A1 | 2/2004 | Baloglu et al. |
| 2004/0192900 A1 | 9/2004 | Kunz et al. |
| 2004/0220142 A1 | 11/2004 | Marciani |
| 2004/0235840 A1 | 11/2004 | Chari et al. |
| 2004/0241174 A1 | 12/2004 | Amphlett et al. |
| 2005/0031627 A1 | 2/2005 | Mazzola et al. |
| 2005/0053608 A1 | 3/2005 | Weber et al. |
| 2005/0074425 A1 | 4/2005 | Waugh et al. |
| 2005/0112130 A1 | 5/2005 | Bhat et al. |
| 2005/0118183 A1 | 6/2005 | Hoffee et al. |
| 2005/0169933 A1 | 8/2005 | Steeves et al. |
| 2005/0175619 A1 | 8/2005 | Duffy et al. |
| 2005/0261232 A1 | 11/2005 | Strong et al. |
| 2006/0024317 A1 | 2/2006 | Boyd et al. |
| 2006/0062786 A1 | 3/2006 | Salcedo et al. |
| 2006/0073528 A1 | 4/2006 | Lecerf et al. |
| 2006/0099592 A1 | 5/2006 | Freskgard et al. |
| 2006/0100163 A1 | 5/2006 | Orlando et al. |

(56) References Cited

U.S. PATENT DOCUMENTS

| | | | |
|---|---|---|---|
| 2006/0153834 A1 | 7/2006 | Carbonell et al. | |
| 2006/0182740 A1 | 8/2006 | Yang et al. | |
| 2006/0182750 A1 | 8/2006 | Chari et al. | |
| 2006/0193865 A1 | 8/2006 | Govindan | |
| 2006/0233811 A1 | 10/2006 | Chari | |
| 2007/0031402 A1 | 2/2007 | Zhang et al. | |
| 2007/0048314 A1 | 3/2007 | Dai et al. | |
| 2007/0154901 A1 | 7/2007 | Thogersen et al. | |
| 2007/0155750 A1 | 7/2007 | Neamati et al. | |
| 2007/0196275 A1 | 8/2007 | Li et al. | |
| 2007/0264257 A1 | 11/2007 | Dunussi-Joannopoulos et al. | |
| 2008/0050310 A1* | 2/2008 | Ebens, Jr. | A61K 45/06 424/1.49 |
| 2008/0166363 A1 | 7/2008 | Govindan et al. | |
| 2008/0171040 A1 | 7/2008 | Ebens et al. | |
| 2008/0171865 A1 | 7/2008 | Steeves et al. | |
| 2008/0213349 A1 | 9/2008 | Thakker et al. | |
| 2008/0279868 A1 | 11/2008 | Boyd et al. | |
| 2008/0305044 A1 | 12/2008 | McDonagh et al. | |
| 2009/0274713 A1 | 11/2009 | Chari et al. | |
| 2010/0003719 A1 | 1/2010 | Thagersen et al. | |
| 2010/0047257 A1 | 2/2010 | Blanc et al. | |
| 2010/0129314 A1 | 5/2010 | Singh et al. | |
| 2010/0203007 A1 | 8/2010 | Li et al. | |
| 2010/0291021 A1 | 11/2010 | Vetter et al. | |
| 2010/0316656 A1 | 12/2010 | Bouchard et al. | |
| 2011/0003969 A1 | 1/2011 | Kellogg et al. | |
| 2011/0064754 A1 | 3/2011 | Taylor et al. | |
| 2011/0166319 A1 | 7/2011 | Dai et al. | |
| 2011/0206658 A1 | 8/2011 | Crowley et al. | |
| 2011/0221744 A1 | 9/2011 | Bae et al. | |
| 2011/0223257 A1 | 9/2011 | Zhao et al. | |
| 2012/0149732 A1 | 6/2012 | Chucholowski et al. | |
| 2012/0225089 A1 | 9/2012 | Bouchard et al. | |
| 2012/0226026 A1 | 9/2012 | Singh et al. | |
| 2012/0238731 A1 | 9/2012 | Fishkin et al. | |
| 2012/0253021 A1 | 10/2012 | Li et al. | |
| 2012/0259100 A1 | 10/2012 | Jin | |
| 2012/0282175 A1 | 11/2012 | Carrigan et al. | |
| 2013/0071482 A1 | 3/2013 | Bae et al. | |
| 2013/0281678 A1 | 10/2013 | Dai et al. | |
| 2014/0179906 A1 | 6/2014 | Kellogg et al. | |
| 2014/0309406 A1 | 10/2014 | Li et al. | |
| 2014/0350228 A1 | 11/2014 | Liu et al. | |
| 2015/0010494 A1 | 1/2015 | Adamson et al. | |
| 2015/0182635 A1 | 7/2015 | Dai et al. | |
| 2015/0225446 A1 | 8/2015 | Chen et al. | |
| 2015/0297742 A1 | 10/2015 | Strieker et al. | |
| 2015/0306242 A1 | 10/2015 | Li et al. | |
| 2015/0307596 A1 | 10/2015 | Li et al. | |

FOREIGN PATENT DOCUMENTS

| | | |
|---|---|---|
| EP | 0239400 A2 | 9/1987 |
| EP | 0425235 A2 | 5/1991 |
| EP | 0457250 A2 | 11/1991 |
| EP | 0485749 A2 | 5/1992 |
| EP | 1258255 A1 | 11/2002 |
| EP | 2468304 A2 | 6/2012 |
| GB | 2188638 A | 10/1987 |
| JP | H03161490 A | 7/1991 |
| JP | H04266829 A | 9/1992 |
| JP | 2000026404 A | 1/2000 |
| JP | 2004/520450 A | 7/2004 |
| JP | 2004532639 A | 10/2004 |
| JP | 2007/514646 A | 6/2007 |
| JP | 6000329 B2 | 9/2016 |
| WO | WO-92/01047 A1 | 1/1992 |
| WO | WO-96/39183 A1 | 12/1996 |
| WO | WO-99/06587 A2 | 2/1999 |
| WO | WO-1999/005317 A1 | 2/1999 |
| WO | WO-00/02587 A1 | 1/2000 |
| WO | WO-2000/066091 A1 | 11/2000 |
| WO | WO-01/24763 A2 | 4/2001 |
| WO | WO-02/16368 A1 | 2/2002 |
| WO | WO-02/16401 A2 | 2/2002 |
| WO | WO-02/060955 A2 | 8/2002 |
| WO | WO-02/092127 A1 | 11/2002 |
| WO | WO-02/094325 A2 | 11/2002 |
| WO | WO-02/098883 A1 | 12/2002 |
| WO | WO-2002/098887 A1 | 12/2002 |
| WO | WO-2002/098897 A2 | 12/2002 |
| WO | WO-03/053462 A2 | 7/2003 |
| WO | WO-2003/057163 A2 | 7/2003 |
| WO | WO-03/092623 A2 | 11/2003 |
| WO | WO-03/102132 A2 | 12/2003 |
| WO | WO-2004/103272 A2 | 12/2004 |
| WO | WO-2004/110498 A2 | 12/2004 |
| WO | WO-2005/037992 A2 | 4/2005 |
| WO | WO-2005/077090 A2 | 8/2005 |
| WO | WO-2005/094882 A1 | 10/2005 |
| WO | WO-2005/112919 A2 | 12/2005 |
| WO | WO-2005/117986 A2 | 12/2005 |
| WO | WO-2006/086733 A2 | 8/2006 |
| WO | WO-2006/113623 A2 | 10/2006 |
| WO | WO-2007/009229 A1 | 1/2007 |
| WO | WO-2007/024536 A2 | 3/2007 |
| WO | WO-2007/034495 A2 | 3/2007 |
| WO | WO-2008/057683 A2 | 5/2008 |
| WO | WO-2009/134952 A2 | 11/2009 |
| WO | WO-2011/039724 A1 | 4/2011 |
| WO | WO-2011/106528 A1 | 9/2011 |
| WO | WO-2012/112687 A1 | 8/2012 |
| WO | WO-2012/112708 A1 | 8/2012 |
| WO | WO-2012/135517 A2 | 10/2012 |
| WO | WO-2014/055893 A1 | 4/2014 |

OTHER PUBLICATIONS

"Clinical Trials Begin of Antiangiogenesis Antibody, CNTO 95," Cancer Weekly, 57 (Jan. 13, 2004).

Al-Arif et al., "Synthesis of Fatty Acyl CoA and Other Thiol Esters Using N-Hydroxysuccinimide Esters of Fatty Acids," J Lipid Res, 10: 344-345 (1969).

Al-Katib et al., "Superior Antitumor Activity of SAR3419 to Rituximab in Xenograft Models for non-Hodgkin's Lymphoma," Clin Cancer Res, 15(12):4038-4045 (2009).

Baldus et al., "Lewis(y) Antigen (CD174) and Apoptosis in Gastric and Colorectal Carcinomas: Correlations with Clinical and Prognostic Parameters," Histol Histopathol, 21(5):503-510 (2006).

Berg et al., Biochemistry, 5th Ed., New York: WH Freeman, 1-8 (2002).

Bergelt et al., "Listeriolysin O as Cytotoxic Component of an Immunotoxin," Protein Sci, 18(6): 1210-1220 (2009).

Bhuyan et al., "CC=1-65 (NSC 298223), A Most Potent Antitumor Agent: Kinetics of Inhibition of Growth, DNA Synthesis, and Cell Survival," Cancer Res, 42(9): 3532-3537 (1982).

Boger et al., "Synthesis and Preliminary Evaluation of (+)-CBI-Indole2: An Enhanced Functional Analog of (+)-CC-1065," Bioorg Med Chem Lett, 1(2):115-120 (1991).

Boger et al., "Synthesis of N-(tert-butyloxycarbonyl)-CBI, CBI, CBI-CDPI1, and CBI-CDPI2: Enhanced Functional Analogs of CC-1065 Incorporating the 1,2,9,9a-tetrahydrocyclopropa[c]benz[e]indol-4-one (CBI) Left-Hand Subunit," J Org Chem, 55(23): 5823-5833 (1990).

Boschetti et al., "Antibody Separation by Hydrophobic Charge Induction Chromatography," Trends Microbiol, 20(8): 333-337 (2002).

Brinkman et al., "A Recombinant Immunotoxin Containing a Disulfide-Stabilized Fv Fragment," Proc Natl Acad Sci USA, 90(16): 7538-7542 (1993).

Burgess, "The Complex Mediators of Cell Growth and Differentiation," Immunol Today, 5(6): 155-158 (1984).

Carlsson et al., "Protein Thiolation and Reversible Protein-Protein Conjugation. N-Succinimidyl 3-(2-pyridyldithio) Propionate, a New Heterobifunctional Reagent," Biochem J, 173(3): 723-737 (1978).

Cassidy et al., "Purification of staphylococcal alpha-toxin by adsorption chromatography on glass," Infect Immun, 13(3): 982-986 (1976).

(56) References Cited

OTHER PUBLICATIONS

Chari et al., "Enhancement of the Selectivity and Antitumor Efficacy of a CC-1065 Analogue Through Immunoconjugates Formation," Cancer Res, 55(18): 4079-4084 (1995).
Chari et al., "Immunoconjugates Containing Novel Maytansinoids: Promising Anticancer Drugs," Cancer Res, 52(1): 127-131 (1992).
Chen et al., "Factors affecting endotoxin removal from recombinant therapeutic proteins by anion exchange chromatography," Protein Expr Purif, 64(1): 76-81 (2009).
Christy et al., "High-Performance Tangential Flow Filtration: A Highly Selective Membrane Separation Process," Desalination, 144(1-3): 133-136 (2002).
Colomer et al., "Herceptin: from the Bench to the Clinic," Cancer Invest, 19(1): 49-56 (2001).
Desmyter et al., "Crystal Structure of a camel Single-Domain VH Antibody Fragment in Complex with Lysozyme," Nat Struct Biol, 3(9): 803-811 (1996).
Erickson et al., "Antibody-Maytansinoid Conjugates Are Activated in Targeted Cancer Cells by Lysosomal Degradation and Linker-Dependent Intracellular Processing," Cancer Res. 66: 4426-4433 (2006).
European Search Report issued by the European Patent Office in corresponding Application No. 13844268.6, dated Apr. 3, 2017.
Extended European Search Report for European Application No. 10783998.7 dated May 28, 2015.
Extended European Search Report for European Application No. 12856692.4 dated Jul. 3, 2015.
Extended European Search Report issued by the European Patent Office in corresponding Application No. 13843881.7, dated Apr. 11, 2016.
Extended European Search Report issued by the European Patent Office in corresponding Application No. EP 18196502 dated Apr. 4, 2019.
Gao et al., "Expression of Lewis y Antigent and Integrin AlphaV, Beta3 in Ovarian Cancer and Their Relationship with chemotherapeutic Drug Resistance," J Exp Clin Canc Res, 32: 36 (2013).
Ghetie et al., "Large Scale Preparation of Immunotoxins Constructed with the Fab'fragment of IgG1 Murine Monoclonal Antibodies and Chemically Deglycosylated Ricin A Chain," J Immunol Methods, 112(2): 267-277 (1988).
Gong et al., "Comparison of DNA Immobilization Efficiency on New and Regenerated Commercial Amine-Reactive Polymer Microarray Surfaces," Surf Sci, 570: 67-77 (2004).
Greenberg et al., "A New Antigen Receptor Gene Family that Undergoes Rearrangement and Extensive Somatic Diversification in Sharks," Nature, 374 (6518): 168-173 (1995).
Griffin et al., "A Monoclonal Antibody Reactive with Normal and Leukemic Human Myeloid Progenitor Cells," Leukemia Res, 8(4): 521-534 (1984).
Hamann et al., "An Anti-CD33 Antibody-Calicheamicin Conjugate for Treatment of Acute Myeloid Leukemia. Choice of Linker," Bioconj. Chem., 13(1):40-46 (2002).
Haskard et al., "The Production of Human Monoclonal Autoantibodies from Patients with Rheumatoid Arthritis by the EBV-hybridoma Technique," J Immunol Methods, 74(2): 361-367 (1984).
Heider et al., "Splice Variants of the Cell Surface Glycoprotein CD44 Associated with Metastatic Tumour Cells Are Expressed in Normal Tissues of Humans and Cynomolgus Monkeys," Eur J Cancer, 31A(13-14): 2385-2391 (1995).
Henning, "Tumor Cell Targeted Gene Delivery by Adenovirus 5 Vectors Carrying Knobless Fibers with Antibody-binding Domains," Gene Ther, 12(3): 211-224 (2005).
Hsiao et al., "Direct cell surface modification with DNA for the capture of primary cells and the investigation of myotube formation on defined patterns," Langmuir, 25(12):6985-6991 (2009).
Hurwitz et al., "The Covalent Binding of Daunomycin and Adriamycin to Antibodies, with Retention of Both Drug and Antibody Activities," Cancer Res, 35: 1175-1181 (1975).

Huse et al., "Generation of a Large Combinatorial Library of the Immunoglobulin Repertoire in Phage Lambda," Science, 246(4935): 1275-1281 (1989).
Instructions for SMCC and Sulfo-SMCC, Thermo Scientific, 1-4 (2007).
International Search Report and Written Opinion for International Application No. PCT/US10/37046, dated Jul. 30, 2010.
International Search Report and Written Opinion for International Application No. PCT/US12/031243, dated Dec. 10, 2012.
International Search Report and Written Opinion for International Application No. PCT/US12/31253, dated Dec. 7, 2012.
International Search Report and Written Opinion for International Application No. PCT/US2006/004937 dated Apr. 11, 2007.
International Search Report and Written Opinion for International Application No. PCT/US2006/031653 dated Apr. 3, 2007.
International Search Report and Written Opinion for International Application No. PCT/US2012/069527 dated Feb. 20, 2013.
International Search Report and Written Opinion for International Application No. PCT/US2013/63415, dated Jan. 29, 2014.
International Search Report and Written Opinion for International Application No. PCT/US2013/63480 dated Jan. 16, 2014.
International Search Report and Written Opinion for International Application No. PCT/US2013/63503 dated Jan. 16, 2014.
International Search Report for International Application No. PCT/US2002/03378 dated Jun. 12, 2002.
Jayson et al., "Phase I Study of CNTO 95, a Fully Human Monoclonal Antibody (mAb) to alphav Integrins, in Patients with Solid Tumors," J Clin Oncol, 22(14): 3119 (2004).
Jensen et al., "Targeting the Neural Cell Adhesion Molecule in Cancer," Cancer Lett, 258(1): 9-21 (2007).
Jiao et al., "Pharmacokinetics of CNTO 95, a Fully Human MAB to Human Integrin Receptors Following Single or Multiple IV Injections to Cynomolgus Monkeys," Eur J Cancer, 2(8): 93 (2004).
Kahn et al., "Purification of plasmid DNA by tangential flow filtration," Biotechnol Bioeng, 69(1): 101-106 (2000).
Kawai et al., "Chemical Modification of Ansamitocin. III. Synthesis and Biological Effects of 3-acyl Esters of Maytansinol," Chem Pharm Bull, 32(9): 3441-3451 (1984).
Kellogg et al., "Antibody-maytansinoid conjugates with hydrophilic linkers: cytotoxic therapeutics with enhanced potency against cancer cells with low antigen number and multidrug resistance," abstract 5480, 2009 AACR annual meeting (2009).
Kida et al., "Design and synthesis of a Tat-related gene transporter: a tool for carrying the adenovirus vector into cells," Bioorg Med Chem Lett, 16(3):743-745 (2006).
Kinoshita et al., "Enzyme Immunoassay for Captopril," J. Pharm. Sci., 75(7):711-713 (1986).
Kohler et al., "Derivation of Specific Antibody-Producing Tissue Culture and Tumor Lines by Cell Fusion," Eur J Immunol, 6: 511-519 (1976).
Kupchan et al., "Structural Requirements for Antileukemic Activity Among the Naturally Occurring and Semisynthetic Maytansinoids," J Med Chem, 21(1): 31-37 (1978).
Ladino et al., "Folate-Maytansinoids: Target-Selective Drugs of Low Molecular Weight," Int J Cancer, 73(6): 859-864 (1997).
Leamon et al., "Folate Copolymer-Mediated Transfection of Cultured Cells," Bioconjug Chem, 10(6):947-957 (1999).
Lewis et al., "An Improved Method for Conjugating Monoclonal Antibodies with N-hydroxysulfosuccinimidyl DOTA," Bioconjugate Chem, 12(2): 320-324 (2001).
Liu et al, "Cure of Human Small Cell Lung Cancer Xenografts in SCID Mice by a hN901-maytansinoid Immunoconjugate," 1997 AACR Annual Meeting, Abstract 190 (1997).
Liu et al, "Cure of Human Small Cell Lung Cancer Xenografts in SCID Mice by a hN901-maytansinoid Immunoconjugate," Proc Natl Acad Sci USA, 93(16): 8618-8623 (1996).
Liu et al., "Cure of Human Small Lung Cancer Xenografts in SCID Mice by a hN901-maytasinoid Immunoconjugate," Proc Natl Acad Sci Usa, 38(0): 29 (1997).
Liu et al., "Monoclonal Antibodies to the Extracellular Domain of Prostate-Specific Membrane Antigen Also React with Tumor Vascular Endothelium," Cancer Res, 57(17): 3629-3634 (1997).

(56) References Cited

OTHER PUBLICATIONS

Lundberg et al., "Click Assisted One-Pot Multi-Step Reactions in Polymer Science: Accelerated Synthetic Protocols," Macromol Rapid Comm, 29: 998-1015 (2008).
Maloney et al., "IDEC-C2B8 (Rituximab) Anti-CD20 Monoclonal Antibody Therapy in Patients with Relapsed Low-grade non-Hodgkin's Lymphoma," Blood, 90(6): 2188-2195 (1997).
Manosroi et al., "Thermo-stability and Antitumor Activity on Colon Cancer Cell Lines of Monoclonal Anti-CEA Antibody-Saporin Immunotoxin," J Korean Med Sci, 7(2): 128-135 (1992).
McDonagh et al., "Engineered anti-CD70 antibody-drug conjugate with increased therapeutic index," Mol Cancer Ther, 7(9): 2913-2923 (2008).
Merriam Webster, Online Dictionary, "Room Temperature," [retrieved at URL: http://www.merriam-webster.com/medical/room%20temperature on Dec. 12, 2014].
Nadler et al., "B4, a Human B Lymphocyte-associated Antigen Expressed on Normal, Mitogen-activated, and Malignant B Lymphocytes," J Immunol, 131(1): 244-250 (1983).
Nisonoff et al., "Separation of Univalent Fragments from the Bivalent Rabbit Antibody Molecule by Reduction of Disulfide Bonds," Arch Biochem Biophys, 89: 230-244 (1960).
O'Keefe et al., "Characterization of a Transferrin-diphtheria Toxin Conjugate," J Biol Chem, 260(2): 932-937 (1985).
Okamoto et al., "Therapeutic Effect of Ansamitocin Targeted to Tumor by a Bispecific Monoclonal Antibody," Jpn J Cancer Res, 83(7): 761-768 (1992).
Parham, "On the Fragmentation of Monoclonal IgG1, IgG2b from BALB/c Mice," J Immunol, 131(6): 2895-2902 (1983).
Pastan et al., "Characterization of Monoclonal Antibodies B1 and B3 that React with Mucinous Adenocarcinomas," Cancer Res, 51(14): 3781-3787 (1991).
Pedersen et al., "Comparison of Surface Accessible residues in Human and Murine Immunoglobulin Fv Domains. Implication for humanization of Murine Antibodies," J Mol Biol, 235(3): 959-973 (1994).
Phillips et al., "Targeting HER2-positive breast cancer with trastuzumab-DM1, an antibody-cytotoxic drug conjugate," Cancer Res, 68(22):9280-9290 (2008).
Pietersz, "The Linkage of Cytotoxic Drugs to Monoclonal Antiboies for the Treatment of Cancer," Bioconjugate Chem, 1(2): 89-95 (1990).
Reider et al., "Maytansinoids," The Alkaloids, XXII, 71-73 (1984).
Reis et al., "High-performance tangential flow filtration using charged membranes," J Membrane Sci, 159(1-2): 133-142 (1999).
Reiter et al., "Engineering Interchain Disulfide Bonds into Conserved Framework Regions of Fv Fragments: Improved Biochemical Characteristics of Recombinant Immunotoxins Containing Disulfide-Stabilized Fv," Protein Engineering, 7(5): 697-704 (1994).
Ritz et al., "A Monoclonal Antibody to Human Acute Lymphoblastic Leukaemia Antigen," Nature, 283(5747): 583-585 (1980).
Roder et al., "The EBV-hybriodoma Technique," Methods Enzymol, 121: 140-167 (1986).
Roguska et al., "Humanization of Murine Monoclonal Antibodies Through Variable Domain Resurfacing," Proc Natl Acad Sci USA, 91(3): 969-973 (1974).
Sehgal et al., "A Method for the High Efficiency of Water-Soluble Carbodiimide-Mediated Amidation," Anal Biochem, 218: 87-91 (1994).
Smith, "Technology Evaluation: C242-DM1, ImmunoGen Inc.," Curr Opin Mol Ther, 3(2): 198-203 (2001).
Spring et al., "Allotypic Markers on Fab Fragments of Mouse Immunoglobulins," J Immunol, 113(2): 470-478 (1974).
Stanfield et al., "Crystal Structure of a Shark Single-Domain Antibody V Region in Complex with Lysozyme," Science, 305(5691): 1770-1773 (2004).
Stryer et al., "Levels of Structure in Protein Architecture," Biochemistry, 3rd Ed., New York: WH Freeman, 31-33 (1998).
Sytkowski et al., "Human Erythropoietin Dimers with Markedly Enhanced in Vivo Activity," Proc Natl Acad Sci USA, 95(3): 1184-1188 (1998).
Taylor-Papadimitriou et al., "Monoclonal Antibodies to Epithelium-Specific Components of the Human Milk Fat Globule Membrane: Production and Reaction with Cells in Culture," Int J Cancer, 28: 17-21 (1981).
Trikha et al., "CNTO 95, a Fully Human Monoclonal Antibody that Inhibits alphav Integrins, Has Antitumor and Antiangiogenic Activity in Vivo," Int J Cancer, 110(3): 326-335 (2004).
Trouet et al., "A Covalent Linkage Between Daunorubicin and Proteins that is Stable in Serum and Reversible by Lysosomal Hydrolases, as Required for a Lysosomotrophic Drug-Carrier Conjugate: In vitro and in vivo Studies," Proc Natl Acad Sci USA, 79: 626-629 (1982).
Tugcu et al., "Maximizing productivity of chromatography steps for purification of monoclonal antibodies," Biotechnol Bioeng, 99(3): 599-613 (2008).
Ugwu et al., "The Effect of Buffers on Protein Conformational Stability," Pharmaceutical Technology, 86, 88, 90, 92, 94, 96, 98, 100, 102, 104, 106, 108, 110-113 (2004).
Umemoto et al., "Preparation and in Vitro Cytotoxicity of a Methotrexate-anti-MM46 Monoclonal Antibody Conjugate via an Oligopepetide Spacer," Int J Cancer, 43(4): 677-684 (1989).
Van Hof et al., "Biodistribution of (111)indium-labeled Engineered Human Antibody CTMO1 in Ovarian Cancer Patients: Influence of Protein Dose," Cancer Res, 56(22): 5179-5185 (1996).
Wang et al., "Trichosanthin-monoclonal Antibody Conjugate Specifically Cytotoxic to Human Hepatoma Cells in Vitro," Cancer Res, 51: 3353-3355 (1991).
Warpehoski et al., "Stereoelectronic Factors Influencing the Biological Activity and DNA Interaction of Synthetic Antitumor Agents Modeled on CC-1065," J Med Chem, 31(3): 590-603 (1988).
Wawryznczak et al., Molecular and Biological Properties of an Arbin A Chain Immunotoxin Designated for Therapy of Human Small Cell Lung Cancer, Br J Cancer, 66(2): 361-366 (1992).
Welt et al., Antibody Targeting in Metastic Colon Cancer: A Phase I Study of J Clin Oncol, 12(6): 1193-1203 (1994).
Winkler et al., "Changing the Antigen Binding Specificity by Single Point Mutations of an Anti-p24 (HIV-1) Antibody," J Immunol, 165(8): 4505-4514 (2000).
Written Opinion and International Search Report dated Jul. 30, 2010, as issued in International Patent Application No. PCT/US10/37046, filed Jun. 2, 2010.
Yan et al., "Enhancement of the Adhesive and Spreading Potentials of Ovarian Carcinomas RMG-1 Cells Due to Increased Expression of Integrin Alpha5beta1 with the Lewis Y-structure on Transfection of the Alpha1,2-fucosyltransferase Gene," Biochimie, 92(7): 852-857 (2010).
Yin et al., "Phagemid Encoded Small Molecules for High Throughput Screening of Chemical Libraries," J. Am. Chem. Soc., 126(42):13570-13571 (2004).
Yin et al., "Supporting Information—Phagemid Encoded Small Molecules for High Throughput Screening of Chemical Libraries," J. Am. Chem. Soc., 126(42):S1-S8 (2004).
Zhou et al., "New Q membrane scale-down model for process-scale antibody purification," J Chromatogr A, 1134(1-2): 66-73 (2006).
Extended European Search Report for EP application No. EP18199729 dated Aug. 22, 2019.
Extended European Search Report for EP application No. EP19156303 dated Aug. 6, 2019.

\* cited by examiner

| | | % of Total Protein Mass Loaded | | |
|---|---|---|---|---|
| | Band MW (kDa) | Unconjugated Ab | Ab-PEG4-Mal-DM4 This method | Ab-PEG4-Mal-DM4 2 Step |
| | 17 | 1 | 2 | 1 |
| L Chain | 27 | 30 | 30 | 8 |
| | 56 | 4 | 2 | - |
| H Chain | 61 | 65 | 58 | 16 |
| | 94 | - | 6 | 26 |
| | 122 | - | 2 | 7 |
| | 147 | - | - | 12 |
| | 169 | - | - | 31 |

| | Band MW (kDa) | % Total Protein Mass Loaded | | |
| --- | --- | --- | --- | --- |
| | | Unconjugated Ab | Ab-Sulfo-Mal-DM1 2 Step | Ab-Sulfo-Mal-DM1 This method |
| | 18 | - | - | 1 |
| L Chain | 29 | 30 | 23 | 28 |
| H Chain | 62 | 70 | 53 | 70 |
| | 99 | - | 15 | 1 |
| | 130 | 1 | 7 | 1 |
| | 152 | - | 3 | - |

| | Band MW (kDa) | % of Total Protein Mass Loaded | | |
| --- | --- | --- | --- | --- |
| | | Ab-SMCC-DM1 This Method | Unconjugated Ab | Ab-SMCC-DM1 2-Step |
| L Chain | 27 | 30 | 30 | 24 |
| | 56 | 2 | 2 | 2 |
| H Chain | 61 | 67 | 68 | 54 |
| | 96 | 1 | - | 12 |
| | 129 | 1 | - | 6 |
| | 148 | - | - | 2 |

Antibody-maytansinoid conjugate linked via both
non-cleavable and cleavable linkers Antibody-maytansinoid conjugate linked via both
non-cleavable and cleavable linkers

METHODS FOR PREPARING ANTIBODY-DRUG CONJUGATES

CROSS-REFERENCE TO RELATED APPLICATIONS

This application is a continuation of U.S. patent application Ser. No. 15/694,164, filed Sep. 1, 2017, which is a continuation of U.S. patent application Ser. No. 15/167,476, filed May 27, 2016, now U.S. Pat. No. 9,771,432, issued Sep. 26, 2017, which is a continuation of U.S. patent application Ser. No. 14/095,579, filed Dec. 3, 2013, now U.S. Pat. No. 9,376,500, issued Jun. 28, 2016, which is a continuation of U.S. patent application Ser. No. 12/793,175, filed Jun. 3, 2010, now U.S. Pat. No. 8,624,003, which claims the benefit of U.S. Provisional Patent Application No. 61/183,774, filed Jun. 3, 2009, the entire contents of each of which are hereby incorporated by reference in their entirety.

FIELD OF THE INVENTION

This invention relates to a novel method of conjugating an effector group (e.g., a cytotoxic agent) or a reporter group (e.g., a radiolabel) to a cell binding agent, such as an antibody or a fragment thereof, via a bifunctional linker. More specifically, this invention relates to a novel method of conjugating an effector group (e.g., maytansinoids) or a reporter group (e.g., a radiolabel) to a cell binding agent (e.g., an antibody or a fragment thereof) via a bifunctional linker such that the process eliminates the steps that result in formation of undesired hydrolyzed species or undesired cross-linked species formed due to intra-molecular or inter-molecular reactions.

BACKGROUND OF THE INVENTION

Conjugates of cell binding agents, such as antibodies, with effector groups, such as small cytotoxic agents or cytotoxic proteins, are of immense interest for the development of anti-cancer therapeutics (Richart, A. D., and Tolcher, A. W., 2007, Nature Clinical Practice, 4, 245-25). These conjugates are tumor-specific due to the high specificity of the selected antibodies toward antigens expressed on the cell surface of tumor cells. Upon specific binding to the tumor cell, the antibody-cytotoxic agent conjugate is internalized and degraded inside the target cancer cell thereby releasing the active cytotoxic agent that inhibits essential cellular functions such as microtubule dynamics or DNA replication resulting in the killing of the cancer cell. Various linkers have been employed to link the antibodies with cytotoxic agents with the goal of enhancing the delivery of the agent inside the cell upon internalization and processing of the conjugate, while maintaining the desired stability of the conjugate in plasma. These linkers include disulfide linkers designed with different degrees of steric hindrance to influence their reduction kinetics with intracellular thiol, cleavable peptide linkers such as valine-citrulline linkage, and non-cleavable linkers such as thioether linkage (Widdison, W., et al., J. Med. Chem., 2006, 49, 4392-4408; Erickson, H., et al., Cancer Res., 2006, 66, 4426-4433).

Conjugates of cell binding agents such as antibodies with labels or reporter groups are useful for tumor-imaging applications in cancer patients, immunoassay applications for diagnosis of various diseases, cancer therapy using radioactive nuclide-ligand conjugates, and affinity chromatography applications for purification of bioactive agents such as proteins, peptides, and oligonucleides. The labels or reporter groups that are conjugated with cell-binding agents include fluorophores, and affinity labels such as biotin.

The conventional method of conjugation of the cell-binding agent such as an antibody (Ab) with an effector group (e.g., a cytotoxic agent) or a reporter group (e.g., a radiolabel) linked via a non-reducible linkage (such as thioether linkage) employs two distinct reaction steps with the antibody and necessitates the use of purification steps. In the first reaction step, the antibody is reacted with a heterobifunctional linker bearing two different reactive groups (e.g., X and Y). For example, in one approach, the reaction of an antibody's reactive residues (such as lysine amino residues) with the X reactive group (such as N-hydroxysuccinimide ester) of the heterobifunctional reagent results in the incorporation of the linker with Y reactive group at one or more reactive residues in the antibody (such as lysine amino residues). The initially modified antibody product must be purified from the excess linker or hydrolyzed linker reagent before the next step can occur. In the second reaction step, the linker-modified antibody containing the Y reactive group (such as maleimide or haloacetamide) is reacted with the effector such as an effector group (C) (e.g., a cytotoxic agent) containing a reactive group such as thiol to generate the antibody-effector conjugate, which is again purified in an additional purification step (see, e.g., U.S. Pat. Nos. 5,208,020, 5,416,064, or 5,024,834). Thus, in the above process, at least two purification steps are needed.

Another approach that involves two reaction and purification steps to conjugate antibody with an effector or reporter group uses the reaction of thiol residues in antibody (generated via modification of antibody with thiol-generating reagents such as 2-iminothiolane, or via mutagenesis to incorporate non-native cysteine residues, or via reduction of native disulfide bonds) with a homobifunctional linker Y-L-Y containing Y reactive groups (such as maleimide or haloacetamide).

Major drawbacks of incorporating a reactive group Y such as maleimide (or haloacetamide) in an antibody or peptide are the propensity of the reactive maleimide (or haloacetamide) groups to undergo intra- or inter-molecular reaction with the native histidine, lysine, tyrosine, or cysteine residues in antibody or peptide (Papini, A. et al., Int. J. Pept. Protein Res., 1992, 39, 348-355; Ueda, T. et al., Biochemistry, 1985, 24, 6316-6322), and aqueous inactivation of the Y maleimide group. The undesired intra-molecular or inter-molecular reaction of maleimide (or haloacetamide) groups Y incorporated in antibody with the native histidine, lysine, or cysteine residues in antibody, and aqueous inactivation of the Y maleimide group before the second reaction with the effector or reporter group C give rise to cross-linked proteins or heterogeneous conjugates and lower the efficiency of the second reaction with the effector or reporter group C. The heterogeneous conjugate product—cross-linked protein or peptide generated from the undesired reaction of the initially incorporated group Y (such as maleimide group) with native groups in the antibody or peptides (such as histidine, lysine, tyrosine, or cysteine), or with inactive maleimide residues generated by aqueous inactivation—may have inferior activity and stability than the desired homogeneous conjugate product.

Processes for conjugating antibodies to thiol-containing cytotoxic agents via disulfide linkages have been described previously (see, e.g., U.S. Pat. Nos. 5,208,020, 5,416,064, 6,441,163, U.S. Patent Publication No. 2007/0048314 A1). These processes involve the initial reaction of antibody with a heterobifunctional reagent, followed by a second reaction with a thiol-containing cytotoxic agent. An alternative process has been described in U.S. Pat. No. 6,441,163 B1 in which the disulfide-linked reactive ester of the cytotoxic agent is first purified and then reacted with the antibody, but which involves an additional reaction and purification step starting from the thiol group-containing cytotoxic agent before the reaction step with the antibody.

A further drawback of the current process to make conjugates of cell binding agents is the need for two purification steps, which lowers the overall yield and also makes the process cumbersome and uneconomical for scale-up.

In view of the foregoing, there is a need in the art to develop improved methods of preparing cell-binding agent-drug conjugate compositions that are of substantially high purity and can be prepared avoiding cumbersome steps and by reducing time and cost to the user. The invention provides such a method. These and other advantages of the invention, as well as additional inventive features, will be apparent from the description of the invention provided herein.

SUMMARY OF THE INVENTION

The present invention describes a conjugation method for preparing non-reducible, thioether-linked conjugates of the formula C-L-CBA, wherein C represents an effector or reporter molecule (e.g., a cytotoxic agent or a radiolabel), L is a linker and CBA is a cell binding agent (e.g., an antibody or a fragment thereof), by utilizing a direct reaction of the thiol-containing cytotoxic agent (e.g., maytansinoids) with a hetero- or a homo-bifunctional reagent, (e.g., cleavable or a non-cleavable linker) followed by mixing of the unpurified reaction mixture with a cell binding agent (e.g., an antibody or a fragment thereof), thereby generating the non-reducible, thioether-linked conjugate by a process that is more efficient, has a high yield, and is amenable for scale up. Another important advantage is that such conjugation method yields thioether-linked non-reducible conjugates with no interchain protein cross-linking or inactivated residues (e.g., maleimide or haloacetamide residues). The novel methods disclosed in this application can be applied to the preparation of any conjugate represented by the above formula.

BRIEF DESCRIPTION OF THE DRAWINGS

FIG. 3A shows Protein LabChip electrophoresis under reducing condition (Agilent 2100 Bioanalyzer/Agilent Protein 230 kit) of Ab-($PEG_4$-Mal)-DM4 conjugates. Lane 1: molecular weight markers; lane 2: Ab-$PEG_4$-Mal-DM4, 6.2 D/Ab, synthesized using the method described in this invention; lane 3: Ab-$PEG_4$-Mal-DM4, 6.1 D/Ab, synthesized using the 2 step conjugation method; lane 4: unconjugated Ab (0.24 microgram total protein in each lane). The upper marker, system peak and lower marker bands represent external markers added from kit. FIG. 3B shows the quantitation of protein bands from Protein LabChip electrophoresis.

FIG. 4A shows MS of conjugate prepared by the traditional two-step method with 6.1 DM4 per Ab. Due to significant heterogeneity of the conjugate the MS peaks could not be resolved well. FIG. 4B shows MS of conjugate prepared by the method described in this invention and contained 6.2 DM4 per Ab. Due to homogeneity of the conjugate, the MS peaks were well resolved.

FIG. 9A shows Protein LabChip electrophoresis under reducing condition (Agilent 2100 Bioanalyzer/Agilent Protein 230 kit) of Ab-(Sulfo-Mal)-DM1 conjugates. Lane 1: molecular weight markers; lane 2: unconjugated Ab; lane 3: Ab-Sulfo-Mal-DM1, 5.7 D/Ab, synthesized using the 2 step conjugation method; lane 4: Ab-Sulfo-Mal-DM1, 5.6 D/Ab, synthesized using the method described in this invention; 0.22 microgram total protein loaded per well. The upper marker, system peak and lower marker bands represent external markers added from kit (0.24 microgram total protein per well). FIG. 9B shows the quantitation of protein bands from Protein LabChip electrophoresis.

FIG. 10A shows MS of conjugate with 3.6 DM1/Ab prepared using the method described in this invention shows a homogeneous conjugate with 1-6 DM1- bearing discrete conjugate peaks. FIG. 10B shows MS of conjugate with 4.0 DM1/Ab prepared by the traditional two-step conjugation method. The MS for the conjugate prepared by the traditional two-step method shows peaks corresponding to conjugates, and conjugates with hydrolyzed or cross-linked linkers (such as conjugate with 2 DM1, plus one L, 2 L, and 3 L), indicating a heterogeneous product.

FIG. 15A shows Protein LabChip electrophoresis under reducing condition (Agilent 2100 Bioanalyzer/Agilent Protein 230 kit) of Ab-SMCC-DM1 conjugates. Lane 1: molecular weight markers; lane 2: Ab-SMCC-DM1, 3.1 D/Ab, synthesized using the method described in this patent; lane 3: unconjugated Ab; lane 4: Ab-SMCC-DM1, 3.1 D/Ab, synthesized using the 2 step conjugation method; (0.24 microgram total protein in each lane). The upper marker, system peak and lower marker bands represent external markers added from kit. FIG. 15B shows the quantitation of protein bands from Protein LabChip electrophoresis.

FIG. 16A shows MS of conjugate prepared by the sequential two-step method with 3.1 DM1 per Ab. Each major conjugate peak has associated side peaks due to the presence of hydrolyzed and cross-linked linker fragments. FIG. 16B shows MS of conjugate prepared by the method described in this invention with 3.1 DM1 per Ab. Due to homogeneity of the conjugate, the MS peaks were well resolved.

DETAILED DESCRIPTION OF THE INVENTION

Figure 1:
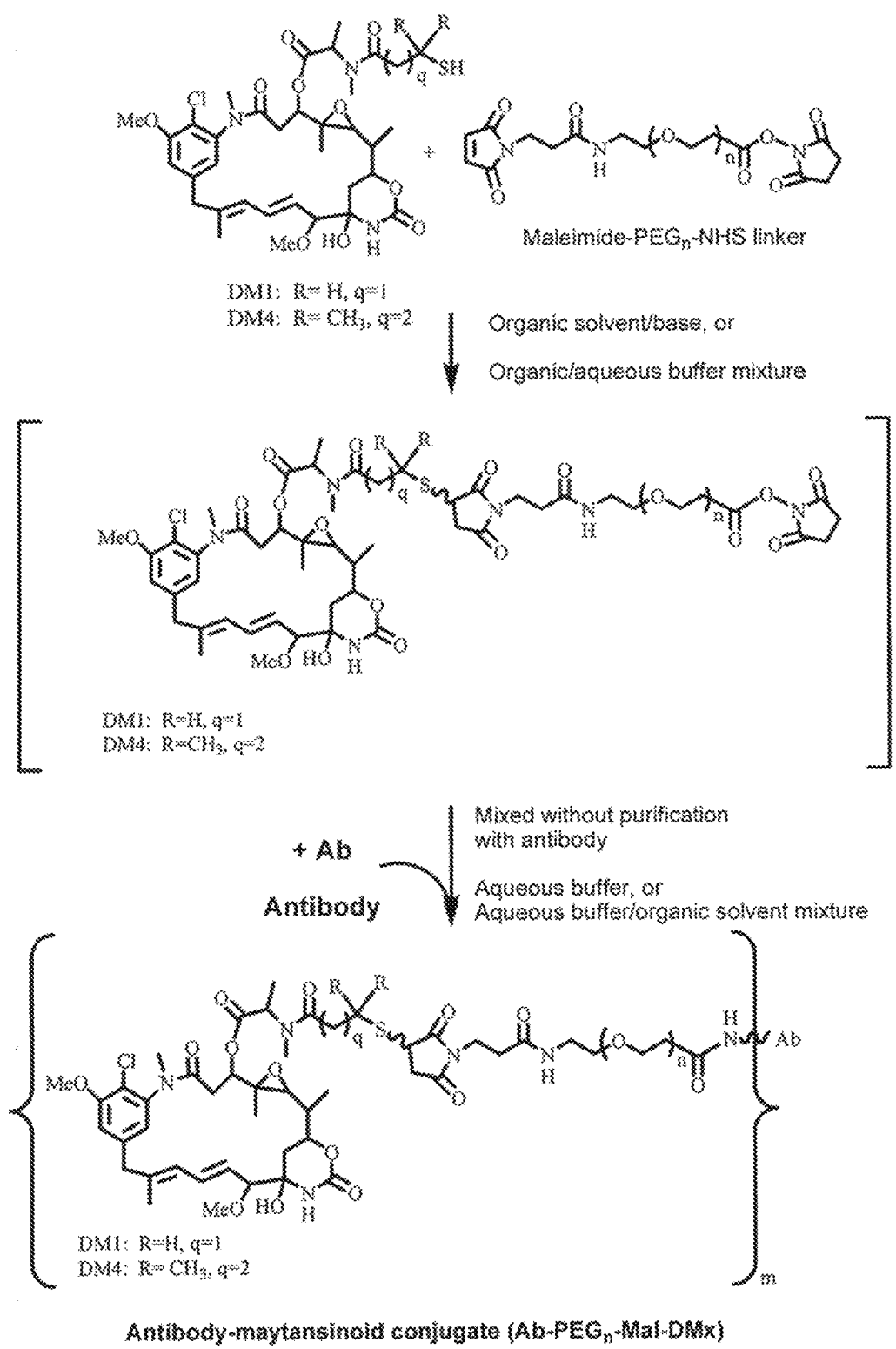
FIG. 1 shows conjugation of antibody with a reaction mixture of the maytansinoid DM1 (or DM4) and Maleimide-$PEG_n$-NHS linker

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

This invention describes a novel method of conjugating a thiol-containing effector (e.g., a cytotoxic agent) or a reporter group (e.g., a radiolabel) with a cell binding agent (e.g., an antibody), in which the thiol-group containing effector or reporter is first reacted with a bifunctional linker reagent in organic, aqueous, or mixed organic/aqueous solvent, followed by reaction of the unpurified reaction mixture with the cell binding agent in organic, aqueous or mixed organic/aqueous solvents.

Legend Abbreviations

Abbreviations which have been used in the descriptions of the Schemes and the Examples that follow are:

C=Effector or a reporter group (e.g., a cytotoxic agent or a radiolabel)

L=Linker (e.g., cleavable or a non-cleavable linker)

X=amine-reactive group (e.g., N-hydroxysuccinimide ester (NHS ester), sulfo-NHS ester, p-nitrophenol ester, tetrafluorosulfonate phenyl ester, 1-hydroxy-2-nitro-benzene-4-sulfonic acid ester)

Y=Maleimide, or haloacetamide (iodoacetamide, bromoacetamide)

$Y_b$ is a reactive mixed disulfide group (e.g., 2-pyridyldithio, 4-pyridyldithio, 2-nitro-pyridyldithio, 5-nitro-pyridyldithio, 2-carboxy-5-nitro-pyridyldithio)

X'=amide linkage

Y'=thioether (R—S—R') or selenoether (R—Se—R') linkage $Y_b$'=disulfide (R—S—S—R') linkage In one embodiment of this invention, a process for the preparation of a thioether-linked conjugate of a cell-binding agent with an effector or a reporter molecule is described, the process comprising the following steps: a) contacting a heterobifunctional linker of formula X-L-Y with a thiol-containing effector or reporter molecule C (e.g., a maytansinoid or a radionuclide) in aqueous solvent, organic solvent, or mixed organic/aqueous reaction mixtures which yields an intermediate product of formula X-L-Y'—C; b) mixing of the reaction mixture without purification with a cell-binding agent such as an antibody (Ab) to produce a conjugate of formula Ab-(X'-L-Y'—C)$_m$, wherein, L is a substituted or unsubstituted linear, branched or cyclic alkyl, alkenyl, or alkynyl group bearing from 1-10 carbon atoms, a simple or substituted aryl unit (substituents selected from alkyl, alkoxy, halogen, nitro, fluoro, carboxy, sulfonate, phosphate, amino, carbonyl, piperidino) or a polyethylene glycol containing unit (preferably 1-500 PEG spacer, or more preferably 1-24 PEG spacer, or still more preferably 2-8 PEG spacer); X and Y are amine or thiol-reactive group such as N-hydroxysuccinimide ester and maleimide or haloacetamide; Ab is an antibody; m is an integer from 1-20; X' is modified X site (e.g., an amide linkage) upon reaction with antibody; Y' is modified Y site (e.g., thioether linkage) upon reaction with, for example, a cytotoxic agent or a radiolabel of the effector or reporter group; and c) purification of the conjugate by tangential flow filtration, dialysis, or chromatography (e.g., gel filtration, ion-exchange chromatography, hydrophobic interaction chromatography) or a combination thereof. Preferably, Y is a thiol-reactive group selected from maleimide or haloacetamide. Preferably, L is a linear or branched alkyl group with 1-6 carbons or 2-8 PEG spacer. Preferably, C is a cytotoxic agent selected from a maytansinoid, a CC-1065 analog, a taxane, a DNA-binding agent, and more preferably it is a maytansinoid.

This reaction sequence represented in formulae 1 and 2:

(1)

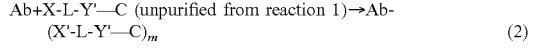
(2)

does not involve any purification of the intermediate product X-L-Y'—C, and therefore provides the advantage of directly mixing it with the antibody (the unpurified intermediate product is added to the antibody or, the antibody is added to the unpurified intermediate product) thereby making the method advantageous for conjugation because it eliminates the need of a cumbersome purification step. Importantly, this method yields homogeneous conjugate with no inter-chain protein cross-linking or inactivated maleimide residues, in contrast to the inter-chain protein cross-linking and inactivated maleimide residues observed in conjugates prepared by the traditional two step reaction and purification sequence.

The reaction 1 can be carried out at high concentrations of the heterobifunctional linker, X-L-Y, and the effector or reporter group C in aqueous solvent, organic solvent, or organic/aqueous reaction mixtures, resulting in faster reaction rates than at lower concentrations in aqueous solutions for conjugates prepared by the traditional two step reaction and purification sequence.

The intermediate product X-L-Y'—C generated in reaction 1 can be stored unpurified in a frozen state, at low temperatures in aqueous solvent at appropriate low pH (e.g., pH ~4-6), in organic solvents, or in mixed organic/aqueous mixtures, or in lyophilized state, for prolonged periods and can be mixed later with the antibody solution for the final conjugation reaction at a higher pH value of about 4-9, therefore adding to the convenience of this reaction sequence. The intermediate product can be diluted as required with organic solvent or with aqueous buffer, or a mixture of organic solvent and aqueous buffer prior to mixing with the cell binding agent. The term "about" as used herein in connection with a numerical should be understood to refer to all such numbers, including all numbers and small variations therefrom. The reaction of the intermediate product X-L-Y'—C with antibody can be carried out at pH values of about 4 to about pH 9, preferably in the pH range of about 5 to 8.7, more preferably, in the pH range of about 6.5 to about 8.5, such as, pH 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, and 8.5, a pH range therein or small variations therefrom. The buffers used for the reaction of the antibody with the intermediate product X-L-Y'—C in the preferential pH range of about 6.5 to 8.5 are buffers with pK$_a$ values around this pH range, such as phosphate and HEPES buffer. These preferred buffers should not have primary or secondary amino groups, or other reactive groups, that can react with linker X (such as N-hydroxysuccinimide ester).

A stoichiometric or a slight excess of C over the heterobifunctional linker X-L-Y is used in the first reaction to ensure that all Y group (such as maleimide) is reacted before the unpurified mixture is added to the antibody. An optional additional treatment with a quenching reagent (such as 4-maleimidobutyric acid, 3-maleimidopropionic acid, or N-ethylmaleimide, or iodoacetamide, or iodoacetamidopropionic acid) can be done to ensure that any unreacted C is quenched before mixing with the antibody to minimize any unwanted thiol-disulfide interchange reaction with the native antibody disulfide groups. Upon quenching with polar, charged thiol-quenching reagents (such as 4-maleimidobutyric acid or 3-maleimidopropionic acid), the excess, unreacted C is converted into a polar, charged adduct that can be easily separated from the covalently-linked conjugate. Optionally, the final reaction mixture 2, before purification, is treated with nucleophiles, such as amino group containing nucleophiles (e.g., lysine, taurine, hydroxylamine) to quench any unreacted linker (X-L-Y'—C).

An alternative method for the reaction of antibody with the unpurified initial reaction mixture of maytansinoids (DMx) and heterobifunctional linker involves mixing the initial reaction mixture of DMx and heterobifunctional linker (upon completion of the DMx-linker reaction) with antibody at low pH (pH ~5) followed by addition of buffer or base to increase the pH to about 6.5-8.5 for the conjugation reaction.

This new method is applied to the preparation of an antibody conjugate with the cytotoxic maytansinoid drug. The antibody-maytansinoid conjugates prepared using this method outlined in the reaction sequence 1-2 unexpectedly were much superior in homogeneity compared to the conjugates prepared by the traditional two step reaction and purification sequence, based on characterization of the conjugates by reducing SDS-PAGE, protein LabChip electrophoresis, and mass spectrometry. The conjugation method described in this invention that involves the reaction sequence 1-2 also does not require any intermediate purification step and is therefore significantly more convenient than the traditional two-step method.

In a second embodiment of the invention, a process for the preparation of a thioether-linked conjugate of a cell-binding agent with an effector or reporter molecule is described comprising the following steps: a) contacting a homobifunctional linker of formula Y-L-Y with a thiol- or amine-containing effector or reporter group C (such as a cytotoxic agent) in aqueous solvent, organic solvent, or mixed aqueous/organic reaction mixtures to yield Y-L-Y'—C, b) mixing of the reaction mixture without purification with an antibody in aqueous solution or aqueous/organic mixture to produce a conjugate of formula Ab-(Y'-L-Y'—C)$_m$, wherein, L is as defined above; Y is a thiol- or amine-reactive group such as a maleimide or haloacetamide, or N-hydroxysuccinimide or sulfo N-hydroxysuccinimide; Ab is an antibody; m is an integer from 1 to 20; Y' is the modified Y site (such as a thioether or amide linkage) upon reaction with antibody or a modified Y site (such as a thioether or amide linkage) upon reaction with the cytotoxic agent or effector or reporter group, and c) purification of the conjugate by tangential flow filtration, dialysis, or chromatography (gel filtration, ion-exchange chromatography, hydrophobic interaction chromatography) or a combination thereof. The reaction sequence represented in formulae 3 and 4:

  (3)

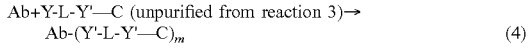  (4)

does not involve any purification of the intermediate product Y-L-Y'—C, and therefore is an advantageous method for conjugation.

In a third embodiment, a process for the preparation of a disulfide-linked conjugate of a cell binding agent with an effector or reporter molecule is described that comprises of the following steps: a) contacting a heterobifunctional linker of formula X-L-Y$_b$ with the effector or reporter group C (such as a cytotoxic agent) in aqueous solvent, organic solvent or mixed organic/aqueous reaction mixtures to yield intermediate product X-L-Y$_b$'—C; b) mixing of the reaction mixture without purification with the antibody in an aqueous solution or aqueous/organic mixture to produce a conjugate of formula Ab-(X'-L-Y$_b$'—C)$_m$, wherein, L is as described above; Y$_b$ is a reactive disulfide such as a pyridyl disulfide or a nitro-pyridyl disulfide; X is an amine-reactive group such as N-hydroxysuccinimide ester or sulfo N-hydroxysuccinimide ester; Ab is an antibody; m is an integer from 1 to 20; X' is modified X site (such as amide linkage) upon reaction with antibody; Y$_b$' is modified Y$_b$ site (disulfide) upon reaction with the cytotoxic agent or effector or reporter group; and c) purification of the conjugate by tangential flow filtration, dialysis, or chromatography (gel filtration, ion-exchange chromatography, hydrophobic interaction chromatography) or a combination thereof. The reaction sequence is represented in formulae 5 and 6:

  (5)

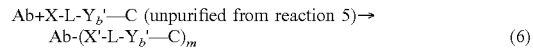  (6)

In a fourth embodiment, a process for the preparation of conjugates of antibody with effector or reporter groups with two types of linkers—non-cleavable (thioether linkage) and cleavable (disulfide linkage)—comprising the following steps is described: a) contacting X-L-Y and X-L-Y$_b$ linkers with the cytotoxic agent C to generate intermediate compounds of formulae X-L-Y'—C and X-L-Y$_b$'—C, b) mixing of the reaction mixtures without purification with the antibody either in a sequence or simultaneously as indicated in reaction formulae 7-9:

  (7)

  (8)

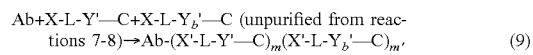  (9)

to provide a conjugate Ab-(X'-L-Y'—C)$_m$(X'-L-Y$_b$'—C)$_{m'}$, wherein, the definitions of X, L, Y', C, Y$_b$', and m are as given above, and m' is an integer from 1 to 20; and c) purification of the conjugate by tangential flow filtration, dialysis, or chromatography (gel filtration, ion-exchange chromatography, hydrophobic interaction chromatography) or a combination thereof. These two linker effector intermediates (X-L-Y'—C and X-L-Y$_b$'—C) are mixed without purification with the antibody in different sequences (first X-L-Y'—C then X-L-Y$_b$'—C, or first X-L-Y$_b$'—C then X-L-Y'—C or simultaneously) in various ratio.

The reactions 1, 3, 5, and 7-8, can be carried out at high concentrations of the bifunctional linker (X-L-Y, X-L-Y$_b$, or Y-L-Y) and the effector or reporter group C in aqueous solvent, organic solvent, or organic/aqueous reaction mixtures, resulting in faster reaction rates than at lower concentrations in aqueous solutions for conjugates prepared by the traditional two step reaction and purification sequence where the solubility of reagents is limiting.

The intermediate products X-L-Y'—C, or Y-L-Y'—C, or X-L-Y$_b$'—C generated in reactions 1, 3, 5, and 7-8 can be stored unpurified in a frozen state, at low temperatures in aqueous solvent at appropriate pH, in organic solvents, or in mixed organic/aqueous mixtures, or in lyophilized state, for prolonged periods and can be added later to the antibody solution for the final conjugation reaction, therefore adding to the convenience of this reaction sequence.

A stoichiometric or a slight excess of C over the heterobifunctional linker X-L-Y, or Y-L-Y, or X-L-Y$_b$ is used in the first reaction to ensure that all Y group (such as maleimide) is reacted before the unpurified mixture is added to the antibody. An optional additional treatment with a quenching reagent (such as 4-maleimidobutyric acid, or 3-maleimidopropionic acid, or N-ethylmaleimide, or iodoacetamide, or iodoacetic acid) can be done to ensure that any unreacted group (such as thiol) in C is quenched before the addition to the antibody to minimize any unwanted thiol-disulfide interchange reaction with the native antibody disulfide groups. The quenching of the excess C using a charged, polar thiol-quenching reagent, after the initial reaction of C with the bifunctional linker, converts excess C into a highly polar, water-soluble adduct that is easily separated from the covalently-linked conjugate by gel filtration, dialysis, or TFF.

The final conjugate product does not contain any non-covalently associated C. Optionally, the final reaction mixtures 2, 4, 6, and 9, before purification, are treated with nucleophiles, such as, amino group containing nucleophiles (e.g., lysine, taurine, hydroxylamine) to quench any unreacted linkers (X-L-Y'—C, Y-L-Y'—C, or X-L-$Y_b$'—C).

An alternate method of the reaction of antibody with the unpurified initial reaction mixture of DMx and bifunctional linker involves mixing the initial reaction mixture of DMx and bifunctional linker (upon completion of the DMx-linker reaction) with antibody at low pH (pH ~5) followed by addition of buffer or base to increase the pH to about 6.5-8.5 for the conjugation reaction.

Multiple copies of more than one type of effector can be conjugated to the antibody by adding two or more linker-effector intermediates derived from two or more different effectors, without purification, to the antibody either in a sequence or simultaneously.

Effector Group(s)

The terms Effector group or Effector molecule are used interchangeably and the term "Effector group(s)" or "Effector molecule(s)", as used herein, is meant to include cytotoxic agents. In certain respects, it may be desirable that the effector groups or molecules are attached by spacer arms of various lengths to reduce potential steric hindrance. Multiple copies of more than one type of effector can be conjugated to the antibody by adding two or more linker-effector intermediates derived from two or more different effectors, without purification, to the antibody either in a sequence or simultaneously.

Cytotoxic agents that can be used in the present invention include chemotherapeutic agents or structural analogues of chemotherapeutic agents. "Chemotherapeutic agent" is a chemical compound useful in the treatment of cancer. Examples of chemotherapeutic agents include alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimnidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA and pharmaceutically acceptable salts, acids or derivatives of any of the above. Other chemotherapeutic agents that can be used with the present invention are disclosed in US Publication No. 20080171040 or US Publication No. 20080305044 and are incorporated in their entirety by reference.

In a preferred embodiment, chemotherapeutic cytotoxic agents are essentially small molecule cytotoxic agents. A "small molecule drug" is broadly used herein to refer to an organic, inorganic, or organometallic compound that may have a molecular weight of for example 100 to 1500, more suitably from 120 to 1200, favorably from 200 to 1000, and typically having a molecular weight of less than about 1000. Small molecule cytotoxic agents of the invention encompass oligopeptides and other biomolecules having a molecular weight of less than about 1000. Small molecule cytotoxic agents are well characterized in the art, such as in WO05058367A2, European Patent Application Nos. 85901495 and 8590319, and in U.S. Pat. No. 4,956,303, among others and are incorporated in their entirety by reference.

Preferable small molecule cytotoxic agents are those that allow for linkage to the cell-binding agent. The invention includes known cytotoxic agents as well as those that may become known. Especially preferred small molecule cytotoxic agents include cytotoxic agents.

The cytotoxic agent may be any compound that results in the death of a cell, or induces cell death, or in some manner decreases cell viability, wherein each cytotoxic agent comprises a thiol moiety.

Preferred cytotoxic agents are maytansinoid compounds, taxane compounds, CC-1065 compounds, daunorubicin compounds and doxorubicin compounds, pyrrolobenzodiazepine dimers, calicheamicins, auristatins and analogues and derivatives thereof, some of which are described below.

Other cytotoxic agents, which are not necessarily small molecules, such as siRNA, are also encompassed within the scope of the instant invention. For example, siRNAs can be linked to the crosslinkers of the present invention by methods commonly used for the modification of oligonucleotides (see, for example, US Patent Publications 20050107325 and 20070213292). Thus the siRNA in its 3' or 5'-phosphoromidite form is reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine. siRNA are described in detail in U.S. Patent Publication Numbers: 20070275465, 20070213292, 20070185050, 20070161595, 20070054279, 20060287260, 20060035254, 20060008822, 20050288244, 20050176667, which are incorporated herein in their entirety by reference.

Maytansinoids

Maytansinoids that can be used in the present invention are well known in the art and can be isolated from natural sources according to known methods or prepared synthetically according to known methods.

Examples of suitable maytansinoids include maytansinol and maytansinol analogues. Examples of suitable maytansinol analogues include those having a modified aromatic ring and those having modifications at other positions.

Specific examples of suitable analogues of maytansinol having a modified aromatic ring include:

(1) C-19-dechloro (U.S. Pat. No. 4,256,746) (prepared by LAH reduction of ansamitocin P2);

(2) C-20-hydroxy (or C-20-demethyl)+/–C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/–dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with H2S or P2S5);

(2) C-14-alkoxymethyl (demethoxy/CH2OR) (U.S. Pat. No. 4,331,598);

(3) C-14-hydroxymethyl or acyloxymethyl (CH2OH or CH2OAc) (U.S. Pat. No. 4,450,254) (prepared from *Nocardia*);

(4) C-15-hydroxy/acyloxy (U.S. Pat. No. 4,364,866) (prepared by the conversion of maytansinol by *Streptomyces*);

(5) C-15-methoxy (U.S. Pat. Nos. 4,313,946 and 4,315,929) (isolated from *Trewia nudiflora*);

(6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

The synthesis of thiol-containing maytansinoids useful in the present invention is fully disclosed in U.S. Pat. Nos. 5,208,020, 5,416,064, and U. S. Patent Application No. 20040235840.

Maytansinoids with a thiol moiety at the C-3 position, the C-14 position, the C-15 position or the C-20 position are all expected to be useful. The C-3 position is preferred and the C-3 position of maytansinol is especially preferred. Also preferred are an N-methyl-alanine-containing C-3 thiol moiety maytansinoid, and an N-methyl-cysteine-containing C-3 thiol moiety maytansinoid, and analogues of each.

Specific examples of N-methyl-alanine-containing C-3 thiol moiety maytansinoid derivatives useful in the present invention are represented by the formulae M1, M2, M3, M6 and M7.

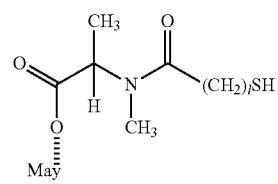

M1 wherein:

l is an integer of from 1 to 10; and

May is a maytansinoid.

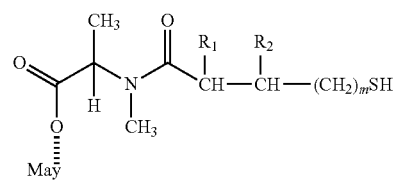

M2 wherein:

$R_1$ and $R_2$ are H, $CH_3$ or $CH_2CH_3$, and may be the same or different;

m is 0, 1, 2 or 3; and

May is a maytansinoid.

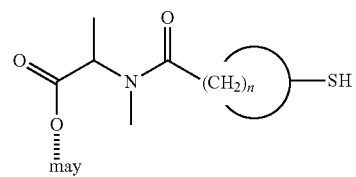

M3 wherein:

n is an integer of from 3 to 8; and

May is a maytansinoid.

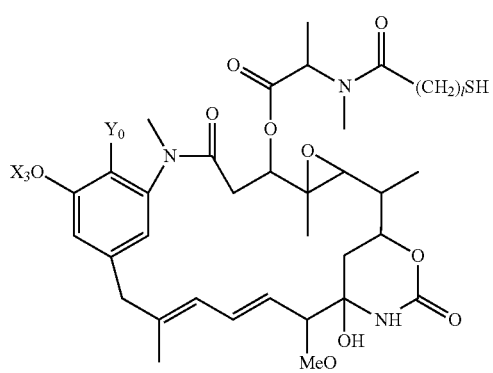

M6

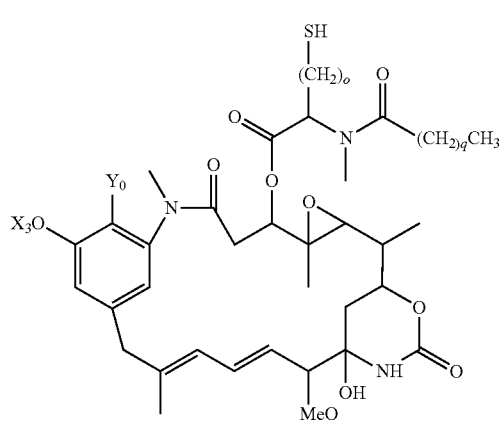

M5 wherein:

l is 1, 2 or 3;

$Y_0$ is Cl or H; and $X_3$ is H or $CH_3$.

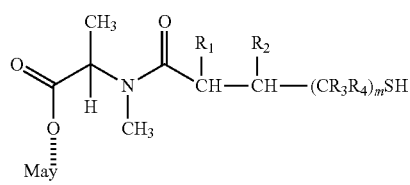

M7 wherein:

$R_1$, $R_2$, $R_3$, $R_4$ are H, $CH_3$ or $CH_2CH_3$, and may be the same or different;

m is 0, 1, 2 or 3; and

May is a maytansinoid.

Specific examples of N-methyl-cysteine-containing C-3 thiol moiety maytansinoid derivatives useful in the present invention are represented by the formulae M4 and M5.

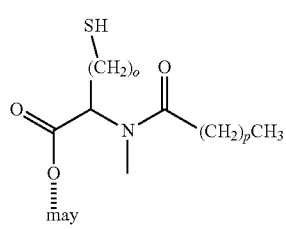

M4 wherein:

o is 1, 2 or 3;

p is an integer of 0 to 10; and

May is a maytansinoid.

wherein:

o is 1, 2 or 3;

q is an integer of from 0 to 10;

$Y_0$ is Cl or H; and $X_3$ is H or $CH_3$.

Preferred maytansinoids are those described in U.S. Pat. Nos. 5,208,020; 5,416,064; 6,333.410; 6,441,163; 6,716, 821; RE39,151 and 7,276,497.

Taxanes

The cytotoxic agent according to the present invention may also be a taxane.

Taxanes that can be used in the present invention have been modified to contain a thiol moiety. Some taxanes useful in the present invention have the formula T1 shown below:

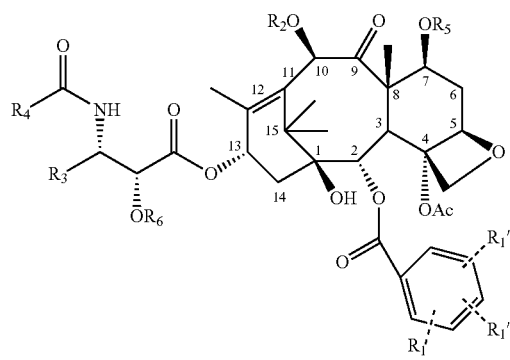

T1

Preferred taxoids are those described in U.S. Pat. Nos. 6,340,701; 6,372,738; 6,436,931; 6,596,757; 6,706,708; 7,008,942; 7,217,819 and 7,276,499.

CC-1065 Analogues

The cytotoxic agent according to the present invention may also be a CC-1065 analogue.

According to the present invention, the CC-1065 analogues contain an A subunit and a B or a B-C subunit. Preferred CC-1065 analogs are those described in U.S. Pat. Nos. 5,475,092; 5,595,499; 5,846,545; 6,534,660; 6,586, 618; 6,756,397 and 7,049,316.

Daunorubicin/Doxorubicin Analogues

The cytotoxic agent according to the present invention may also be a daunorubicin analogue or a doxorubicin analogue.

The daunorubicin and doxorubicin analogues of the present invention can be modified to comprise a thiol moiety. The modified doxorubicin/daunorubicin analogues of the present invention, which have a thiol moiety, are described in WO 01/38318. The modified doxorubicin/daunorubicin analogues can be synthesized according to known methods (see, e.g., U.S. Pat. No. 5,146,064).

Auristatin include auristatin E, auristatin EB (AEB), auristatin EFP (AEFP), monomethyl auristatin E (MMAE) and are described in U.S. Pat. No. 5,635,483, *Int. J. Oncol.* 15:367-72 (1999); Molecular Cancer Therapeutics, vol. 3, No. 8, pp. 921-932 (2004); U.S. application Ser. No. 11/134,826. U.S. Patent Publication Nos. 20060074008, 2006022925.

The cytotoxic agents according to the present invention include pyrrolobenzodiazepine dimers that are known in the art (U.S. Pat. Nos. 7,049,311; 7,067,511; 6,951,853; 7,189,710; 6,884,799; 6,660,856).

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

Reporter Group(s)

The terms Reporter group or Reporter molecule are used interchangeably and the term "Reporter group(s)" or "Reporter molecule(s)", as used herein, refers to a substance which is delivered to the specific substance or cells by the specific affinity portion of the reagent, for a diagnostic or therapeutic purpose; examples are radioisotopes, paramagnetic contrast agents, and anti-cancer agents. Various labels or reporter groups are useful for tumor-imaging applications in cancer patients, immunoassay applications for diagnosis of various diseases, cancer therapy using radioactive nuclide-ligand conjugates, and affinity chromatography applications for purification of bioactive agents such as proteins, peptides, and oligonucleides. The labels or reporter groups that are conjugated with cell-binding agents include fluorophores, and affinity labels such as biotin. Such reporter group references can be found in US publication number 2007/0092940. Reporter groups including, for example, biotin or fluorescein can also be attached to a PEG conjugate moiety. A number of suitable reporter groups are known in the art, e.g., U.S. Pat. No. 4,152,411 and Hirschfeld U.S. Pat. Nos. 4,166,105, 5,223,242, 5,501,952, US publication 20090136940 and are incorporated in their entirety by reference.

Linkers

The conjugates may be prepared by in vitro methods. In order to link a drug to the cell-binding agent, a linking group is used. Suitable linking groups are well known in the art and include non-cleavable or cleavable linkers. A non-cleavable linker is any chemical moiety that is capable of linking a cytotoxic agent to a cell-binding agent in a stable, covalent manner. Non-cleavable linkers are substantially resistant to acid-induced cleavage, light-induced cleavage, peptidase-induced cleavage, esterase-induced cleavage, and disulfide bond cleavage. Examples of non-cleavable linkers include linkers having an N-succinimidyl ester, N-sulfosuccinimidyl ester moiety, maleimido- or haloacetyl-based moiety for reaction with the drug, the reporter group or the cell binding agent. Crosslinking reagents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

Other crosslinking reagents lacking a sulfur atom that form non-cleavable linkers can also be used in the inventive method. Such linkers can be derived from dicarboxylic acid based moieties. Suitable dicarboxylic acid based moieties include, but are not limited to, α,ω-dicarboxylic acids of the general formula shown below:

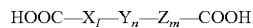

$$\text{HOOC}-X_l-Y_n-Z_m-\text{COOH}$$

wherein X is a linear or branched alkyl, alkenyl, or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms, or a substituted or unsubstituted heterocyclic group wherein the hetero atom is selected from N, O or S, and wherein l, m, and n are each 0 or 1, provided that l, m, and n are all not zero at the same time.

Many of the non-cleavable linkers disclosed herein are described in detail in U.S. Patent publication number 20050169933.

Cleavable linkers are linkers that can be cleaved under mild conditions, i.e. conditions under which the activity of the cytotoxic agent is not affected. Many known linkers fall in this category and are described below.

Acid-labile linkers are linkers cleavable at acid pH. For example, certain intracellular compartments, such as endosomes and lysosomes, have an acidic pH (pH 4-5), and provide conditions suitable to cleave acid-labile linkers.

Linkers that are photo-labile are useful at the body surface and in many body cavities that are accessible to light. Furthermore, infrared light can penetrate tissue.

Some linkers can be cleaved by peptidases. Only certain peptides are readily cleaved inside or outside cells, see e.g. Trouet et al., 79 Proc. Natl. Acad. Sci. USA, 626-629 (1982), Umemoto et al. 43 Int. J. Cancer, 677-684 (1989), and lysosomal-hydrolase cleavable valine-citrulline linkage (U.S. Pat. No. 6,214,345 B1). Furthermore, peptides are composed of .alpha.-amino acids and peptidic bonds, which chemically are amide bonds between the carboxylate of one amino acid and the .alpha.-amino group of a second amino acid. Other amide bonds, such as the bond between a carboxylate and the .epsilon.-amino group of lysine, are understood not to be peptidic bonds and are considered non-cleavable.

Some linkers can be cleaved by esterases. Again only certain esters can be cleaved by esterases present inside or outside cells. Esters are formed by the condensation of a carboxylic acid and an alcohol. Simple esters are esters produced with simple alcohols, such as aliphatic alcohols, and small cyclic and small aromatic alcohols. For example, the present inventors found no esterase that cleaved the ester at C-3 of maytansine, since the alcohol component of the ester, maytansinol, is very large and complex.

Preferred cleavable linker molecules include, for example, N-succinimidyl 3-(2-pyridyldithio)propionate (SPDP) (see, e.g., Carlsson et al., *Biochem. J.,* 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), and other reactive cross-linkers, such as those described in U.S. Pat. No. 6,913,748, which is incorporated herein in its entirety by reference.

Other linkers which can be used in the present invention include charged linkers or hydrophilic linkers and are described in U.S. patent application Ser. Nos. 12/433,604 and 12/433,668, respectively, which are incorporated herein in its entirety by reference.

Cell Binding Agents

The cell-binding agents used in this invention are proteins (e.g., immunoglobulin and non-immunoglobulin proteins) which bind specifically to target antigens on cancer cells. These cell-binding agents include:

antibodies including:
    resurfaced antibodies (U.S. Pat. No. 5,639,641);
    humanized or fully human antibodies (Humanized or fully human antibodies are selected from, but not limited to, huMy9-6, huB4, huC242, huN901, DS6, CD38, IGF-IR, CNTO 95, B—B4, trastuzumab, bivatuzumab, sibrotuzumab, and rituximab (see, e.g., U.S. Pat. Nos. 5,639,641, 5,665,357, and 7,342,110, International Patent Application WO 02/16,401, U.S. publication number 20060045877, U.S. publication number 20060127407, U.S. publication number 20050118183, Pedersen et al., (1994) *J. Mol. Biol.* 235, 959-973, Roguska et al., (1994) *Proceedings of the National Academy of Sciences*, Vol 91, 969-973, Colomer et al., *Cancer Invest.*, 19: 49-56 (2001), Heider et al., *Eur. J. Cancer*, 31A: 2385-2391 (1995), Welt et al., *J. Clin. Oncol.*, 12: 1193-1203 (1994), and Maloney et al., *Blood*, 90: 2188-2195 (1997)); and
    fragments of antibodies such as sFv, Fab, Fab', and F(ab')$_2$ that preferentially bind to a target cell (Parham, *J. Immunol.* 131:2895-2902 (1983); Spring et al, *J. Immunol.* 113:470-478 (1974); Nisonoff et al, *Arch. Biochem. Biophys.* 89:230-244 (1960));

Additional cell-binding agents include other cell binding proteins and polypeptides exemplified by, but not limited to:

Ankyrin repeat proteins (DARPins; Zahnd et al., J. Biol. Chem., 281, 46, 35167-35175, (2006); Binz, H. K., Amstutz, P. & Pluckthun, A. (2005) Nature Biotechnology, 23, 1257-1268) or ankyrin-like repeats proteins or synthetic peptides described, for example, in U.S. publication number 20070238667; U.S. Pat. No. 7,101,675; WO/2007/147213; WO/2007/062466);
  interferons (e.g. α, β, γ);
  lymphokines such as IL-2, IL-3, IL-4, IL-6;
  hormones such as insulin, TRH (thyrotropin releasing hormones), MSH (melanocyte-stimulating hormone), steroid hormones, such as androgens and estrogens; and
  growth factors and colony-stimulating factors such as EGF, TGF-α, IGF-1, G-CSF, M-CSF and GM-CSF (Burgess, *Immunology Today* 5:155-158 (1984)).

Where the cell binding agent is an antibody it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-beta1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins such as CD11a, CD11b, CD11c, CD18, an ICAM, VLA-4 and VCAM, alpha-V subunit of a heterodimeric human integrin receptor; a tumor associated antigen such as HER2, HER3 or HER4 receptor; and fragments of any of the above-listed polypeptides.

Preferred antigens for antibodies encompassed by the present invention include CD proteins such as CD3, CD4, CD8, CD19, CD20, CD34, and CD46; members of the ErbB receptor family such as the EGF receptor, HER2, HER3 or HER4 receptor; cell adhesion molecules such as LFA-1, Mac1, p 150.95, VLA-4, ICAM-1, VCAM, alpha4/beta7 integrin, and alpha v/beta3 integrin including either alpha or beta subunits thereof (e.g. anti-CD11a, anti-CD18 or anti-CD11b antibodies); growth factors such as VEGF; tissue factor (TF); TGF-β; alpha interferon (alpha-IFN); an interleukin, such as IL-8; IgE; blood group antigens Apo2, death receptor; flk2/flt3 receptor; obesity (OB) receptor; mpl receptor; CTLA-4; protein C etc. The most preferred targets herein are IGF-IR, CanAg, EGF-R, EphA2, MUC1, MUC16, VEGF, TF, CD19, CD20, CD22, CD33, CD37, CD38, CD40, CD44, CD56, CD138, CA6, Her2/neu, CRIPTO (a protein produced at elevated levels in a majority of human breast cancer cells), alpha v/beta3 integrin, alpha v/beta5 integrin, TGF-β, CD11a, CD18, Apo2 and C24.

Monoclonal antibody techniques allow for the production of specific cell-binding agents in the form of monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of sFv (single chain variable region), specifically human sFv (see, e.g., Griffiths et al, U.S. Pat. No. 5,885,793; McCafferty et al, WO 92/01047; Liming et al, WO 99/06587.)

Selection of the appropriate cell-binding agent is a matter of choice that depends upon the particular cell population that is to be targeted, but in general monoclonal antibodies and fragments thereof that preferentially bind to a target cell are preferred, if an appropriate one is available.

For example, the monoclonal antibody My9 is a murine $IgG_{2a}$ antibody that is specific for the CD33 antigen found on Acute Myeloid Leukemia (AML) cells (Roy et al. *Blood* 77:2404-2412 (1991)) and can be used to treat AML patients. Similarly, the monoclonal antibody anti-B4 is a murine $IgG_1$, that binds to the CD19 antigen on B cells (Nadler et al, *J. Immunol.* 131:244-250 (1983)) and can be used if the target cells are B cells or diseased cells that express this antigen such as in non-Hodgkin's lymphoma or chronic lymphoblastic leukemia. Similarly, the antibody N901 is a murine monoclonal $IgG_1$ antibody that binds to CD56 found on small cell lung carcinoma cells and on cells of other tumors of neuroendocrine origin (Roy et al. *J. Nat. Cancer Inst.* 88:1136-1145 (1996)), huC242 antibody that binds to the CanAg antigen, Trastuzumab that binds to HER2/neu, and anti-EGF receptor antibody that binds to EGF receptor.

Purification Methods

The conjugate, i.e., the finalized product, of the present invention is purified to remove any unreacted or unconjugated effector or reporter molecule, or unreacted linker or unconjugated, hydrolyzed linker. The purification method can be a tangential flow filtration (TFF, also known as cross flow filtration, ultrafiltration, or diafiltration), gel filtration, adsorptive chromatography, selective precipitation, or combinations thereof. The adsorptive chromatography methods include ion-exchange chromatography, hydroxyapatite chromatography, hydrophobic interaction chromatography (HIC), hydrophobic charge induction chromatography (HCIC), mixed mode ion exchange chromatography, immobilized metal affinity chromatography (IMAC), dye ligand chromatography, affinity chromatography, and reversed phase chromatography. For example, the conjugate Ab-(X'-L-Y'—C)$_m$ described in formula 2 is purified from unreacted C or unreacted/hydrolyzed linker X-L-Y or X-L-Y'—C. Similarly, the conjugates described in formulae 4, 6, and 9 are purified. Such methods of purification are known to one of skill in the art and can be found, for example, in US Publication No. 2007/0048314.

Undesired Hydrolyzed Linker or Protein Cross-Linking in Conjugates

Traditional conjugation methods employing the initial reaction of a protein with a heterobifunctional linker with reactive maleimide or haloacetamide residue suffer from two major drawbacks: (i) the conjugate product may consist of hydrolyzed linker, due to aqueous inactivation of the incorporated linker in the antibody before reaction with the effector or reporter molecule; and (ii) inter- or intrachain cross-linking of conjugate, due to reaction of maleimide (or haloacetamide) group with the native histidine, lysine, tyrosine, or cysteine residues in protein or peptide (A. Papini et al., *Int. J. Pept. Protein Res.*, 1992, 39, 348-355; T. Ueda et al., *Biochemistry*, 1985, 24, 6316-6322). Such interchain cross-linking in antibody would result in various non-reducible covalent linkages between the heavy and light chains, or between two heavy chains, which would be apparent in reducing SDS-PAGE analysis as bands of higher molecular weights than the expected heavy and light chain bands. Such interchain or intrachain cross-linking in antibody would also be apparent by MS as peaks of aberrant masses different than the expected masses of antibody plus linked reporter or effector groups. Unlike traditional conjugation methods, the method described in this application results in conjugates with high homogeneity with no substantial interchain cross-linking or hydrolyzed linker.

All references cited herein and in the examples that follow are expressly incorporated by reference in their entireties.

EXAMPLES

The following examples, which are illustrative only, are not intended to limit the present invention.

Example 1. Conjugation of Antibody with Cytotoxic Agent DM1/DM4 Using Heterobifunctional Linker Maleimide-PEG$_n$-NHS by this Method (FIG. 1) Versus Traditional Two-Step Method Stock solutions of DM1 [$N^{2'}$-deacetyl-$N^{2'}$-(3-mercapto-1-oxopropyl)-maytansine], or DM4 [$N^{2'}$-deacetyl-$N^{2'}$-(4-mercapto-4-methyl-1-oxopentyl)maytansine] (DMx) thiol and the Maleimide-PEG$_n$-NHS bifunctional linker were made up in N,N-dimethylacetamide (DMA) at concentrations of 30-60 mM. The linker and DMx thiol were mixed together in DMA containing up to 50% v/v of 200 mM succinate buffer, 2 mM EDTA, pH 5.0 to give a molar ratio of DMx to linker of 1.6:1 and a final concentration of DMx equal to 15 mM. After mixing, the reaction mixture was left for 1-4 h and then an aliquot of the reaction mixture was diluted 10 fold and its absorbance measured at 302-320 nm to determine the presence of any remaining unreacted maleimide using the extinction coefficient ($\epsilon$) of maleimide at 302 nm=620 $M^{-1}$ $cm^{-1}$, and $\epsilon$320 nm~450 $M^{-1}$ $cm^{-1}$. (Additional reverse phase HPLC analysis of a frozen aliquot of the reaction mixture was carried out later with absorbance monitoring at 302 nm and 252 nm to verify complete disappearance of linker maleimide and formation of the desired linker-DMx reagent at the time of addition of the reaction mixture to antibody). When no further maleimide was present by UV, an aliquot of the reaction mixture was added without purification to a solution of antibody in phosphate buffer (pH 7.5) under final conjugation conditions of 4 mg/ml Ab, 90% phosphate buffer/10% DMA, pH 7.5. The conjugation reaction was allowed to proceed at ambient temperature for 2 h. Ab-DMx conjugate was purified from the excess small-molecule DMx and linker reactants using a G25 gel filtration column equilibrated in pH 7.5 phosphate buffer, or using tangential flow filtration (TFF). The conjugation mixture was further kept at 4° C. for 2 days in pH 7.5 buffer to allow the dissociation of any DMx species attached to antibody non-covalently or via labile linkage. The conjugate was then dialyzed overnight into pH 5.5 histidine/glycine buffer and then filtered through a 0.22 μm filter for final storage. The number of DMx molecule per Ab molecule (average) in the final conjugate was measured by determining absorbance of the conjugate at 252 and 280 nm and using known extinction coefficients for DMx and antibody at these two wavelengths.

Several different reaction conditions were used for the initial reaction of DMx thiol with the heterobifunctional maleimide-PEG$_4$-NHS reagent: 50% DMA/50% aqueous 200 mM succinate buffer pH 5.0, 2 mM EDTA (v/v); or 60% DMA/40% 200 mM succinate buffer pH 5.0, 2 mM EDTA (v/v); or 100% DMA with 1.5 molar equivalents of an organic base (for example N,N'-diisopropyl ethylamine, DIPEA, or 4-methylmorpholine) per mol DM4 thiol.

In one series of experiments, the molar equivalent of DMx to maleimide-PEG$_4$-NHS linker (purchased from Pierce Endogen) was varied from 1.2-2.4, and the reaction time was 30 min. The number of DMx/Ab measured on purified conjugates were measured as a function of added equivalents of DMx per linker. Conditions of 1.2-2.0 equivalents of DM1/Linker gave conjugates with similar DMx/Ab loads, indicating that the undesired reaction of the DMx thiol at the NHS ester side of the linker is not a significant problem. The amount of cross-linking present in the final conjugates was also analyzed by reducing SDS PAGE showing that the presence of cross-linked contaminants decreases significantly with increasing DM1/linker ratio.

One optional quenching step using maleimide or haloacetamide reagents (such as maleimidobutyric acid, or maleimidopropionic acid, or N-ethylmaleimide, or iodoacetamide, or iodoacetic acid) was introduced after the completion of the initial DMx and heterobifunctional linker reaction (before the addition of the reaction mixture to the antibody) to quench the excess DMx thiol group in order to prevent any unwanted reaction of DMx thiol with the antibody.

An alternate method of the reaction of antibody with the unpurified initial reaction mixture of DMx and heterobifunctional linker involved mixing the initial reaction mixture of DMx and heterobifunctional linker (upon completion of the DMx-linker reaction) with antibody at low pH (pH ~5) followed by the addition of buffer or base to increase the pH to 6.5-8.5 for the conjugation reaction.

An antibody-PEG$_4$-Mal-DM1 or DM4 conjugate was made by the traditional two step conjugation method for comparison with the conjugation method described in this invention. The humanized antibody at a concentration of 8 mg/ml in pH 7.5 phosphate buffer (50 mM potassium phosphate, 50 mM sodium chloride, 2 mM EDTA, pH 7.5) and 5% DMA was modified with excess heterobifunctional maleimide-PEG$_4$-NHS linker reagent (purchased from Pierce Endogen). After 2 h at 25° C., the modified antibody was gel purified by G25 chromatography to remove excess unreacted, unincorporated linker. The recovery of purified Ab was determined by UV absorbance at 280 nm. The number of linked maleimide groups in the modified Ab was determined using a small aliquot of modified antibody by addition of a known amount of thiol (such as 2-mercaptoethanol), added in excess over the maleimide, to react with the maleimide residues in the modified antibody and then assaying the remaining thiol by Ellman's assay using DTNB reagent (extinction coefficient of TNB thiolate at 412 nm=14150 M$^{-1}$ cm$^{-1}$; Riddles, P. W. et al., Methods Enzymol., 1983, 91, 49-60; Singh, R., Bioconjugate Chem., 1994, 5, 348-351). The conjugation of modified Ab with DM1 or DM4 thiol was carried out at an Ab concentration of 2.5 mg/ml in a reaction mixture consisting of 95% phosphate buffer pH 7.5 (50 mM potassium phosphate, 50 mM sodium chloride, 2 mM EDTA, pH 7.5) and 5% DMA. An excess of 1.7 molar equivalents of DM1 or DM4 thiol was added per mol of linked maleimide on the Ab. After reacting overnight at 25° C., the conjugate was sterile filtered using a 0.22 μm filter and gel purified from excess unreacted DM1 or DM4 by a G25 column equilibrated in phosphate buffer pH 7.5 (50 mM potassium phosphate, 50 mM sodium chloride, 2 mM EDTA, pH 7.5). The purified conjugate was held at 4° C. for 2 days in phosphate buffer pH 7.5 (50 mM potassium phosphate, 50 mM sodium chloride, 2 mM EDTA, pH 7.5) to allow for the dissociation of any DM1 or DM4 species attached to antibody non-covalently or via a labile linkage. The conjugate was subsequently dialyzed for 2 days in histidine/glycine buffer pH 5.5 (130 mM glycine/10 mM histidine, pH 5.5) and sterile filtered using a 0.22 μm filter. The number of DM1 or DM4 molecules per Ab molecule in the final conjugate was measured by determining absorbance of the conjugate at 252 and 280 nm using known extinction coefficients for DM1/DM4 and Ab at these two wavelengths.

Figure 2:
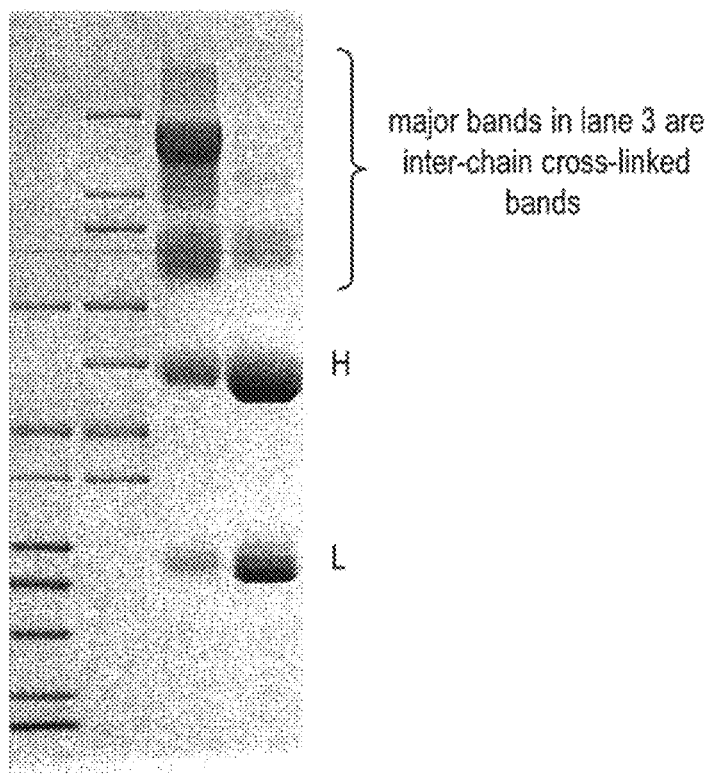
FIG. 2 shows reducing SDS-PAGE of Ab-($PEG_4$-Mal)-DM4 conjugates prepared using the method described in this invention versus conjugates prepared using the traditional 2-step method. Each sample lane contained 10 µg protein; the gel was stained with Coomassie Blue. Lanes 1 and 2 contained molecular weight markers. Lane 3 contained conjugate prepared by the traditional two-step method with 6.1 DM4 per Ab. Lane 4 contained conjugate prepared by the method described in this invention and contained 6.2 DM4 per Ab.

Reducing SDS PAGE was carried out on conjugate and antibody samples using the NuPage electrophoresis system with a 4-12% Bis Tris Gel (Invitrogen). Heat denatured and reduced samples were loaded at 10 μg/lane. The reducing SDS-PAGE of the conjugates prepared using the method described in this invention showed only the expected heavy and light chain bands (50 kDa and 25 kDa respectively) as the major bands (FIG. 2). In contrast, the conjugates prepared by the traditional two-step conjugation method showed undesired cross-linked bands with molecular weights of 75, 100, 125, and 150 kDa, presumably corresponding to inter-chain cross-linked species HL, H$_2$, H$_2$L, and H$_2$L$_2$ respectively (FIG. 2).

Figures 3A, 3B:
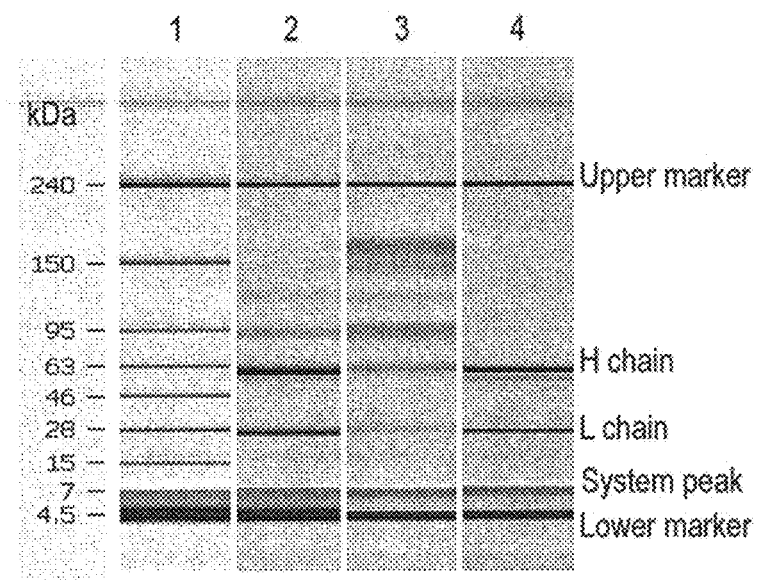
FIGS. 3A-B show Protein LabChip electrophoresis of Ab-($PEG_4$-Mal)-DM4 conjugates prepared using the method described in this invention versus conjugates prepared using the traditional 2-step method.

Protein LabChip electrophoresis analysis (under reducing condition) of the antibody-PEG$_4$-Mal-DM4 conjugate prepared by the method described in this invention showed the expected heavy and light chain bands with percentages of 58 and 30% (of total protein), which are similar to those for unconjugated antibody of 65 and 30% respectively (FIGS. 3A-B). In contrast, the conjugate prepared using the traditional two-step conjugation method showed heavy and light bands of only 16 and 8% respectively, and major bands of higher molecular weights ranging from 94-169 kDa presumably due to inter-chain cross-linking (FIGS. 3A-B). Based on the quantitative Protein LabChip analysis, the conjugate prepared by the method described in this application is highly superior to that prepared using the conventional two-step process.

Figure 4A:
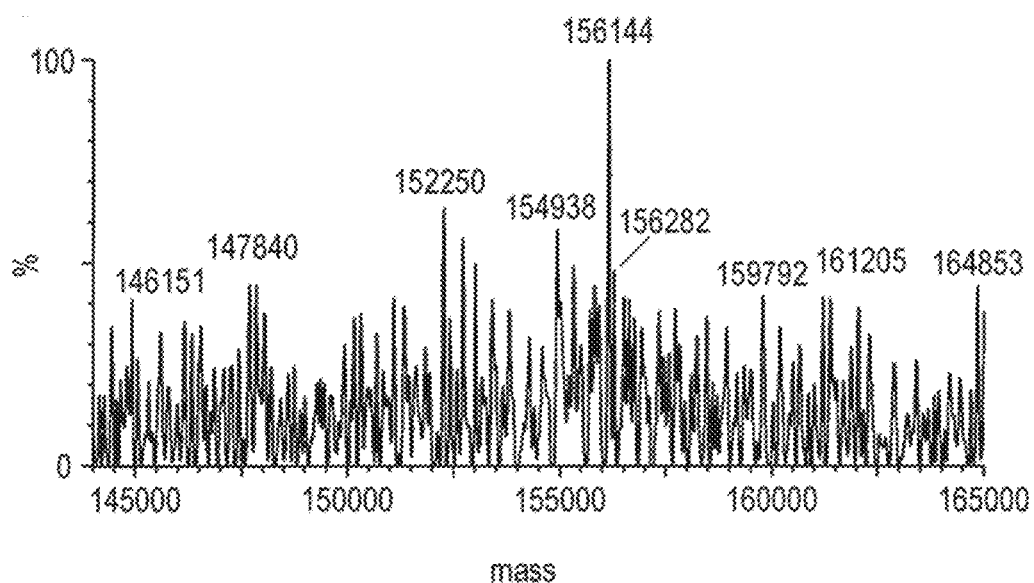
FIGS. 4A-B show MS of Ab-($PEG_4$-Mal)-DM4 conjugates prepared using the method described in this invention versus conjugates prepared using the traditional 2-step method.
Figure 4B:
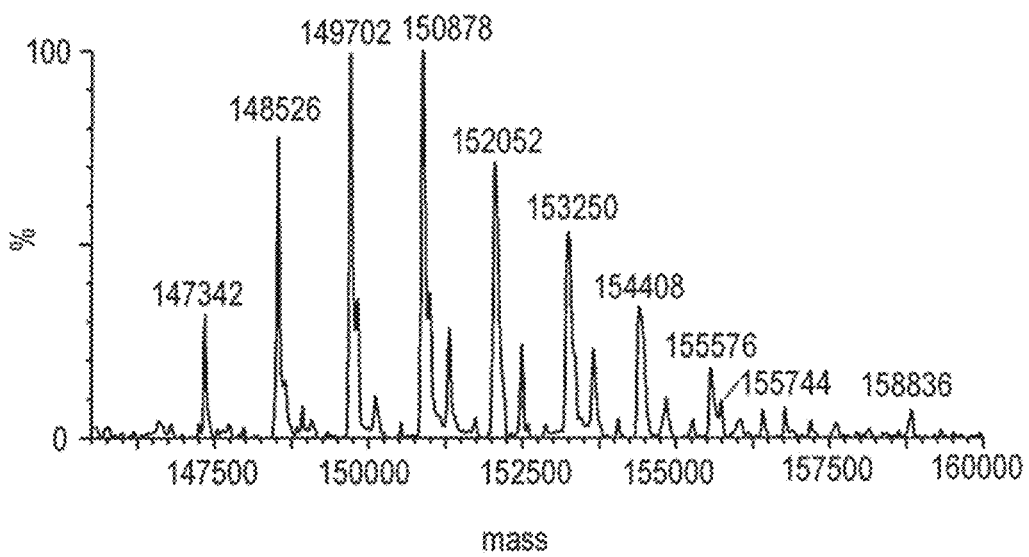

The MS analysis of the conjugates prepared by the method described in this invention showed discrete DMx-antibody conjugate peaks for antibody bearing increasing numbers of maytansinoid molecules per antibody molecule (FIG. 4B). In contrast, the MS of the conjugate obtained using the traditional 2-step method was nearly unresolved suggesting inhomogeneity of the conjugate preparation presumably due to cross-linking or inactivated maleimide linker (FIG. 4A). Based on MS, therefore, the conjugate prepared using the method described in this invention is superior to that synthesized by the traditional two-step method.

Figure 5:
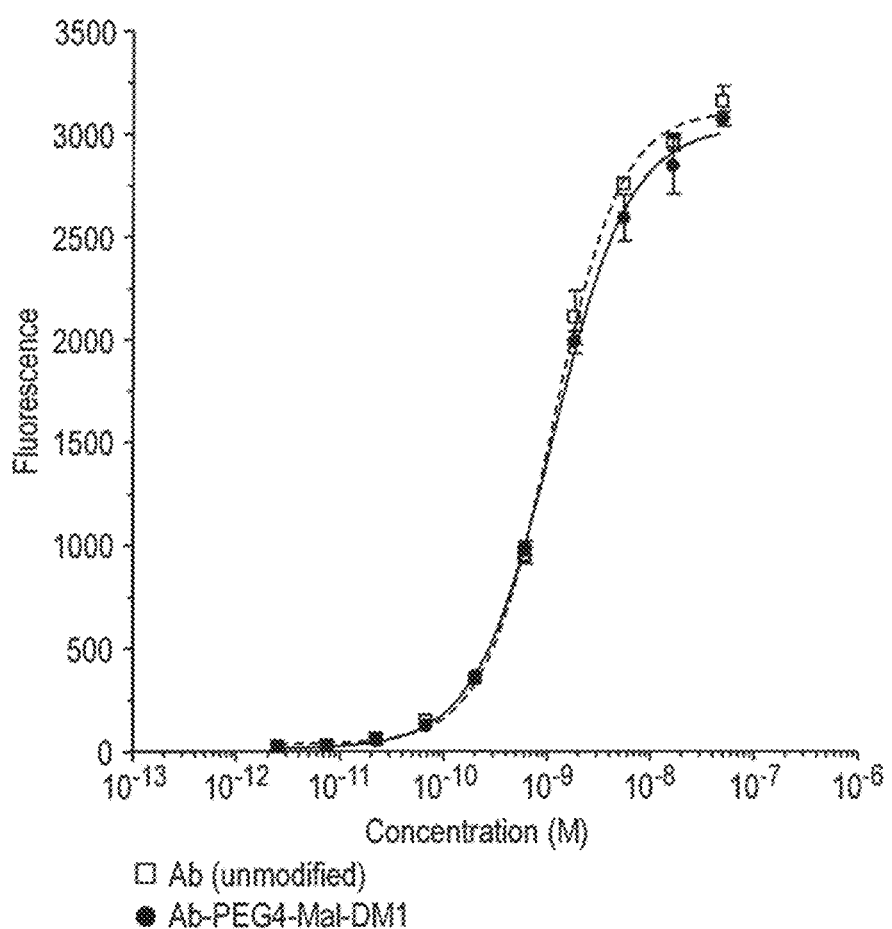
FIG. 5 shows binding of an anti-CanAg antibody-$PEG_4$-Mal-DM1 conjugate with 6.7 DM1 per antibody (prepared using the method described in this invention) versus binding of unmodified antibody toward CanAg antigen-expressing COLO205 cells. The binding was measured in fluoresence units.
Figure 6:
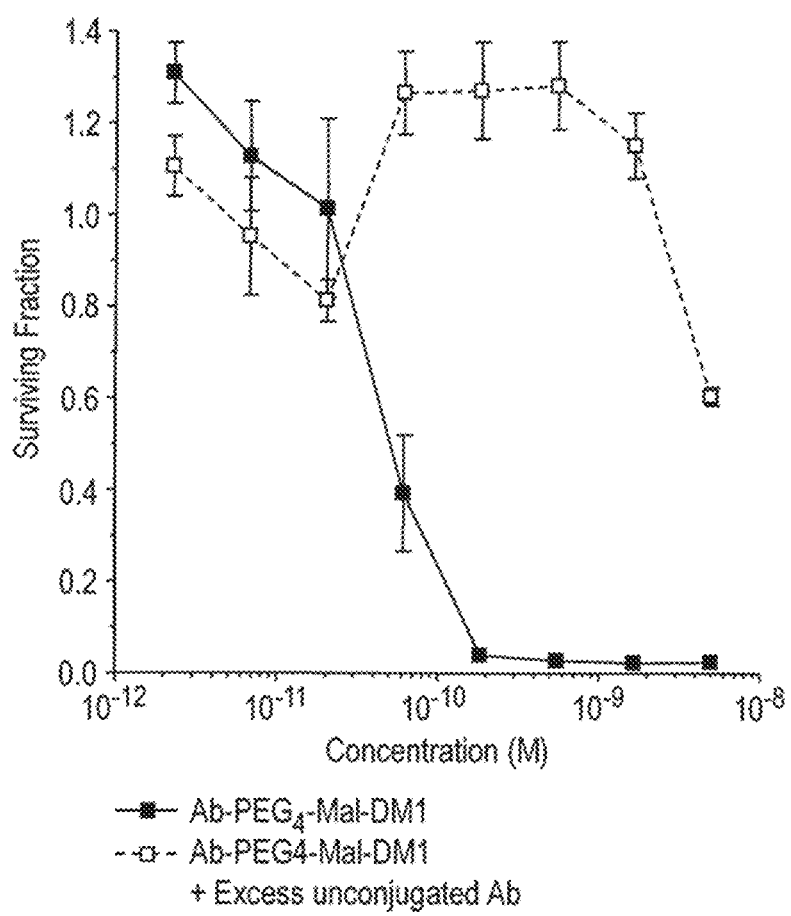
FIG. 6 shows in vitro cytotoxicity of an anti-CanAg Antibody-$PEG_4$-Mal-DM1 conjugate with 6.7 DM1 per antibody (prepared using the method described in this invention) toward CanAg antigen-expressing COLO205 cells. The conjugate was added to COLO205 cells, and after 5 days of continuous incubation with the conjugate, the viability of the cells was measured using WST-8 assay. A control experiment to demonstrate the specificity of the conjugate was carried out using an excess of unconjugated anti-CanAg antibody to block the binding and cytotoxicity of the conjugate toward target cancer cells.

The binding of an anti-CanAg Ab-PEG$_4$-Mal-DM1 conjugate prepared by the method described in this invention was measured by flow cytometry using the antigen-expressing COLO205 cells, and was found to be similar to that of unconjugated antibody suggesting that the conjugation had no detrimental effect on the binding of the antibody (FIG. 5). The cytotoxic activity of the anti-CanAg Ab-PEG$_4$-Mal-DM1 conjugate prepared by the method described in this invention was measured in vitro using COLO205 colon cancer cells expressing the CanAg antigen (FIG. 6). The antigen-expressing cancer cells were plated at around 1000 cells/well in a 96 well plate in cell culture media containing fetal bovine serum and exposed to varying concentrations of Ab-DMx conjugate. After a 5 day exposure to the conjugate, the viable cells remaining in each well were measured using the WST-8 assay (Dojindo Molecular Technologies). As shown in FIG. 6, the anti-CanAg Ab-PEG$_4$-Mal-DM1 conjugate prepared using this method was highly potent at low concentrations toward CanAg antigen-expressing COLO205 colon cancer cells. The cytotoxicity of the anti-CanAg Ab-PEG$_4$-Mal-DM1 conjugate prepared by the method described in this invention was specific to COLO205 cells as it could be blocked by the addition of excess, unconjugated antibody.

Figure 7:
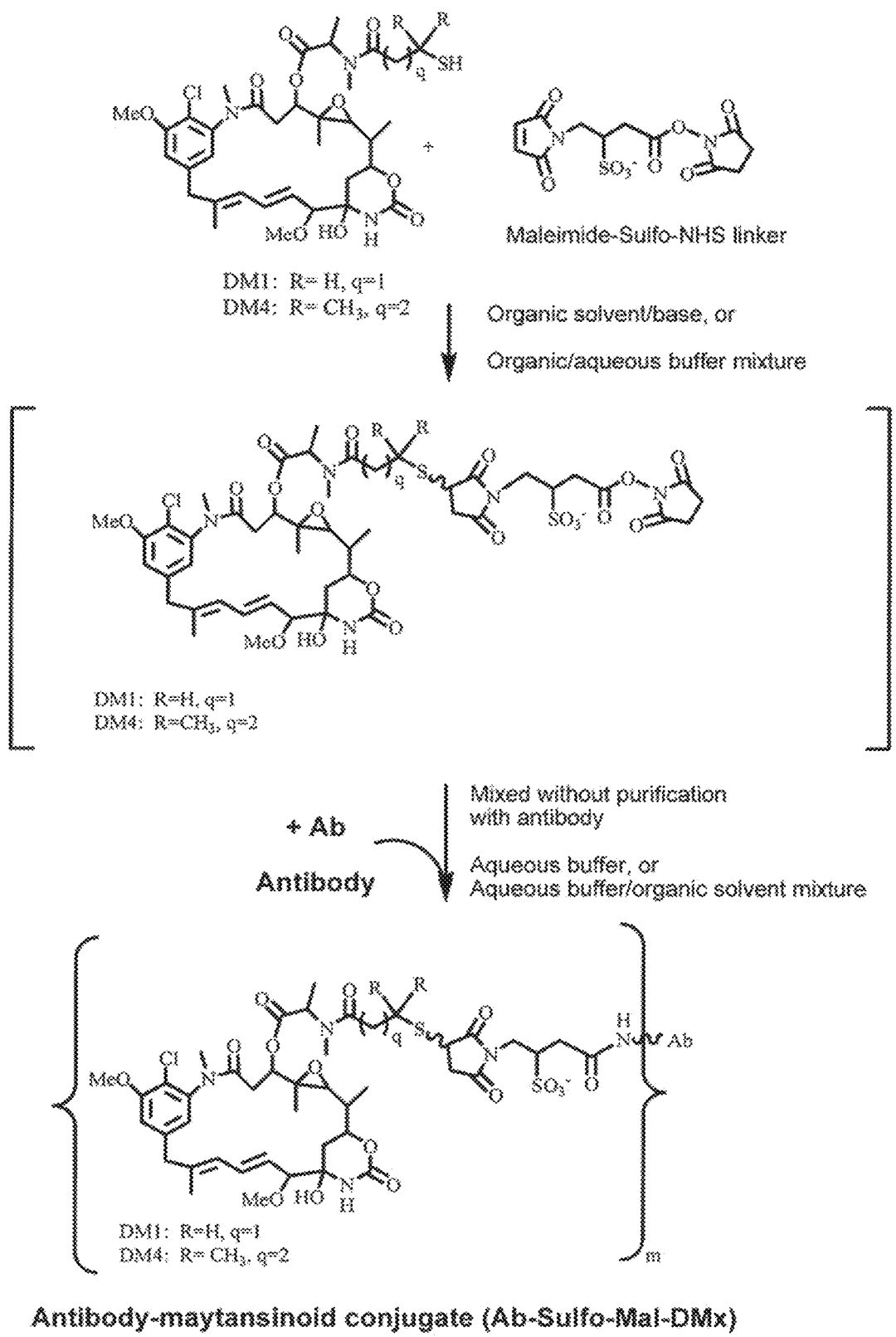
FIG. 7 shows conjugation of antibody with a reaction mixture of DM1 (or DM4) and Maleimide-Sulfo-NHS linker.

Example 2. Conjugation of Antibody with DM1/DM4 Using Maleimide-Sulfo-NHS Linker by this Method (FIG. 7) Versus Traditional Sequential Two-Step Method Stock solutions of DMx thiol and the maleimide-Sulfo-NHS heterobifunctional linker were made up in N,N-dimethylacetamide (DMA) at concentrations of 30-60 mM. The linker and DMx thiol were mixed together in DMA containing up to 40% v/v of 200 mM succinate buffer, 2 mM EDTA, pH 5.0 to give a ratio of DMx to linker of 1.6 and a final concentration of DMx equal to 15 mM. After mixing, the reaction was left for 1-4 h and then an aliquot of the reaction mixture was diluted 10 fold to measure the absorbance at 302-320 nm for assessing the completion of reaction and the absence of maleimide. (Additional reverse phase HPLC analysis of a frozen aliquot of the reaction mixture was carried out later with absorbance monitoring at 302 nm and 252 nm to verify complete disappearance of linker maleimide and formation of the desired linker-DMx reagent at the time of addition of the reaction mixture to antibody). When no further maleimide was present by UV, an aliquot of the reaction mixture was added to a mixture of antibody in phosphate buffer (pH 7.5) under final conjugation conditions of 4 mg/ml Ab, 90% phosphate buffer/10% DMA, pH 7.5. The conjugation reaction was allowed to proceed at ambient temperature for 2 h. The Ab-DMx conjugate was purified from excess unreacted DMx and unconjugated linker products using a G25 gel filtration column equilibrated in pH 7.5 phosphate buffer or by tangential flow filtration. The conjugate was kept at 4° C. for 2 days in pH 7.5 buffer to allow the dissociation of any DMx species attached to antibody non-covalently or via labile linkage. The conjugate was then dialyzed overnight into pH 5.5 histidine/glycine buffer and then filtered through a 0.22 µm filter for final storage. The number of DMx molecules per Ab antibody molecule (average) in the final conjugate was measured by determining absorbance of the conjugate at 252 and 280 nm and using known extinction coefficients for DMx and antibody at these two wavelengths.

For comparison, the Ab-Sulfo-Mal-DMx conjugates were prepared using the traditional 2-step conjugation method. The antibody (Ab) at a concentration of 8 mg/ml in pH 7.5 phosphate buffer/5% DMA buffer was modified with excess bifunctional maleimide-Sulfo-NHS linker. The reaction was allowed to proceed at 20° C. for 2 h and then the modified Ab was purified away from excess unreacted linker using G25 chromatography. The recovery of purified Ab was determined by UV absorbance at 280 nm. The number of linked maleimide groups in the modified Ab was determined using a small aliquot of modified antibody by addition of a known amount of thiol (such as 2-mercaptoethanol), added in excess over the maleimide, to react with the maleimide residues in the modified antibody and then assaying the remaining thiol by Ellman's assay using DTNB reagent (extinction coefficient of TNB thiolate at 412 nm=14150 M$^{-1}$ cm$^{-1}$; Riddles, P. W. et al., Methods Enzymol., 1983, 91, 49-60; Singh, R., Bioconjugate Chem., 1994, 5, 348-351). The conjugation of modified Ab with DMx was carried out at an antibody concentration of 2.5 mg/ml in 95% pH 7.5 phosphate buffer/5% DMA (v/v), with 1.7 molar equivalents of DMx thiol added per mol of linked maleimide in the Ab. The reaction was left for 8-24 h at 18° C. and the conjugate was separated from excess, unreacted DMx via G25 size-exclusion chromatography. After purification the conjugate was kept at 4° C. for 2 days in pH 7.5 buffer to allow the dissociation of any DMx species attached to antibody non-covalently or via labile linkage. The conjugate was then dialyzed overnight into pH 5.5 histidine/glycine buffer and then filtered through a 0.22 µm filter for final storage. The number of DMx molecule per Ab molecule in the final conjugate was measured by determining absorbance of the conjugate at 252 and 280 nm and using known extinction coefficients for DMx and antibody at these two wavelengths.

Figure 8:
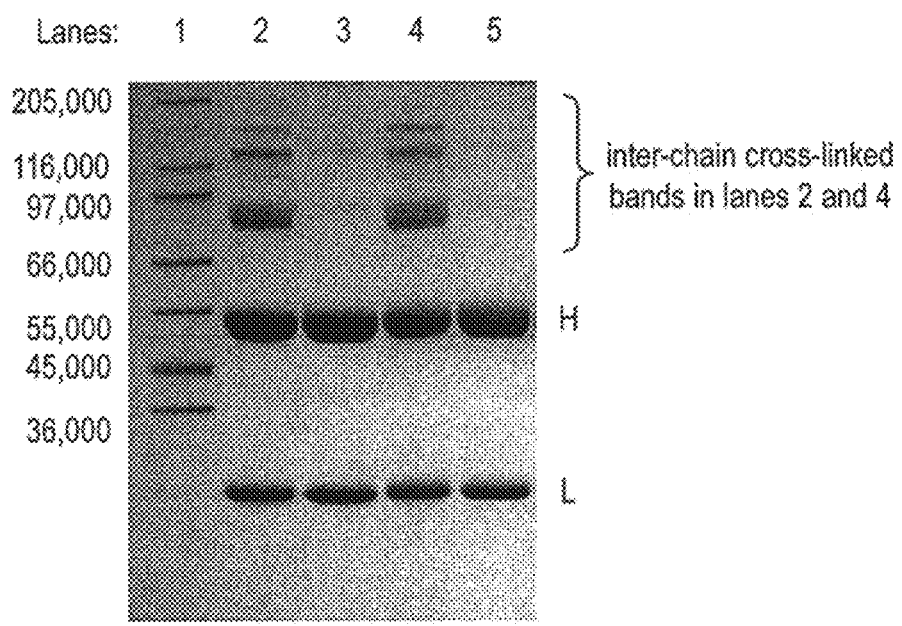
FIG. 8 shows reducing SDS-PAGE of Ab-(Sulfo-Mal)-DM1 conjugates prepared using the method described in this invention versus conjugates prepared using the traditional 2-step method. Each sample lane contained 10 µg protein; the gel was stained with Coomassie Blue. Lane 1 contained molecular weight markers. Lanes 3 and 5 contained conjugates prepared by the method described in this invention and contained 3.6 and 5.6 DM1 per Ab, respectively. Lanes 2 and 4 contained conjugates prepared by the traditional two-step method and contained 4.0 and 5.7 DM1 per Ab, respectively.

Reducing SDS PAGE was carried out using conjugate and antibody samples (10 µg/lane) using the NuPage electrophoresis system (Invitrogen) with a NuPage 4-12% Bis Tris Mini Gel and NuPAGE MOPS SDS running buffer (FIG. 8). Bands on the gel with molecular weights of 75, 125, and 150 kDa were indicative of inter-chain cross-linked species (HL, H$_2$L and H$_2$L$_2$ respectively). A comparison of Ab-Sulfo-Mal-DM1 conjugates with ~4 DM1/Ab (lane 3, by this method, and lane 2, by traditional 2-step conjugation method, respectively) and ~6 DM1/Ab (lane 5, by this method, and lane 4, by traditional 2-step conjugation method, respectively) clearly shows that conjugates made via the method described in this invention (lanes 3 and 5) have much smaller proportion of high molecular weight cross-linked species than conjugates made by the traditional 2-step method (lanes 2 and 4).

Figures 9A, 9B:
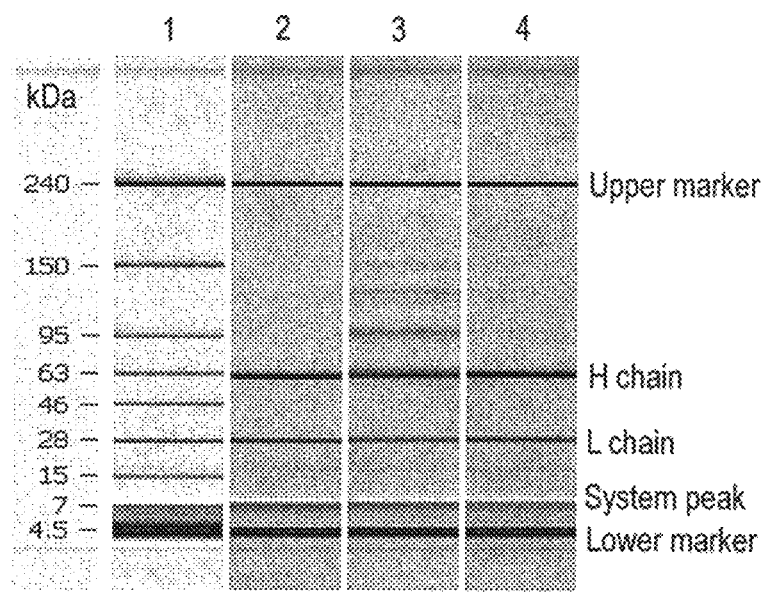
FIGS. 9A-B show Protein LabChip electrophoresis of Ab-(Sulfo-Mal)-DM1 conjugate prepared using the method described in this invention versus conjugate prepared using the traditional 2-step method.

Protein LabChip electrophoresis analysis (under reducing condition) of the antibody-Sulfo-Mal-DM1 conjugate prepared by the method described in this invention showed the heavy and light chain major bands with percentages of 70 and 28% (of total protein), which are similar to those for unconjugated antibody of 70 and 30% respectively (FIGS. 9A-B). In contrast, the conjugate prepared using the traditional two-step method showed heavy and light bands of only 53 and 23% respectively, and major bands of higher molecular weights ranging from 99-152 kDa presumably due to inter-chain cross-linking (FIGS. 9A-B). Based on the quantitative Protein LabChip analysis, the conjugate prepared by the method described in this application is much superior in terms of lack of inter-chain cross-linking compared to that prepared using the conventional two-step process.

Figure 10A:
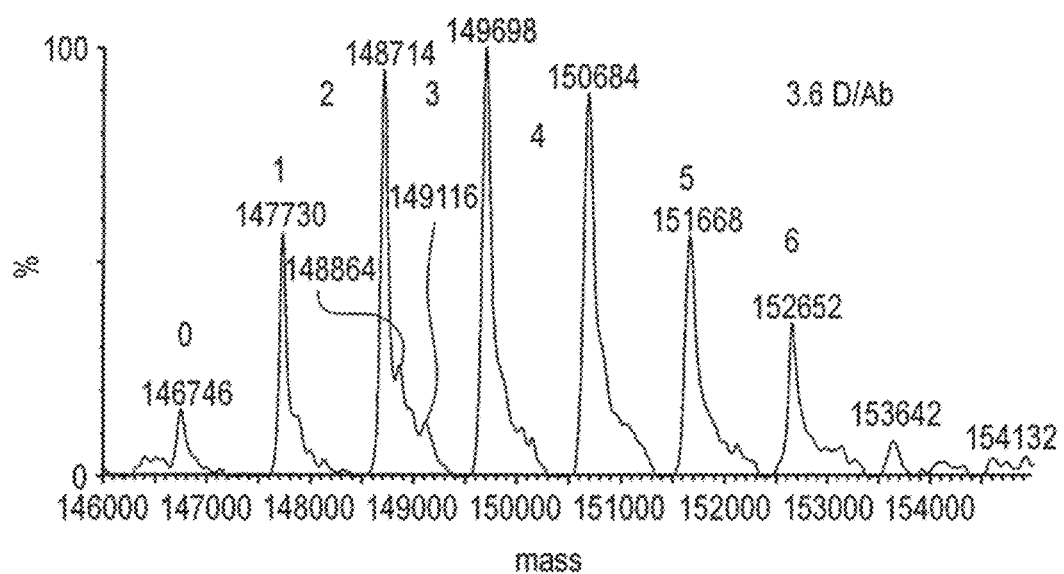
FIGS. 10A-B show LC-MS comparison of Antibody-(Sulfo-Mal)-DM1 conjugate prepared by the method described in this invention versus by the traditional two-step conjugation method.
Figure 10B:
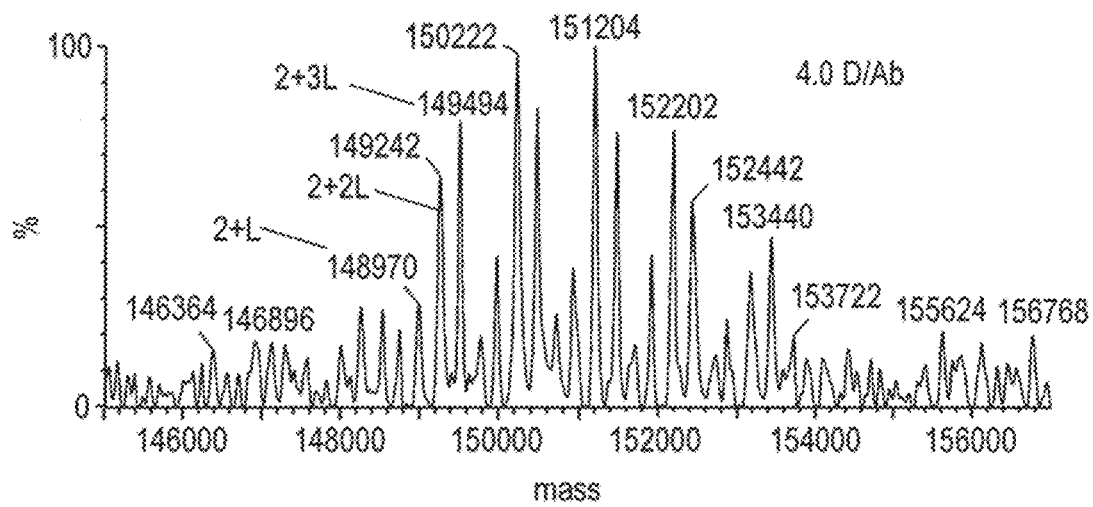
Figure 17:
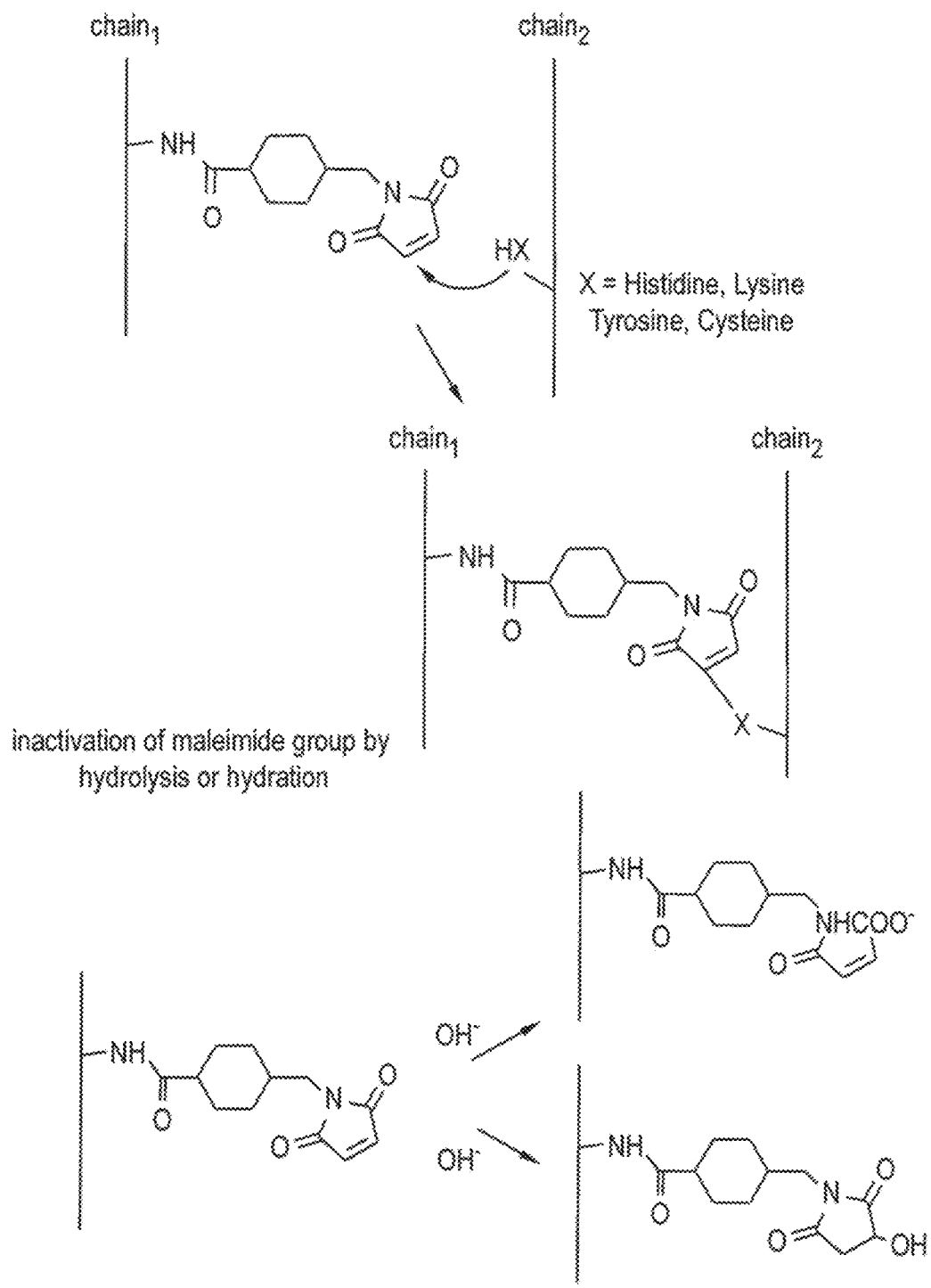
FIG. 17 shows proposed mechanisms for inter-chain cross-linking and maleimide inactivation during conjugation by the traditional 2-step method.

The Ab-Sulfo-mal-DM1 conjugates with similar drug loads made via the method described in this invention and by the traditional two step method were compared by size exclusion LC/MS analysis (FIGS. 10A-B). The conjugates made via the method described in this invention show the desired MS spectrum containing only the expected distribution of peaks with mass equal to Ab-(linker-DMx)$_n$ (FIG. 10A). In the case of conjugates made using the traditional two-step method, the major peaks in the spectra all contain one or more hydrolyzed or cross-linked linker fragments in addition to the desired Ab-(linker-DMx)$_n$ moieties (FIG. 10B). The putative mechanism of the inter-chain cross-linking or aqueous inactivation of maleimide in the traditional 2-step reaction sequence is shown in FIG. 17, whereby the incorporated maleimide (or haloacetamide) residue from the initial reaction of antibody with the heterobifunctional linker can react with intramolecular (or intermolecular) histidine, lysine, tyrosine, or cysteine residues resulting in inter-chain cross-linking, or the initially incorporated maleimide (or haloacetamide) residue can get inactivated (such as by hydrolytic maleimide ring cleavage or by aqueous addition to maleimide) and therefore become unavailable for the rapid reaction with thiol-bearing effector or reporter group. Thus the LC-MS analysis clearly shows that the method described in this invention has the advantage of producing homogeneous conjugate with little or no hydrolyzed or cross-linked linker fragments attached to antibody.

Figure 11:
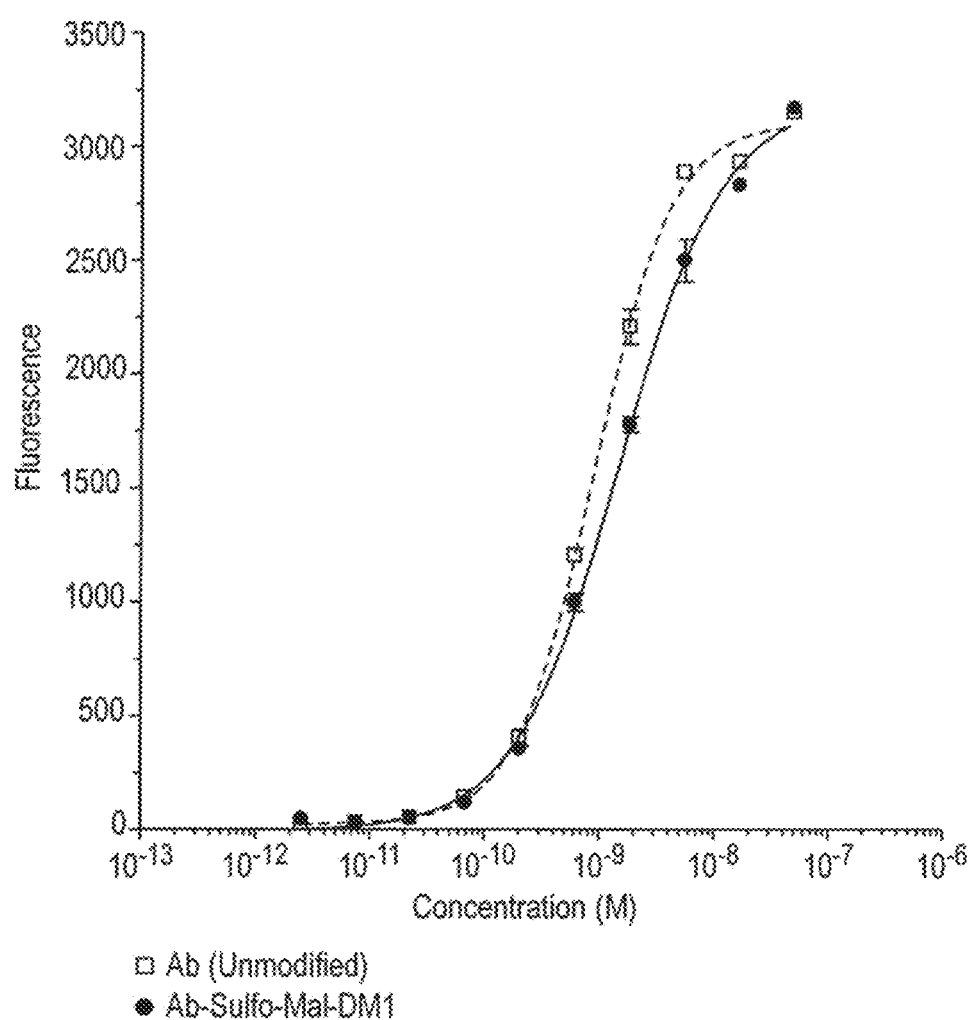
FIG. 11 shows binding of an anti-CanAg antibody-Sulfo-Mal-DM1 conjugate with 5.6 DM4 per antibody (prepared using the method described in this invention) versus binding of unmodified antibody toward CanAg antigen-expressing COLO205 cells. The binding was measured in fluoresence units.
Figure 12:
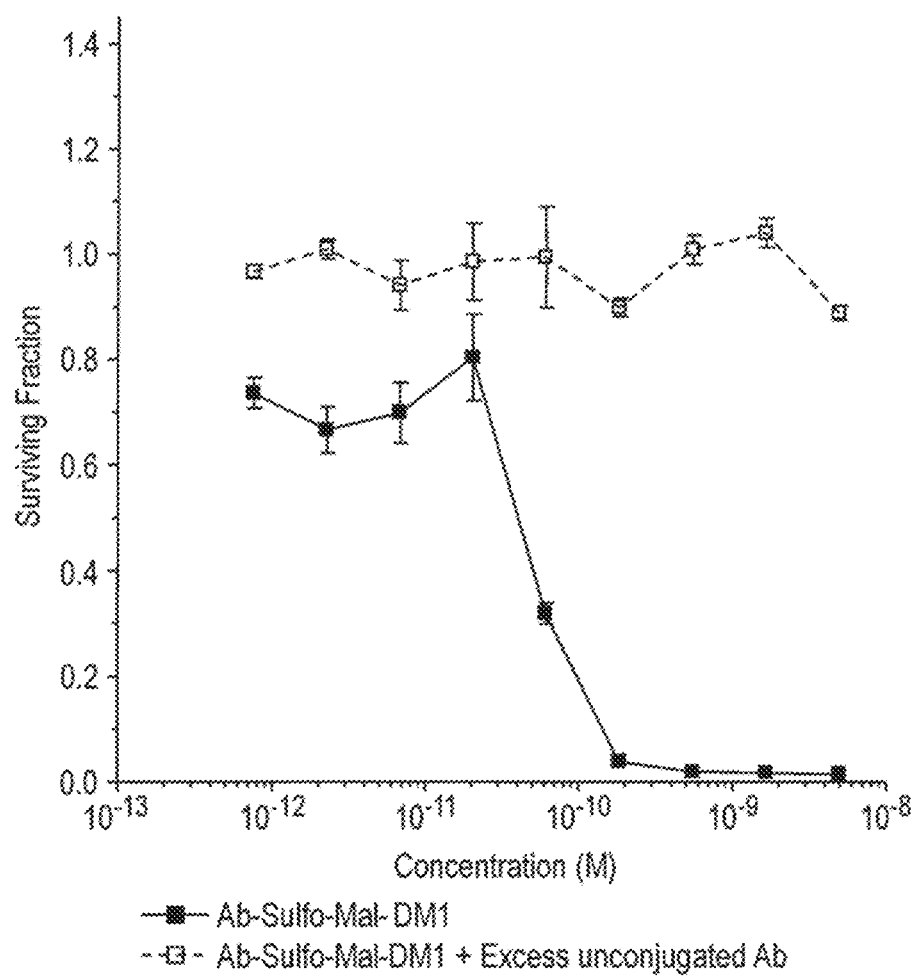
FIG. 12 shows in vitro cytotoxicity of an anti-CanAg Antibody-Sulfo-Mal-DM1 conjugate with 5.6 DM4 per antibody (prepared using the method described in this invention) toward CanAg antigen-expressing COLO205 cells. The conjugate was added to COLO205 cells and after 5 days of continuous incubation with the conjugate, the viability of the cells was measured using WST-8 assay. A control experiment to demonstrate the specificity of the conjugate was carried out using an excess of unconjugated anti-CanAg antibody to block the binding and cytotoxicity of the conjugate toward target cancer cells.

The binding of an anti-CanAg Ab-Sulfo-Mal-DM1 conjugate with 5.6 maytansinoid load per antibody molecule (average) prepared by the method described in this invention was measured by flow cytometry using the antigen-expressing COLO205 cells, and was found to be similar to that of unconjugated antibody suggesting that the conjugation did not affect the binding of the antibody to target antigen (FIG. 11). The cytotoxic activity of the anti-CanAg Ab-Sulfo-Mal-DM1 conjugate prepared by the method described in this invention was measured in vitro using COLO205 colon cancer cells expressing the CanAg antigen (FIG. 12). The antigen-expressing cancer cells were plated at around 1000 cells/well in a 96 well plate in cell culture media containing fetal bovine serum and exposed to varying concentrations of Ab-DMx conjugate. After a 5 day exposure to the conjugate, the viable cells remaining were measured using the WST-8 assay (Dojindo Molecular Technologies). As shown in FIG. 12, the anti-CanAg Ab-Sulfo-Mal-DM1 conjugate prepared using this method was highly potent at low concentrations toward CanAg antigen-expressing COLO205 colon cancer cells. The cytotoxicity of this conjugate was specific as it could be blocked by competition with excess, unconjugated antibody.

Figure 18:
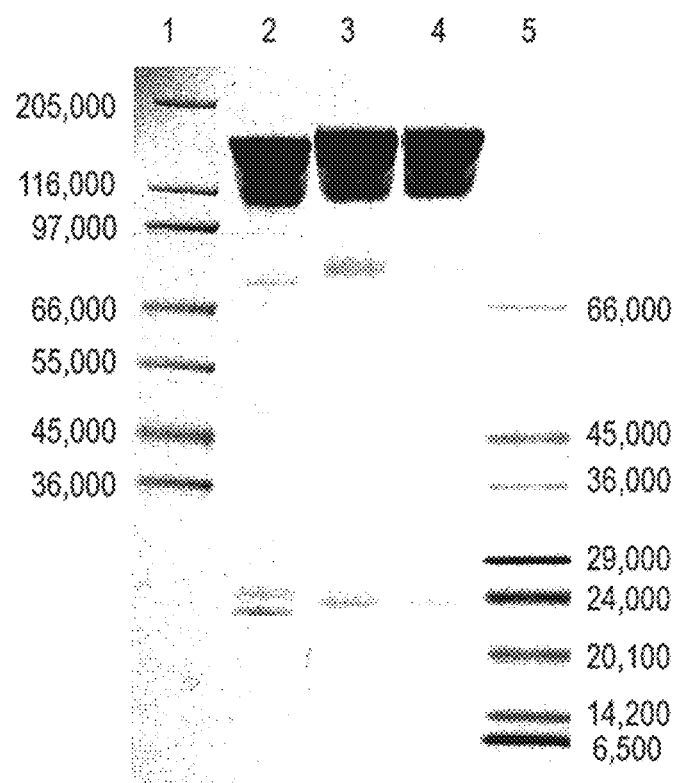
FIG. 18 shows non-reducing SDS PAGE of Ab-(Sulfo-Mal)-DM4 conjugate prepared using the method described in this invention and quenching of free DM4 thiol (after the initial DM4+NHS-Sulfo-Mal heterobifunctional reagent coupling reaction) using 4-maleimidobuytric acid prior to the antibody conjugation reaction. Each sample contained 10 μg protein; the gel was stained with Coomassie Blue. Lanes 1 and 5 contained molecular weight markers. Lane 2 contained Ab alone. Lane 3 contained conjugate prepared by the method described in this invention without addition of 4-maleimidobuytric acid. Lane 4 contained conjugate prepared by the method described in this invention with addition of 4-maleimidobuytric acid after the initial DM4+NHS-Sulfo-Mal heterobifunctional reagent (prior to the antibody conjugation step).

An alternative method of conjugation using the method described in this invention involved a quenching step using maleimide or haloacetamide reagents (such as 4-maleimidobutyric acid, or 3-maleimidopropionic acid, or N-ethylmaleimide, or iodoacetamide, or iodoacetic acid) after the completion of the initial DMx and heterobifunctional linker reaction (before the addition of the reaction mixture to the antibody) to quench the excess DMx thiol group in order to prevent any unwanted reaction of DMx thiol with the antibody. In a specific example, following completion of the initial DMx and heterobifunctional linker reaction (before the addition of the reaction mixture to the antibody), 4-maleimidobutyric acid was added to quench the excess DMx thiol group in order to prevent any unwanted reaction of DMx thiol with the antibody during the conjugation reaction. To a reaction mixture of DM4 and Sulfo-Mal-NHS heterobifunctional reagent that contained an excess of DM4 (3 mM), upon completion of the desired DM4 thiol coupling to the maleimide group of the heterobifunctional reagent, a two-fold molar excess of 4-maleimidobutyric acid (6 mM) was added to the reaction mixture at ambient temperature for 20 minutes to quench the remaining DM4 from the initial coupling reaction. Without purification of the reaction mixture, an aliquot was mixed with a solution of antibody in phosphate buffer (pH 7.5) under final conjugation conditions of 4 mg/ml Ab, 90% aqueous phosphate buffer/10% DMA, pH 7.5. The conjugation reaction was allowed to proceed at ambient temperature for 2 h. The antibody-DM4 conjugate was purified from the excess small-molecule DM4 and linker reactants using a G25 gel filtration column equilibrated in pH 7.5 phosphate buffer. The conjugation mixture was further kept at 4° C. for 2 days in pH 7.5 buffer to allow the dissociation of any DMx species attached to antibody non-covalently or via labile linkage. The conjugate was then dialyzed overnight into pH 5.5 histidine/glycine buffer and filtered through a 0.22 μm filter for final storage. The average number of DM4 molecules per Ab molecule in the final conjugate was measured by determining absorbance of the conjugate at 252 and 280 nm and using known extinction coefficients for DM4 and antibody at these two wavelengths. The conjugate samples were analyzed by non-reducing SDS PAGE using the NuPage electrophoresis system with a 4-12% Bis Tris Gel (Invitrogen). The heat-denatured samples were loaded at 10 μg/lane. The non-reducing SDS-PAGE of the conjugate prepared using the method described in this invention (without quenching) showed evidence of a light chain band (~25 kDa) and half-antibody band (heavy-light chain; ~75 kDa) (FIG. 18). On the other hand, the conjugate prepared using the method described in this invention which was treated with 4-maleimidobutyric acid (to cap excess DMx thiol) had significantly lower amounts of these undesirable bands (at levels comaparable to unmodifed antibody sample). Another advantage of the quenching of the initial DMx and heterobifunctional reaction mixture (before conjugation with the antibody) by thiol-quenching reagents such as 4-maleimidobutyric acid is that during the antibody conjugation reaction there is no "free" DMx (DM1 or DM4) species and therefore the final conjugate after purification does not contain "free" or unconjugated DMx species. The DMx-adduct with 4-maleimidobutyric acid (or other polar thiol-quenching reagents) is more water soluble than DMx and therefore can be more easily separated from the covalently linked antibody-DMx conjugate.

Figure 13:
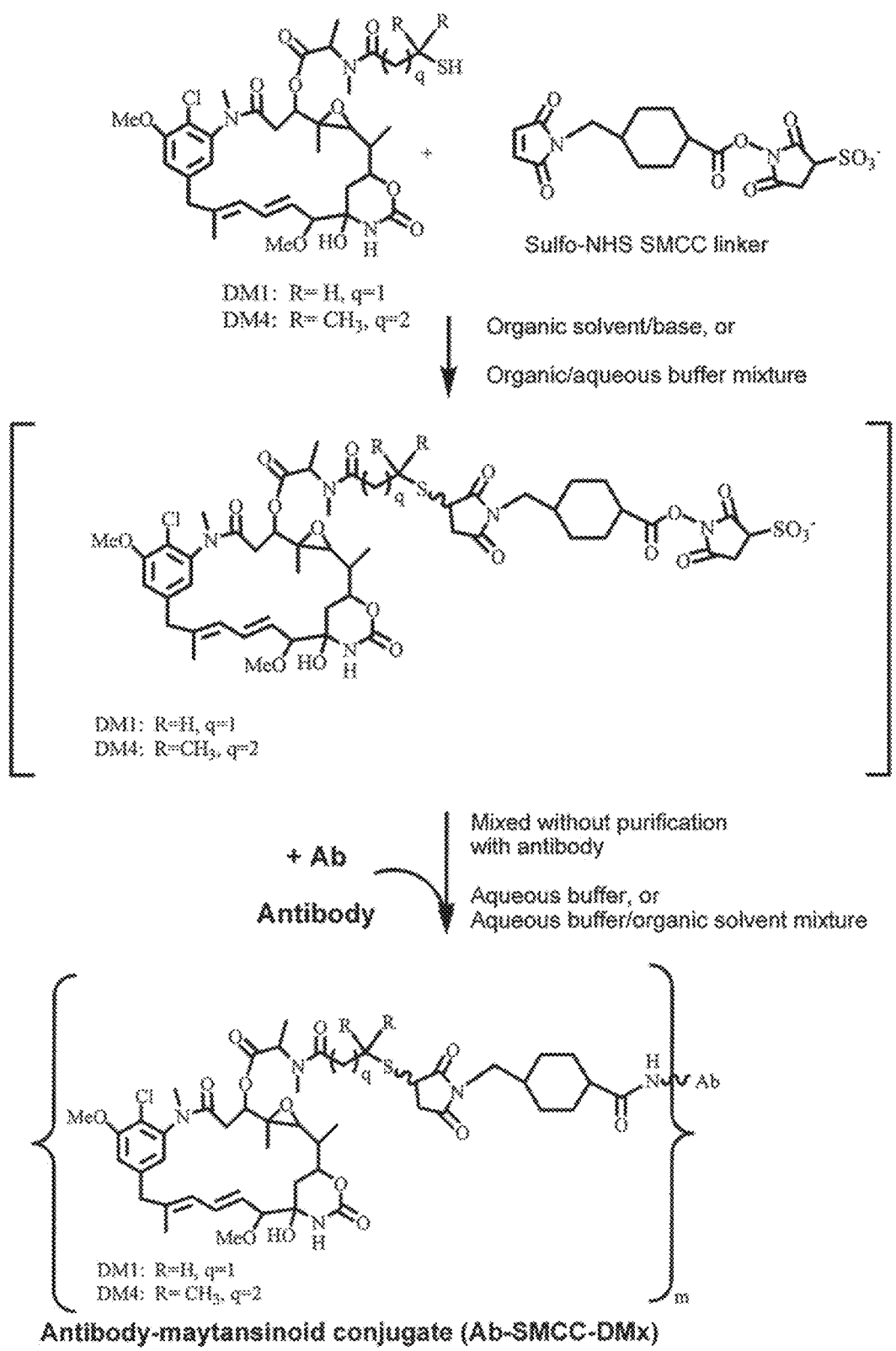
FIG. 13 shows conjugation of antibody with a reaction mixture of DM1 (or DM4) and Sulfo-NHS SMCC linker.

Example 3. Conjugation of Antibody with Maytansinoid (DM1/DM4) Using Sulfo-NHS-SMCC Linker (FIG. 13)

Stock solutions of DM1 or DM4 thiol (DMx) and the sulfo-SMCC heterobifunctional linker with sulfo-NHS group (purchased from Pierce Endogen; FIG. 13) were prepared in DMA at concentrations of 30-60 mM. Linker and DM1 or DM4 thiol were mixed together in DMA containing up to 40% v/v of aqueous 200 mM succinate buffer, 2 mM EDTA, pH 5.0 to give a ratio of DM1 or DM4 (DMx) to linker of 1.6:1 and a final concentration of DMx of 6 mM. After mixing, the reaction was left for 1-4 h at ambient temperature and then an aliquot of the reaction mixture was diluted 10-fold to measure absorbance at 302-320 nm to assess whether all of the maleimide had reacted. (Additional reverse phase HPLC analysis of a frozen aliquot of the reaction mixture was carried out later with monitoring at 302 nm and 252 nm to verify complete disappearance of linker maleimide and formation of the desired sulfo-NHS-linker-Mal-DMx reagent at the time of addition of the reaction mixture to antibody). When no further maleimide was present by UV an aliquot of the reaction was added to an aqueous solution of an antibody in phosphate buffer (pH 7.5) under final conjugation conditions of 4 mg/ml Ab, 90% phosphate buffer (aqueous)/10% DMA (v/v), pH 7.5. The conjugation reaction was allowed to proceed at ambient temperature for 2 h. Ab-DMx conjugate was purified from excess unreacted reagent and excess DMx using a G25 gel filtration column equilibrated in pH 7.5 phosphate buffer (aqueous). Conjugate was kept at 4° C. for 2 days in pH 7.5 buffer to allow the dissociation of any DMx species attached to Ab non-covalently or via labile linkage. The conjugate was then dialyzed overnight into pH 5.5 histidine/glycine buffer and then filtered through a 0.22 μm filter for final storage. The number of DMx molecule per Ab molecule in the final conjugate was measured by determining absorbance of the conjugate at 252 and 280 nm and using known extinction coefficients for DMx and antibody at these two wavelengths.

For comparison, the Ab-SMCC-DMx conjugates were prepared using the traditional 2-step conjugation method. The antibody (Ab) at a concentration of 8 mg/ml in 95% pH 6.5 phosphate buffer/5% DMA buffer was modified with excess bifunctional sulfo-SMCC linker with sulfo-NHS group (purchased from Pierce Endogen). The reaction was allowed to proceed at 25° C. for 2 h and then the modified Ab was purified away from excess unreacted linker using G25 chromatography. The recovery of purified Ab was determined by UV absorbance at 280 nm. The number of linked maleimide groups in the modified Ab was determined using a small aliquot of modified antibody by addition of a known amount of thiol (such as 2-mercaptoethanol), added in excess over the maleimide, to react with the maleimide residues in the modified antibody and then assaying the remaining thiol by Ellman's assay using DTNB reagent (extinction coefficient of TNB thiolate at 412 nm=14150 $M^{-1}$ $cm^{-1}$; Riddles, P. W. et al., Methods Enzymol., 1983, 91, 49-60; Singh, R., Bioconjugate Chem., 1994, 5, 348-351). The conjugation of modified Ab with DM1 or DM4 was carried out at an antibody concentration of 2.5 mg/ml in 95% pH 6.5 phosphate buffer/5% DMA (v/v), with 1.7 molar equivalents of DM1 or DM4 thiol added per mol of linked maleimide in the Ab. The reaction was left for 8-24 h at 18° C. and the conjugate was separated from excess, unreacted DM1 (or DM4) via G25 chromatography. After purification the conjugate was kept at 4° C. for 2 days in pH 6.5 buffer to allow the hydrolysis of any weakly linked DM1/DM4 species. The conjugate was then dialyzed overnight into pH 5.5 histidine/glycine buffer and then filtered through a 0.22 μm filter for final storage. The number of DM1/DM4 molecules per Ab molecule in the final conjugate was measured by determining absorbance of the conjugate at 252 and 280 nm and using known extinction coefficients for DM1/DM4 and antibody at these two wavelengths.

Figure 14:
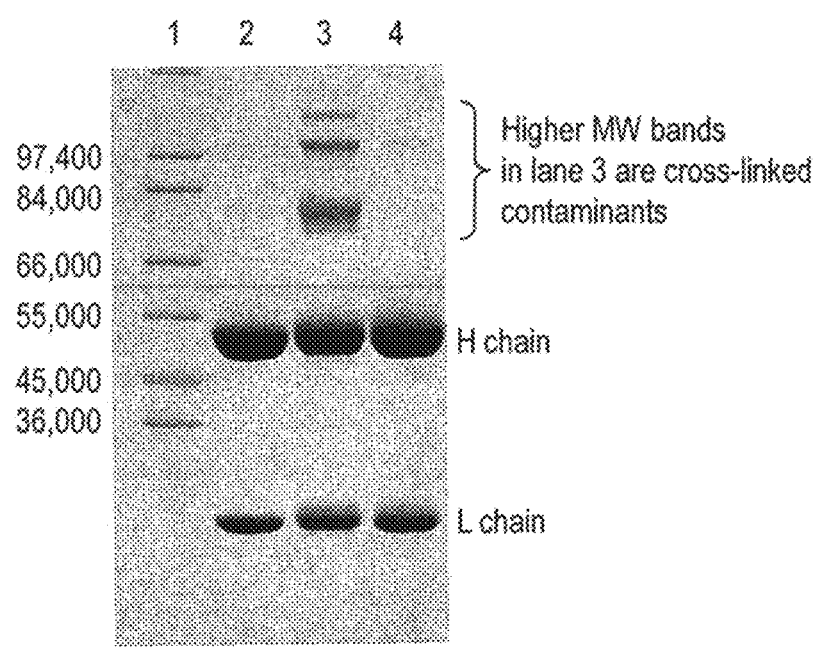
FIG. 14 shows reducing SDS-PAGE of Ab-(SMCC)-DM1 conjugate prepared using the method described in this invention versus conjugate prepared using the traditional 2-step method. Each sample lane contained 10 microgram total protein; the gel was stained with Coomassie Blue. Lane 1 contains molecular weight markers, Lane 2 contains unconjugated Ab, Lane 3 contains conjugate prepared by the traditional two-step method with 3.1 DM1 per Ab and Lane 4 contains conjugate prepared by the method described in this invention with 3.1 DM1 per Ab.

Reducing SDS PAGE was carried out on conjugate and antibody samples (10 μg/lane) using the NuPage electrophoresis system (Invitrogen) with a NuPage 4-12% Bis Tris Mini Gel and NuPAGE MOPS SDS running buffer (FIG. 14). Bands on the gel with molecular weights of 75, 125, and 150 kDa were indicative of inter-chain cross-linked species (HL, $H_2L$ and $H_2L_2$ respectively). A comparison of Ab-SMCC-DM1 conjugates with 3.1 D/Ab (lane 4, by this method, and lane 3, by the traditional 2-step method, respectively) clearly shows that conjugate made via the method described in this invention (lane 4) has much fewer high molecular weight cross-linked species than conjugates made by the traditional 2 step method (lane 3).

Figures 15A, 15B:
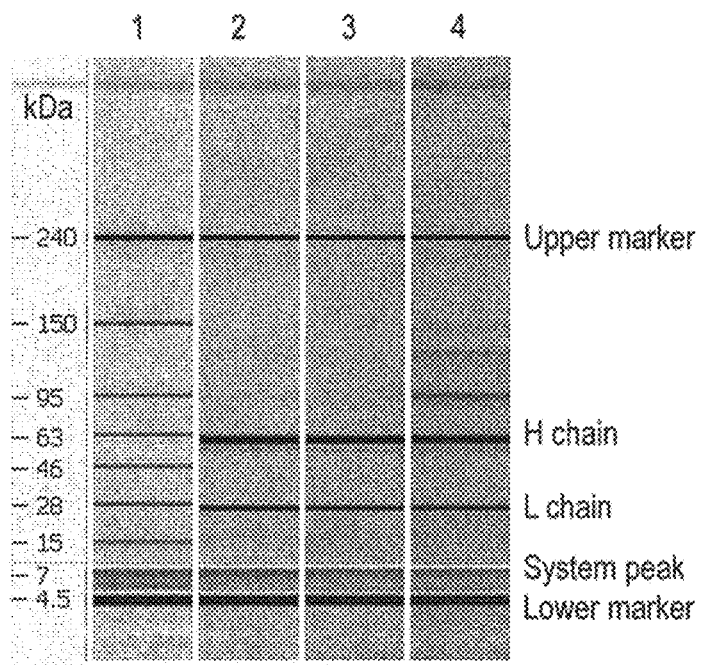
FIGS. 15A-B show Protein LabChip electrophoresis of Ab-(SMCC)-DM1 conjugate prepared using the method described in this invention versus conjugate prepared using the traditional 2-step method.

Protein LabChip electrophoresis analysis (under reducing condition) of the antibody-SMCC-DM1 conjugate prepared by the method described in this invention showed the heavy and light chain major bands with percentages of 67 and 30% (of total protein), which are similar to those for unconjugated antibody of 68 and 30% respectively (FIGS. 15A-B). In contrast, the conjugate prepared using the traditional two-step method showed heavy and light bands of only 54 and 24% respectively, and major bands of higher molecular weights ranging from 96-148 kDa presumably due to inter-chain cross-linking (FIGS. 15A-B). Based on the quantitative Protein LabChip analysis, the conjugate prepared by the method described in this application is much superior in terms of lack of inter-chain cross-linking compared to that prepared using the conventional two-step process.

Figure 16A:
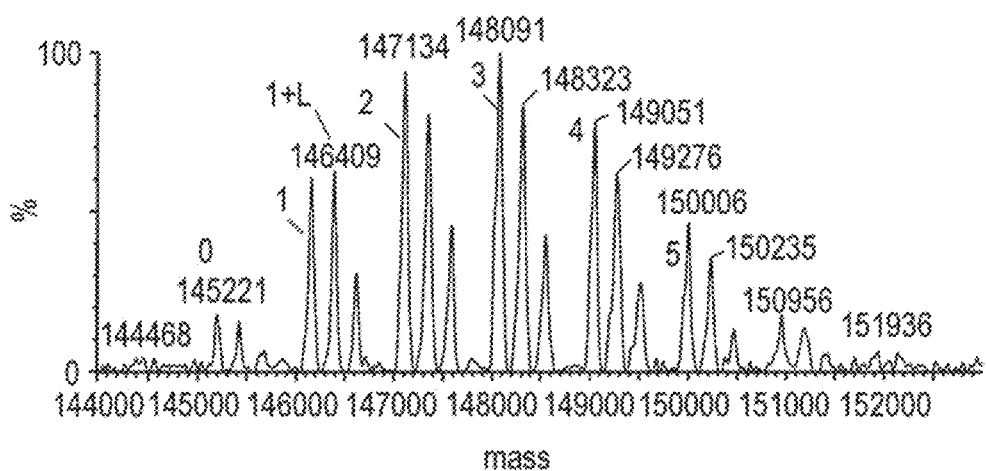
FIGS. 16A-B show LC-MS comparison of Antibody-(SMCC)-DM1 conjugate prepared by the method described in this invention versus conjugate prepared by the traditional two-step conjugation method.
Figure 16B:
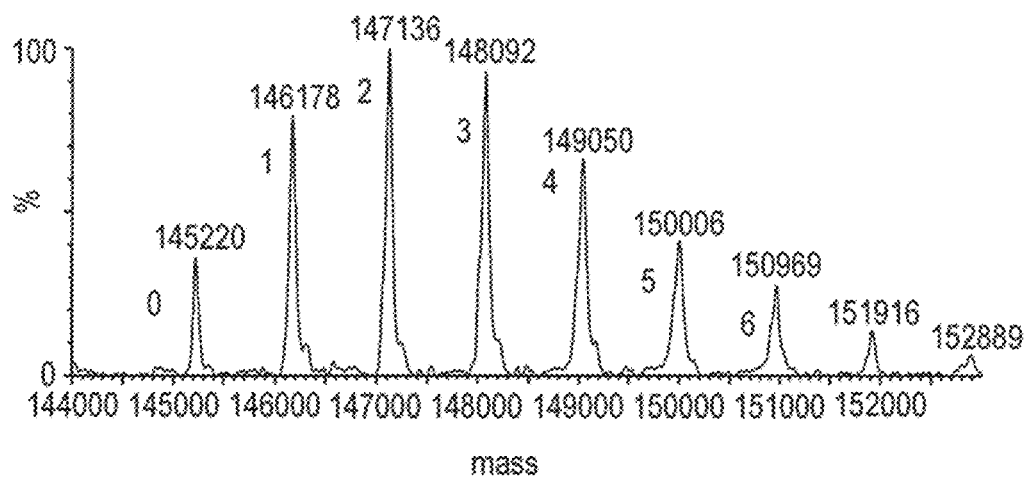

The Ab-SMCC-DM1 conjugates with similar drug loads made via the method described in this invention and by the traditional two step method were compared by size exclusion LC/MS analysis (FIGS. 16A-B). The conjugate made via the method described in this invention shows the desired MS spectrum containing only the expected distribution of peaks with mass equal to Ab-(linker-DMx)$_n$ (FIG. 16B). In the case of conjugate made using the traditional two-step method the spectrum shows a heterogeneous mixture of species which includes the desired Ab-(linker-DMx)$_n$ species plus additional species containing inactivated maleimide and cross-linked linker fragments (FIG. 16A). The putative mechanisms of the inter-chain cross-linking and maleimide inactivation in the traditional 2-step reaction sequence are shown in FIG. 17 whereby the incorporated maleimide (or haloacetamide residue) from the initial reaction of antibody with the heterobifunctional linker can react with intramolecular (or intermolecular) histidine, lysine, tyrosine, or cysteine residues resulting in inter-chain cross-linking, or the initially incorporated maleimide (or haloacetamide) residue can get inactivated by hydrolysis or hydration of the maleimide residue before the reaction step with the thiol-bearing DM1 or DM4 (DMx) agent. Thus the LC-MS analysis clearly shows that the method described in this invention has the advantage of producing homogeneous conjugate with little or no inactivated maleimide or cross-linked linker fragments attached to antibody.

Figure 19:
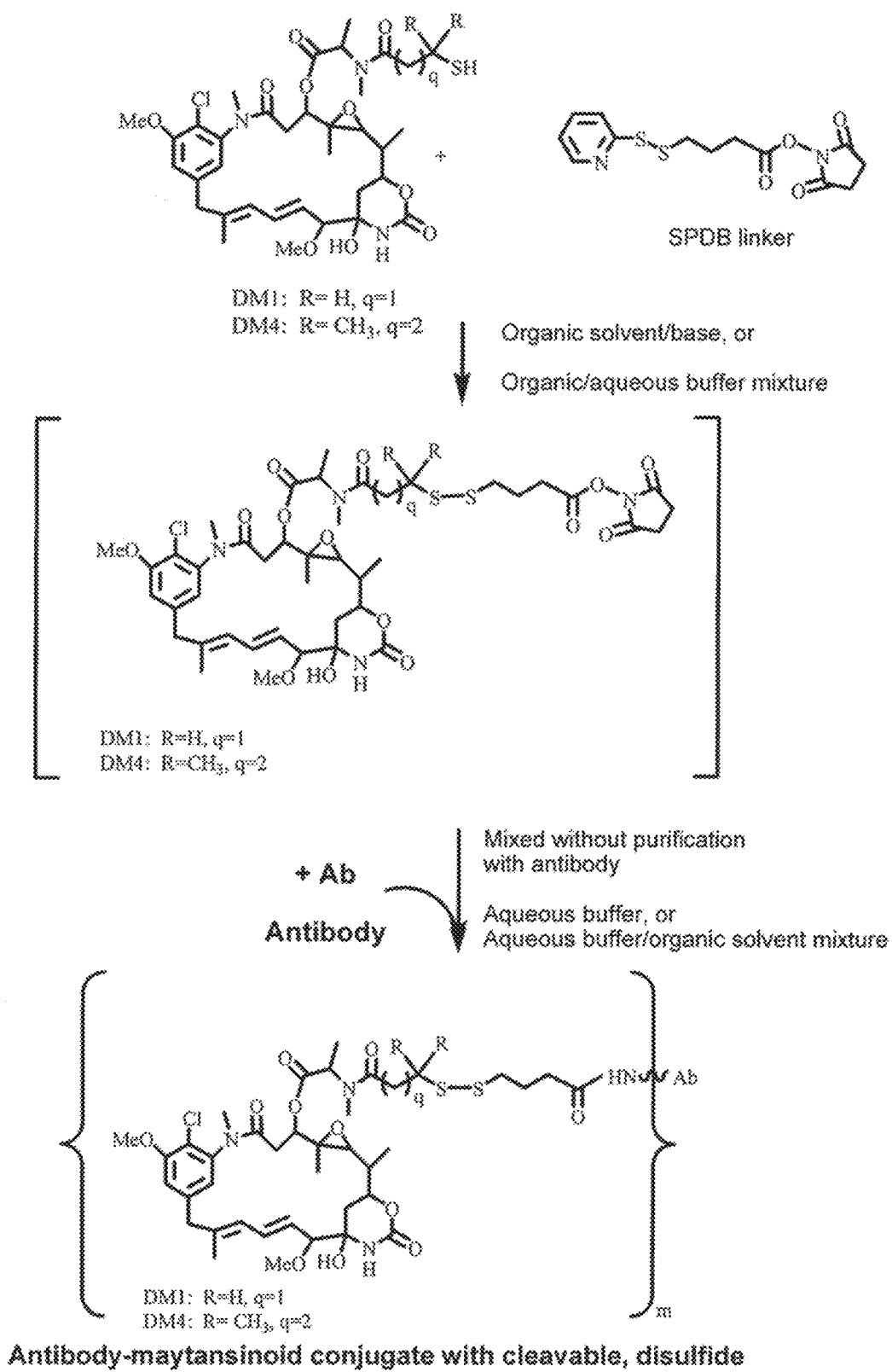
FIG. 19 shows preparation of disulfide-linked conjugate of antibody using a reaction mixture of DM1 (or DM4) and SPDB linker.

Example 4. Conjugation of Antibody with DM1/DM4 (DMx) with Cleavable, Disulfide Linkers by this Method (FIG. 19)

Stock solutions containing DM1 or DM4 thiol (DMx) and heterobifunctional linker 4-(2-pyridyldithio)butanoic acid-N-hydroxysuccinimide ester (SPDB) were prepared in DMA at concentrations of 30-60 mM. Linker and DMx thiol were mixed together in DMA containing up to 40% v/v of aqueous 200 mM succinate buffer, 2 mM EDTA, pH 5.0 to give a ratio of DM1 or DM4 (DMx) to linker of 1.6:1 and a final concentration of DMx of 8 mM. After mixing, the reaction was left for 1 h at ambient temperature and then an aliquot of the reaction was added to an aqueous solution of antibody in phosphate buffer (pH 7.5) under final conjugation conditions of 4 mg/ml Ab, 90% phosphate buffer (aqueous)/10% DMA (v/v), pH 7.5. The conjugation reaction was allowed to proceed at ambient temperature for 2 h. The Ab-DMx conjugate was purified from excess unreacted reagent and excess DMx using a G25 gel filtration column equilibrated in pH 7.5 phosphate buffer (aqueous). Conjugate was kept at 4° C. for 2 days in pH 7.5 buffer to allow for the dissociation of any DMx species attached to Ab non-covalently or via labile linkage. The conjugate was then dialyzed overnight into pH 5.5 histidine/glycine buffer and then filtered through a 0.22 μm filter for final storage. The number of DMx molecules per Ab molecule on the final conjugate was measured by determining absorbance of the conjugate at 252 and 280 nm using known extinction coefficients for DMx and antibody at these two wavelengths.

Figure 20:
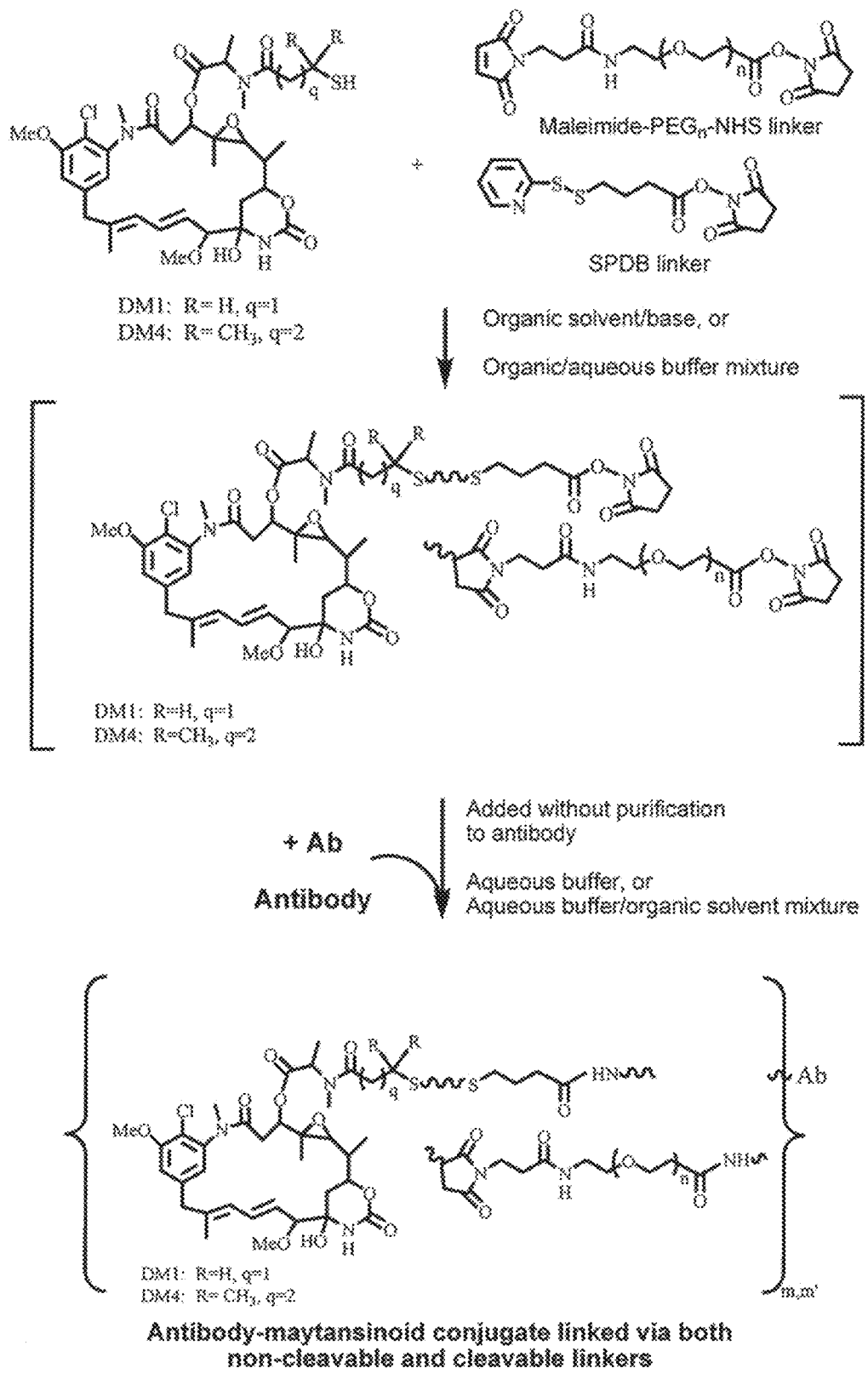
FIG. 20 shows preparation of antibody-maytansinoid conjugate with both disulfide- and non-cleavable $PEG_4$-Mal linkers via antibody conjugation with an unpurified reaction mixture of DM1 (or DM4) and both SPDB and NHS-$PEG_4$-Mal linkers.

Example 5. Preparation of Antibody-DM1/DM4 (Ab-DMx) Conjugate with Both Disulfide- and Non-Cleavable Linkers Using this Method (FIG. 20)

Stock solutions of DM1 or DM4 thiol (DMx) and the NHS-PEG$_n$-Maleimide heterobifunctional linker were prepared in N,N-dimethylacetamide (DMA) at concentrations of 30-80 mM. The NHS-PEG$_4$-Maleimide linker and DMx thiol were mixed together in DMA containing up to 40% v/v of 200 mM succinate buffer, 2 mM EDTA, pH 5.0 to give a molar ratio of DMx to linker of 1.6:1 and a final concentration of DMx equal to 8.0 mM. The reaction mixture was left to react for 2 h at ambient temperature. In a separate parallel reaction, SPDB linker and DMx thiol were mixed together and reacted in a similar fashion to the conditions used for NHS-PEG$_4$-maleimide reaction except for a reaction time of 1 h. After the completion of both reactions and without purification, equal volumes of PEG$_4$-Mal-DM4 mixture and SPDB-DM4 mixture were combined. An aliquot of the combined reaction mixtures was added without purification to a solution of antibody in phosphate buffer (pH 7.5) under final conjugation conditions of 4 mg/ml Ab, 90% phosphate buffer (aqueous)/10% DMA (v/v), pH 7.5. The conjugation reaction was allowed to proceed at ambient temperature for 2 h. Ab-DMx conjugate was purified from excess unreacted reagents and excess DMx using a G25 gel filtration column equilibrated in pH 7.5 phosphate buffer (aqueous). The conjugate was kept at 4° C. for 2 days in pH 7.5 buffer to allow for the dissociation of DMx species attached to Ab non-covalently or via labile linkage. The conjugate was then dialyzed overnight into pH 5.5 histidine/glycine buffer and then filtered through a 0.22 μm filter for final storage. The number of DMx molecules per Ab molecule on the final conjugate was measured by determining absorbance of the conjugate at 252 and 280 nm using known extinction coefficients for DMx and antibody at these two wavelengths.

Figure 21:
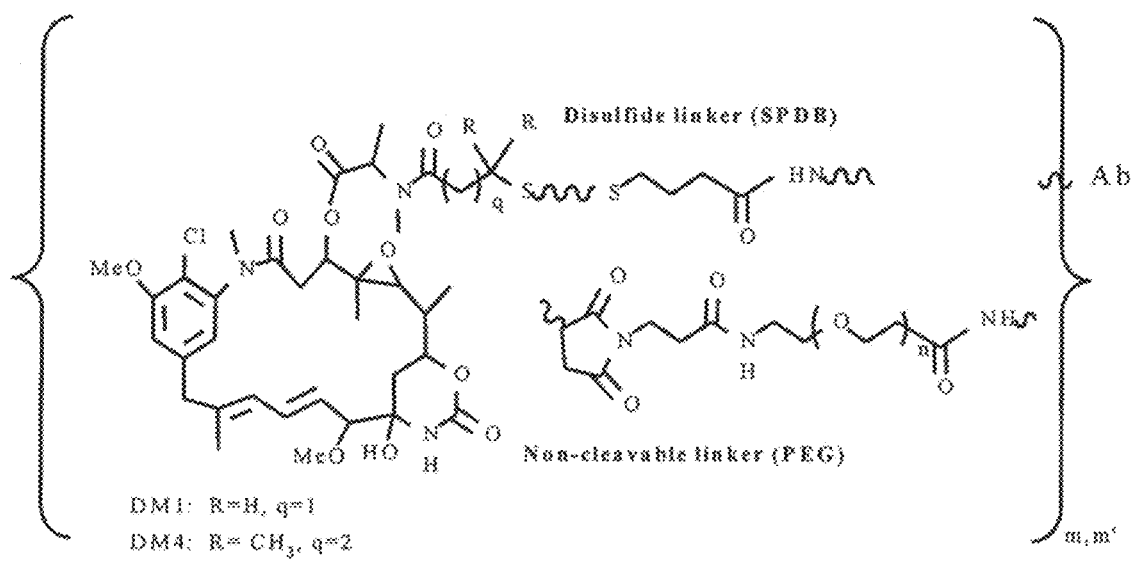
FIG. 21 shows MS of antibody-maytansinoid conjugate with both disulfide- and non-cleavable $PEG_4$-Mal linkers (prepared by conjugation of antibody with an unpurified reaction mixture of DM1, or DM4, and both SPDB and NHS-$PEG_4$-Mal linkers).
Figure 21:
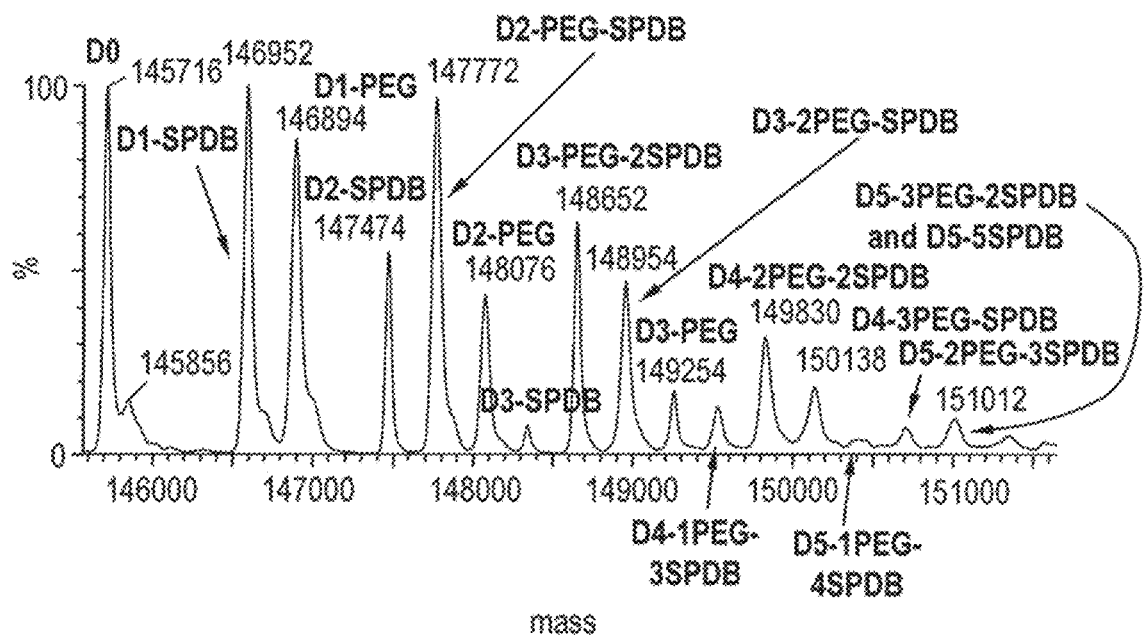

The Ab-(mixed SPDB and PEG$_4$-Mal linker)-DMx conjugate made via the method described in this invention was tested to determine the percent of incorporation of cleavable versus non-cleavable linker on the Ab by comparing DMx per antibody (D/A) ratio before and after DTT (dithiothreitol) treatment of the conjugate to reduce the disulfide linkage. In order to maintain reaction pH at 7.5 during DTT reduction, the conjugate was first dialyzed into 250 mM HEPES buffer pH 7.5. The conjugate was then reduced by reacting with 25 mM DTT for 20 min at 37° C. After the DTT reaction, the released DMx and DTT were separated from the reaction mixture using a G25 gel filtration column equilibrated in 250 mM HEPES buffer pH 7.5. The average number of DMx molecules per Ab molecule in the purified product was measured by determining the absorbance of the conjugate at 252 and 280 nm and using known extinction coefficients for DMx and antibody at these two wavelengths. The ratio between D/A of DTT-treated conjugate and D/A of non-DTT treated conjugate was used to calculate the percent of DMx attached to Ab via non-cleavable linkage. Two additional samples, Ab-SPDB-DM4 and Ab-PEG$_4$-Mal-DM4 conjugates, were treated with DTT as positive and negative controls, respectively. By comparing D/A ratio before and after DTT treatment, the control non-cleavable Ab-PEG$_4$-Mal-DM4 conjugate showed that approximately all linkers bound were found to be non-cleavable (93%) as expected. The Ab-(mixed SPDB and PEG$_4$Mal linker)-DMx conjugate containing both non-cleavable and disulfide linkers made via the method described in this invention had 41% less DMx cleaved by DTT treatment relative to the amount of DMx loss from the Ab-SPDB-DMx conjugate that consists entirely of cleavable linker. This demonstrated that the Ab-(mixed SPDB and PEG$_4$-Mal)-DMx conjugate made via the method described in this invention was composed of approximately 40% non-cleavable and 60% cleavable linkers. By changing the initial ratio of the non-cleavable and cleavable linker reagents, conjugates of antibody with maytansinoid or other effector can be prepared with different ratio of non-cleavable and cleavable linkers. FIG. 21 shows the mass spectrum of deglycosylated conjugate described above, which comprises of antibody with an average of 3.5 maytansinoid molecules per antibody molecule linked via both disulfide linkers (SPDB) and non-cleavable linkers (PEG). The MS shows discrete conjugate species bearing both cleavable and non-cleavable linkers (FIG. 21). For example, the conjugate peak designated D2-PEG-SPDB bears one disulfide-linked and one non-cleavable thioether-linked maytansinoid molecule; the conjugate peak designated D3-PEG-2SPDB bears two disulfide-linked and one non-cleavable thioether-linked maytansinoid molecules; and the conjugate peak designated D3-2PEG-SPDB bears one disulfide-linked and two non-cleavable thioether-linked maytansinoid molecules.

Figure 22:
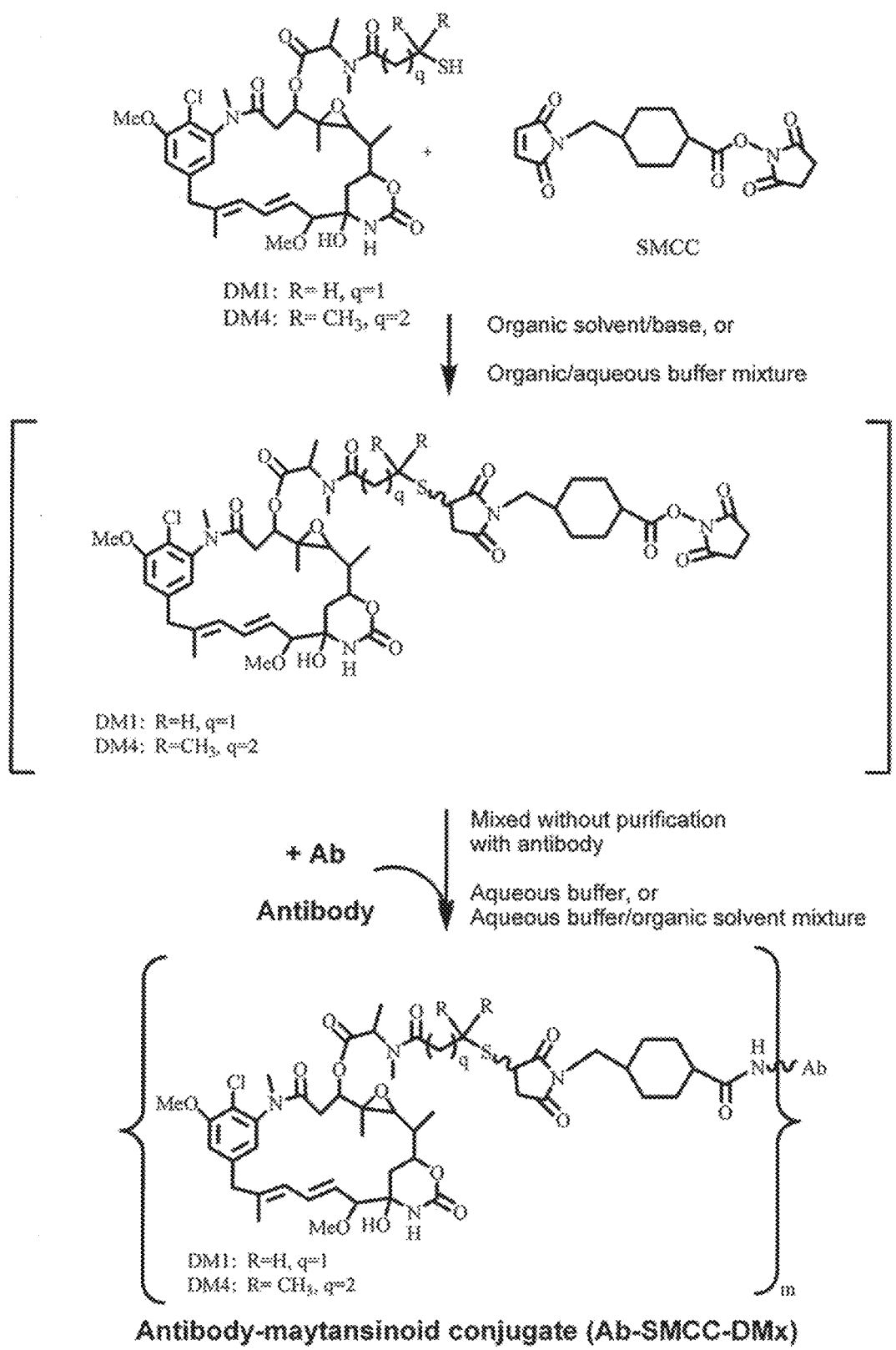
FIG. 22 shows the conjugation of antibody with a reaction mixture of DM1 (or DM4) and SMCC linker.

Example 6. Conjugation of Antibody with Maytansinoid Using SMCC Linker (FIG. 22)

Stock solutions of DM1 thiol and SMCC heterobifunctional linker (Pierce) were prepared in DMA at concentrations of 30-60 mM. Linker and DM1 thiol were mixed together in DMA containing up to 50% v/v of aqueous 200 mM succinate buffer, 2 mM EDTA, pH 5.0 to give a ratio of DM1 to linker of 1.4:1 mole equivalent and a final concentration of DM1 of 1 to 6 mM. After mixing, the reaction was left for up to 4 h at ambient temperature and then an aliquot of the reaction mixture was diluted 10-fold to measure absorbance at 302-320 nm to assess whether all of the maleimide had reacted with thiol. When no further maleimide was present by UV, an aliquot of the reaction was added to an aqueous solution of an antibody in phosphate buffer (pH 7.5-8.5) under final conjugation conditions of 2.5 mg/ml Ab, 70-80% phosphate buffer (aqueous)/30-20% DMA (v/v). The conjugation reaction was allowed to proceed at ambient temperature for 3 h. Ab-DM1 conjugate was purified from excess unreacted or hydrolyzed reagent and excess DM1 using a G25 gel filtration column equilibrated in pH 7.4 phosphate buffer (aqueous). The conjugate was then dialyzed overnight into pH 7.4 phosphate buffer (aqueous) and then filtered through a 0.22 μm filter for final storage. The number of DM1 molecule per Ab molecule in the final conjugate was measured by determining absorbance of the conjugate at 252 and 280 nm and using known extinction coefficients for DM1 and antibody at these two wavelengths. Similarly, conjugates of antibody with DM4 thiol and SMCC can be prepared. These conjugates of antibody with DM1 or DM4 using SMCC linker contain thioether non-cleavable linker.

Figure 23:
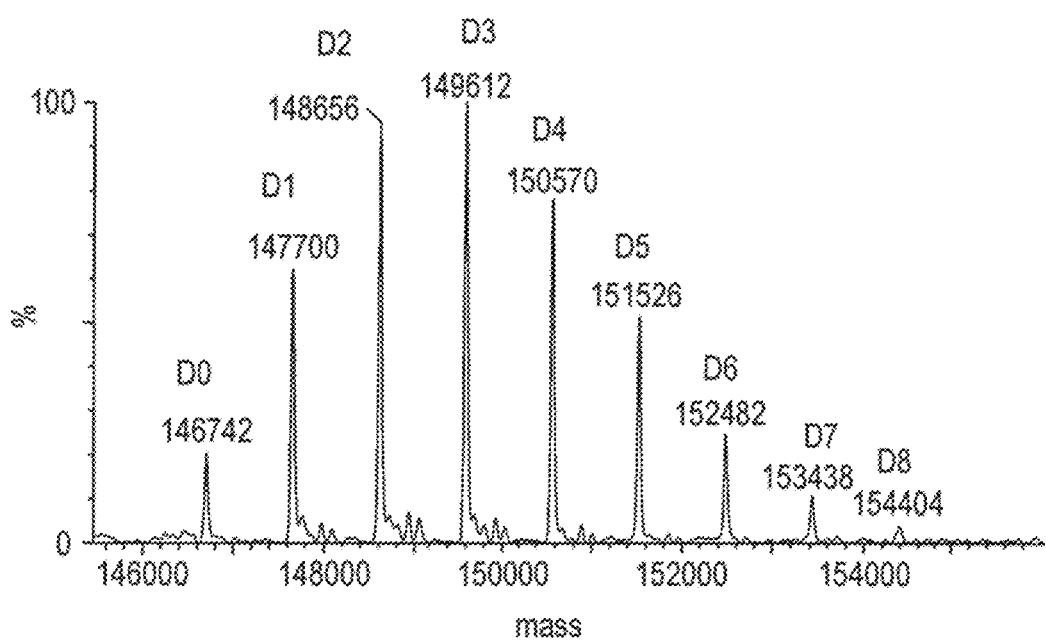
FIG. 23 shows the MS of antibody-SMCC-DM1 conjugate prepared using SMCC by the method described in this invention, containing average 3.1 DM1 per antibody.

The Ab-SMCC-DM1 conjugate made via the method described in this invention was characterized by MS analysis of deglycosylated conjugate (FIG. 23). The conjugate made via the method described in this invention shows the desired MS spectrum containing the expected distribution of peaks with mass equal to Ab-(linker-DM1)$_n$.

Example 7. Conjugation of Antibody with Maytansinoid Using Heterobifunctional Disulfide-Containing Linkers (SSNPB, SPP)

Figure 24:
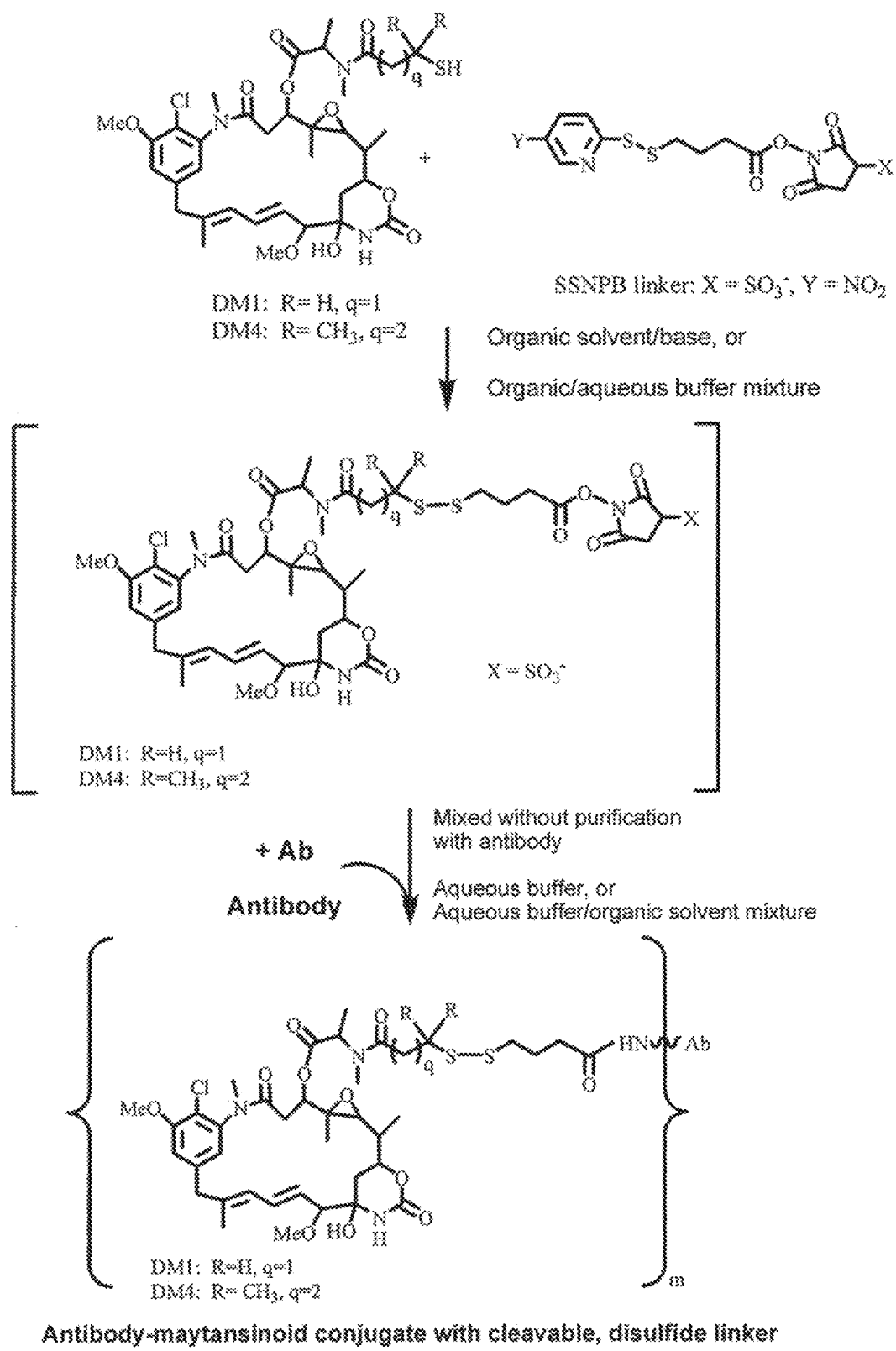
FIG. 24 shows the preparation of disulfide-linked conjugate of antibody using a reaction mixture of DM1 (or DM4) and SSNPB linker.

Disulfide containing heterobifunctional linkers SSNPB (N-sulfosuccinimidyl-4-(5-nitro-2-pyridyldithio)butyrate) and SPP (N-succinimidyl-3-(2-pyridyldithio)propionate) can be used to prepare disulfide-linked antibody-maytansinoid conjugates by the method similar to that described for SPDB linker in Example 4. The structure of the disulfide-linked conjugate prepared using SPDB (FIG. 19) is identical to that of the conjugate prepared with SSNPB (FIG. 24). The MS of a disulfide-linked conjugate prepared using SPDB showed discrete peaks with mass values corresponding to different numbers of maytansinoid molecules attached to antibody.

Figure 25:
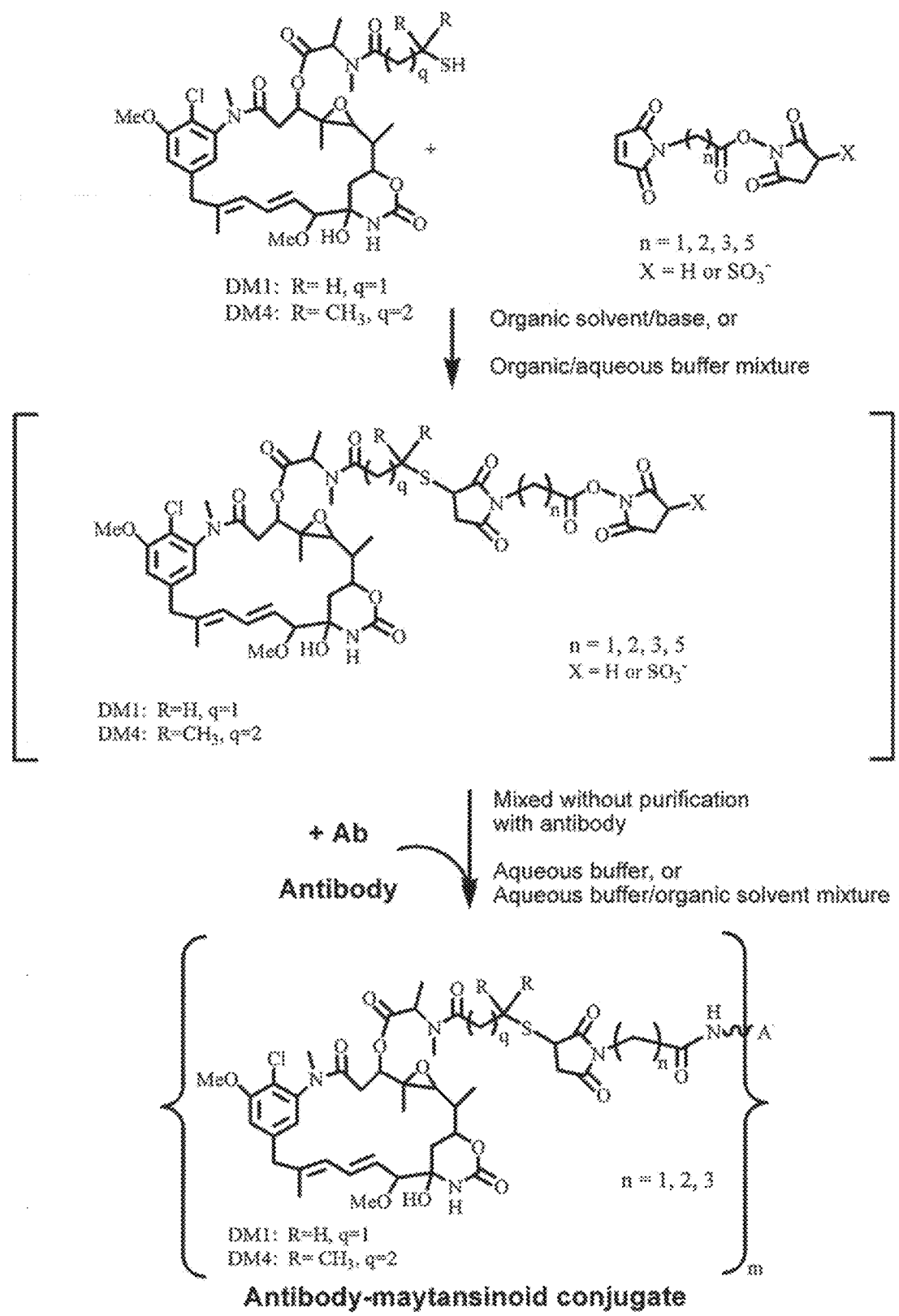
FIG. 25 shows the conjugation of antibody with a reaction mixture of DM1 (or DM4) and heterobifunctional linker with aliphatic linear carbon chain.

Example 8. Conjugation of Antibody with Maytansinoid Containing Non-Cleavable Linkers with Linear Alkyl Carbon Chain Conjugates containing non-cleavable linker with linear alkyl carbon chain were prepared using reaction mixture of maytansinoid and heterobifunctional linkers with linear alkyl carbon chain, similar to the method described for SMCC linker in example 6. For example, conjugates of a humanized antibody with DM1 were prepared using BMPS (N-[β-maleimidopropyloxy]succinimide ester) or GMBS ((N-[γ-maleimidobutyryloxy]succinimide ester) linker as shown in FIG. 26. The initial reaction mixture containing BMPS or GMBS (8 mM) and DM1 thiol (10.4 mM) in 60% DMA/40% (v/v) 200 mM succinate buffer, pH 5, showed complete reaction of maleimide moiety (based on decay of maleimide absorbance at 302-320 nm) when checked at 15 min. This reaction mixture was added, in two portions 30 min apart, to a humanized antibody solution at 2.5 mg/ml in 80% aqueous EPPS buffer, pH 8.1, containing 20% DMA (v/v) with the total linker added at 8 molar equivalents to antibody. The conjugate mixture was gel purified after 4 h and subjected to 2 rounds of dialysis. Conjugates with DM1/antibody ratio of 3.8 and 5.1 were prepared with 71-75% recovery, and high monomer % (96.2-97.6%). These conjugates prepared with GMBS or BMPS showed no unconjugated free drug by HISEP HPLC analysis. Similar conjugates containing non-cleavable linkers with linear alkyl chains can be prepared using AMAS (N-[β-maleimidoacetoxy]succinimide ester) or EMCS (N-[β-maleimidocaproyloxy]succinimide ester) or the sulfo-N-hydroxysuccinimide esters (sulfo-GMBS, sulfo-EMCS) as shown in FIG. 25. Table 1 shows the monomer % for select conjugates prepared by the method described in this invention, which all showed high monomer % by size-exclusion chromatography analysis. For comparison, monomer % are also shown for conjugates prepared by the traditional two-step conjugation method (by the initial reaction of antibody with heterobifunctional linker followed by reaction with mayansinoid thiol).

TABLE 1

Monomer % for select conjugates made by the method described in this application versus by traditional two-step conjugation methods

| Conjugate | D/A | Conjugation method | % Monomer |
|---|---|---|---|
| Ab-PEG$_4$-Mal-DM1 | 6.6 | this invention | 99.0 |
| Ab-PEG$_4$-Mal-DM1 | 6.8 | two-step | 98.0 |
| Ab-Sulfo-Mal-DM1 | 3.6 | this invention | 99.0 |
| Ab-Sulfo-Mal-DM1 | 4.0 | two-step | 96.7 |
| Ab-SMCC-DM1 | 4.0 | this invention | 98.6 |
| Ab-SMCC-DM1 | 3.8 | two-step | 97.0 |
| Ab-PEG$_4$-Mal-DM4 | 6.2 | this invention | 96.9 |
| Ab-PEG$_4$-Mal-DM4 | 6.1 | two-step | 84.5 |
| Ab-SPDB-DM4 | 4.1 | this invention | 99.4 |
| Ab-SPDB-DM4 | 3.9 | two-step, one-pot | 95.7 |

The invention claimed is:

1. A process for preparing a purified conjugate in a solution, wherein the conjugate comprises a maytansinoid comprising a thiol group linked to a cell binding agent, the process comprising the steps of:
    (a) contacting a maytansinoid comprising a thiol group with a bifunctional linker reagent comprising a maleimido-based moiety and an N-hydroxysuccinimide ester group to covalently attach the linker to the maytansinoid and thereby prepare an unpurified first mixture comprising the maytansinoid having linkers bound thereto,
    (b) conjugating a cell binding agent to the maytansinoid having linkers bound thereto by reacting the unpurified first mixture with the cell binding agent to prepare a second mixture, and
    (c) subjecting the second mixture to tangential flow filtration, dialysis, gel filtration, adsorptive chromatography, selective precipitation or a combination thereof to thereby prepare the purified conjugate
    wherein step (b) is carried out in a solution at a pH from about 4 to about 9.

2. The process of claim 1, wherein the pH of the solution in step (b) is from about 5 to about 8.7.

3. The process of claim 1, wherein the pH of the solution in step (b) is from about 6.5 to about 8.5.

4. The process of claim 1, wherein the second mixture in step (b) is substantially free of undesired cross-linked, hydrolyzed species formed due to intramolecular or intermolecular reactions.

5. The process of claim 1, wherein the maytansinoid is DM1.

6. The process of claim 1, wherein the maytansinoid is DM4.

7. The process of claim 1, wherein the cell binding agent is an interferon, interleukin 2 (IL-2), interleukin 3 (IL-3), interleukin 4 (IL-4), interleukin 6 (IL-6), insulin, EGF, TGF-a, FGF, G-CSF, VEGF, MCSF, GM-CSF, transferrin, or an antibody.

8. The process of claim 7, wherein the cell binding agent is an antibody.

9. The process of claim 8, wherein the antibody is a monoclonal antibody.

10. The process of claim 8, wherein the antibody is a human or a humanized monoclonal antibody.

11. The process of claim 8, wherein the antibody is MY9, anti-B4, C242, or an antibody that binds to an antigen selected from EpCAM, CD2, CD3, CD4, CD5, CD6, CD11, CD19, CD20, CD22, CD26, CD30, CD33, CD37, CD38, CD40, CD44, CD56, CD79, CD105, CD138, EphA receptors, EphB receptors, EGFR, EGFRvIII, HER2, HER3, mesothelin, cripto, alphavbeta3, alphavbeta5, and alphavbeta6 integrin.

12. The process of claim 10, wherein the human or the humanized antibody is huMy9-6, huB4, huC242, huN901, DS6, CNTO 95, B—B4, trastuzumab, pertuzumab, bivatuzumab, sibrotuzumab, rituximab, or a human or humanized antibody that binds to an antigen selected from EphA2 receptor, CD38, and IGF-IR.

13. The process of claim 8, wherein the antibody is a fragment of an antibody.

14. The process of claim 13, wherein the fragment of an antibody is a scFv, Fab, Fab' or F(ab')$_2$.

15. The process of claim 1, wherein an excess of maytansinoid relative to the bifunctional linker reagent is used.

16. The process of claim 15, wherein the process further comprises the step of quenching the excess maytansinoid in the unpurified first mixture with a quenching reagent between steps (a) and (b).

17. The process of claim 16, wherein the quenching reagent is selected from 4-maleimidobutyric acid, 3-maleimidopropionic acid, N-ethylmaleimide, iodoacetamide, and iodoacetamidopropionic acid.

18. The process of claim 1, wherein the bifunctional linker reagent comprising a maleimido-based moiety and an N-hydroxysuccinimide ester group is selected from N-succinimidyl 4-(maleimidomethyl)cyclohexanecarboxylate (SMCC), N-succinimidyl-4-(N-maleimidomethyl)-cyclohexane-1-carboxy-(6-amidocaproate), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), and N-succinimidyl 4-(p-maleimidophenyl)-butyrate (SMPB), and N-(p-maleimidophenyl)isocyanate (PMPI).

19. The process of claim 18, wherein the bifunctional linker reagent comprising a maleimido-based moiety and an N-hydroxysuccinimide ester group is γ-maleimidobutyric acid N-succinimidyl ester (GMBS).

\* \* \* \* \*